US010285693B2

(12) United States Patent
Kimsey et al.

(10) Patent No.: US 10,285,693 B2
(45) Date of Patent: May 14, 2019

(54) SURGICAL STAPLER WITH LOCKING TRANSLATABLE PIN

(71) Applicant: Ethicon Endo-Surgery, LLC, Guaynabo, PR (US)

(72) Inventors: John S. Kimsey, Hebron, KY (US); Anil K. Nalagatla, Mason, OH (US); Hector Chow, Cincinnati, OH (US); Sudhir Patel, Cincinnati, OH (US); Douglas B. Hoffman, Harrison, OH (US); Thomas Adams, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 587 days.

(21) Appl. No.: 14/985,501

(22) Filed: Dec. 31, 2015

(65) Prior Publication Data

US 2017/0189021 A1 Jul. 6, 2017

(51) Int. Cl.
*A61B 17/00* (2006.01)
*A61B 17/32* (2006.01)
(Continued)

(52) U.S. Cl.
CPC ........ *A61B 17/072* (2013.01); *A61B 17/0686* (2013.01); *A61B 2017/00477* (2013.01);
(Continued)

(58) Field of Classification Search
CPC .............. A61B 17/115; A61B 17/1152; A61B 17/1155; A61B 2017/1132;
(Continued)

(56) References Cited

U.S. PATENT DOCUMENTS 3,494,533 A 2/1970 Green et al.
3,795,034 A 3/1974 Strekopytov et al.
(Continued)

FOREIGN PATENT DOCUMENTS

CN 201 445 537 U 5/2010
CN 103 083 053 A 5/2013
(Continued)

OTHER PUBLICATIONS

U.S. Appl. No. 12/031,573, filed Feb. 14, 2008.
(Continued)

*Primary Examiner* — Wade Miles
(74) *Attorney, Agent, or Firm* — Frost Brown Todd LLC

(57) ABSTRACT

A surgical instrument and method of manipulating tissue of a patient includes a body, a shaft assembly extending distally therefrom, and an end effector extending distally from the shaft assembly and configured to receive a cartridge for manipulating tissue. The end effector has a distal end portion, a proximal end portion, a gap between the distal and proximal end portions, and a retaining pin. The retaining pin includes a distal head and is selectively movable from an open position to a locked closed position. In the open position, the retaining pin is proximally positioned such that the gap is configured to receive tissue. In the locked closed position, the retaining pin extends across the gap and is configured to capture tissue within the gap. The distal head of the retaining pin is configured engage and secure the distal end portion relative to the proximal end portion via the retaining pin.

20 Claims, 37 Drawing Sheets

(51) Int. Cl.
*A61B 17/068* (2006.01)
*A61B 17/072* (2006.01)
*A61B 90/00* (2016.01)

(52) U.S. Cl.
CPC .............. *A61B 2017/07221* (2013.01); *A61B 2017/07228* (2013.01); *A61B 2017/07285* (2013.01); *A61B 2017/320052* (2013.01); *A61B 2090/036* (2016.02)

(58) Field of Classification Search
CPC .... A61B 2017/1135; A61B 2017/1139; A61B 17/0684; A61B 17/0686; A61B 17/072; A61B 2017/07257; A61B 2017/07264; A61B 17/07228; A61B 2017/07285; A61B 2017/0725
See application file for complete search history.

(56) References Cited

U.S. PATENT DOCUMENTS

| | | | |
|---|---|---|---|
| 4,047,654 | A | 9/1977 | Alvarado |
| 4,216,891 | A | 8/1980 | Behlke |
| 4,568,009 | A | 2/1986 | Green |
| 4,580,712 | A | 4/1986 | Green |
| 4,607,636 | A | 8/1986 | Kula et al. |
| 4,767,044 | A | 8/1988 | Green |
| 4,802,614 | A | 2/1989 | Green et al. |
| 5,071,052 | A | 12/1991 | Rodak et al. |
| 5,403,312 | A | 4/1995 | Yates et al. |
| 5,673,842 | A * | 10/1997 | Bittner .............. A61B 17/07207 227/175.2 |
| 6,817,508 | B1 | 11/2004 | Racenet et al. |
| 6,988,650 | B2 | 1/2006 | Schwemberger et al. |
| 7,000,818 | B2 | 2/2006 | Shelton et al. |
| 7,134,587 | B2 | 11/2006 | Schwemberger et al. |
| 7,147,139 | B2 | 12/2006 | Schwemberger et al. |
| 7,147,140 | B2 | 12/2006 | Wukusick et al. |
| 7,204,404 | B2 | 4/2007 | Nguyen et al. |
| 7,207,472 | B2 | 4/2007 | Wukusick et al. |
| 7,407,076 | B2 | 8/2008 | Racenet et al. |
| 7,422,139 | B2 | 9/2008 | Shelton et al. |
| 7,464,849 | B2 | 12/2008 | Shelton et al. |
| 7,669,746 | B2 | 3/2010 | Shelton, IV |
| 7,670,334 | B2 | 3/2010 | Hueil et al. |
| 7,753,245 | B2 | 7/2010 | Boudreaux et al. |
| 7,845,537 | B2 | 12/2010 | Shelton et al. |
| 7,913,891 | B2 | 3/2011 | Doll et al. |
| 7,980,443 | B2 | 7/2011 | Scheib et al. |
| 8,210,411 | B2 | 7/2012 | Yates et al. |
| 8,308,040 | B2 | 11/2012 | Huang et al. |
| 8,317,070 | B2 | 11/2012 | Hueil et al. |
| 8,220,688 | B2 | 12/2012 | Laurent et al. |
| 8,371,494 | B2 | 2/2013 | Racenet et al. |
| 8,393,514 | B2 | 3/2013 | Shelton et al. |
| 8,561,870 | B2 | 10/2013 | Baxter et al. |
| 8,579,178 | B2 | 11/2013 | Holsten et al. |
| 8,608,045 | B2 | 12/2013 | Smith et al. |
| 8,733,613 | B2 | 5/2014 | Huitema et al. |
| 9,072,535 | B2 | 7/2015 | Shelton et al. |
| 9,101,358 | B2 | 8/2015 | Kerr et al. |
| 9,198,658 | B2 | 12/2015 | Kasvikis |
| 9,566,066 | B2 | 2/2017 | Kasvikis |
| 9,700,316 | B2 | 7/2017 | Mohan et al. |
| 10,045,780 | B2 | 8/2018 | Adams et al. |
| 2005/0139636 | A1 | 6/2005 | Schwemberger et al. |
| 2005/0143759 | A1 | 6/2005 | Kelly |
| 2005/0145672 | A1 | 7/2005 | Schwemberger et al. |
| 2005/0247753 | A1 | 11/2005 | Kelly et al. |
| 2007/0175955 | A1 | 8/2007 | Shelton et al. |
| 2010/0282820 | A1 * | 11/2010 | Kasvikis .............. A61B 17/072 227/181.1 |
| 2013/0334284 | A1 | 12/2013 | Swayze et al. |
| 2014/0263551 | A1 | 9/2014 | Hall et al. |
| 2014/0263552 | A1 | 9/2014 | Hall et al. |
| 2015/0196347 | A1 | 7/2015 | Yates et al. |
| 2017/0189012 | A1 | 7/2017 | Adams et al. |
| 2017/0189015 | A1 | 7/2017 | Adams et al. |
| 2017/0189024 | A1 | 7/2017 | Adams et al. |
| 2017/0189132 | A1 | 7/2017 | Adams et al. |

FOREIGN PATENT DOCUMENTS

| | | |
|---|---|---|
| CN | 102 895 010 B | 12/2014 |
| EP | 0 246 870 A2 | 11/1987 |
| EP | 1 550 407 A2 | 7/2005 |
| EP | 1 550 410 A2 | 7/2005 |
| EP | 1 550 414 A2 | 7/2005 |
| EP | 1 723 914 A1 | 11/2006 |
| EP | 1 997 439 A2 | 12/2008 |
| EP | 2 090 255 A1 | 8/2009 |
| EP | 2 165 653 A2 | 3/2010 |
| EP | 2 248 474 A2 | 11/2010 |
| WO | WO 86/02254 A1 | 4/1986 |
| WO | WO 2015/153340 A2 | 10/2015 |

OTHER PUBLICATIONS

U.S. Appl. No. 14/813,242, filed Jul. 30, 2015.
European Search Report and Written Opinion dated Feb. 22, 2017 for Application No. EP 16207604.6, 11 pgs.
European Search Report and Written Opinion dated Mar. 23, 2017 for Application No. EP 16207608.7, 10 pgs.
European Search Report, Partial, and Written Opinion dated Sep. 14, 2017 for Application No. EP 16207536.0, 11 pgs.
European Search Report and Written Opinion dated Mar. 16, 2017 for Application No. EP 16207619.4, 9 pgs.
European Examination Report dated Jun. 15, 2018 for Application No. EP 16207619.4, 3 pgs.
European Search Report and Written Opinion dated Mar. 13, 2017 for Application No. EP 16207527.9, 7 pgs.
International Search Report and Written Opinion dated Mar. 7, 2017 for Application No. PCT/US2016/066293, 15 pgs.
International Search Report and Written Opinion dated Mar. 23, 2017 for Application No. PCT/US2016/066802, 16 pgs.
International Search Report and Written Opinion dated Jun. 16, 2017 for Application No. PCT/US2016/067429, 13 pgs.
International Search Report and Written Opinion dated Mar. 17, 2017 for Application No. PCT/US2016/067433, 15 pgs.
International Search Report and Written Opinion dated Mar. 13, 2017 for Application No. PCT/US2016/067436, 12 pgs.
U.S. Appl. No. 16/029,893, filed Jul. 9, 2018.

* cited by examiner

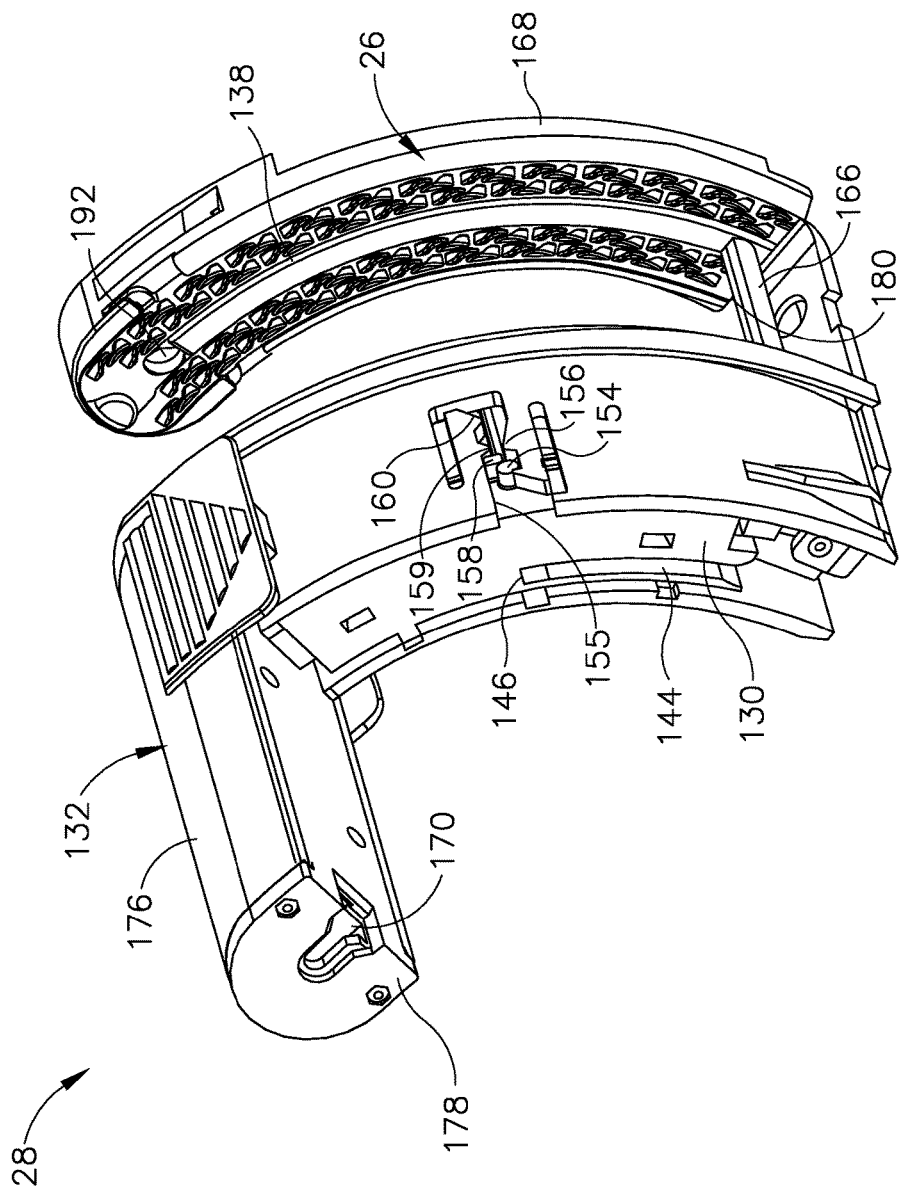

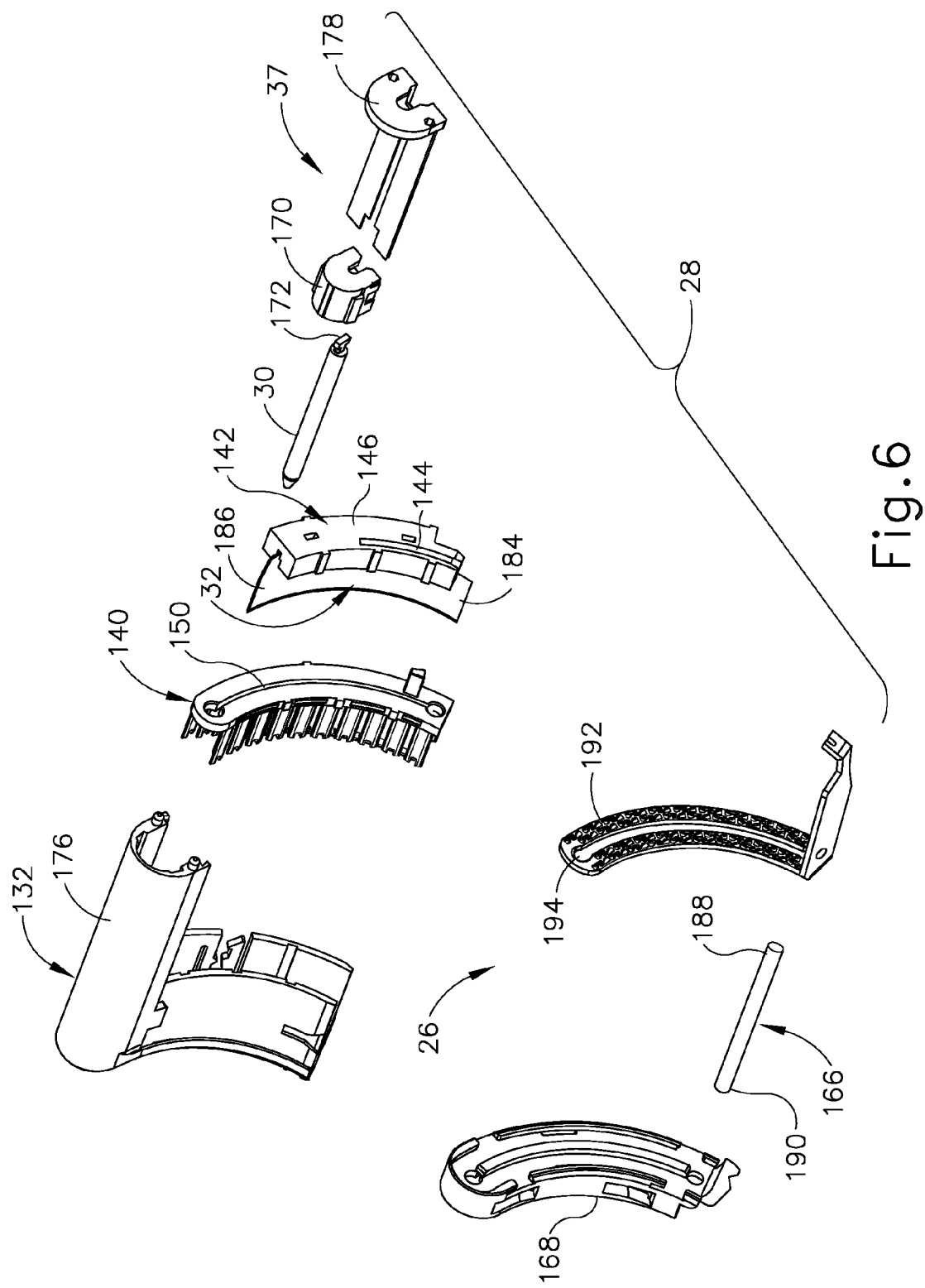

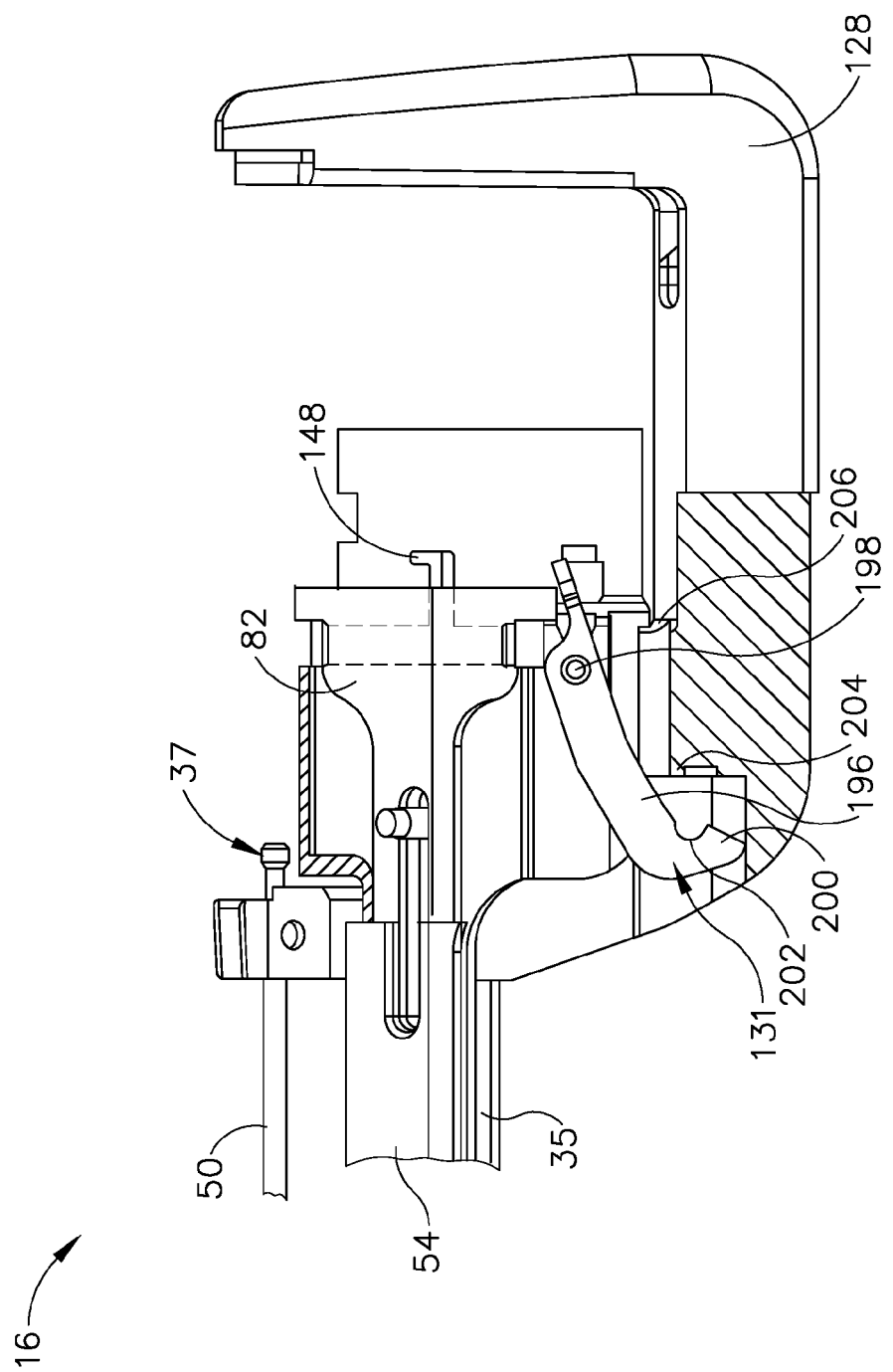

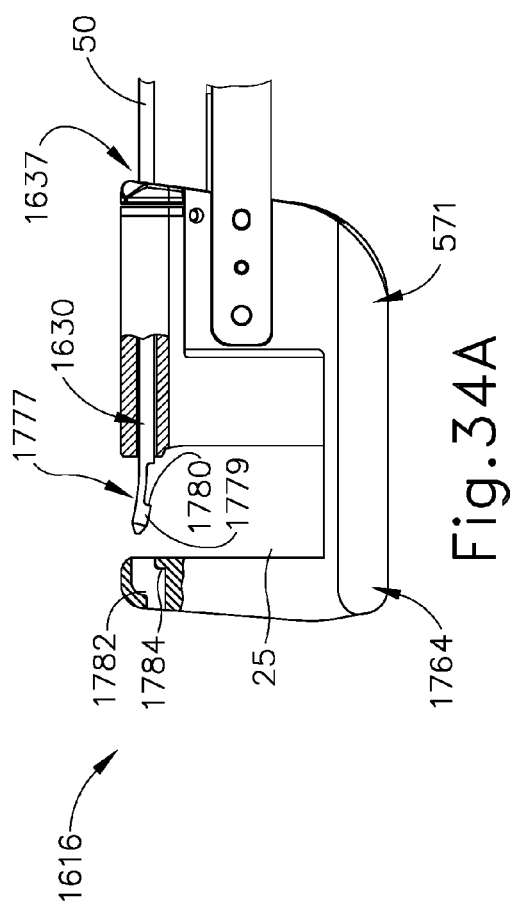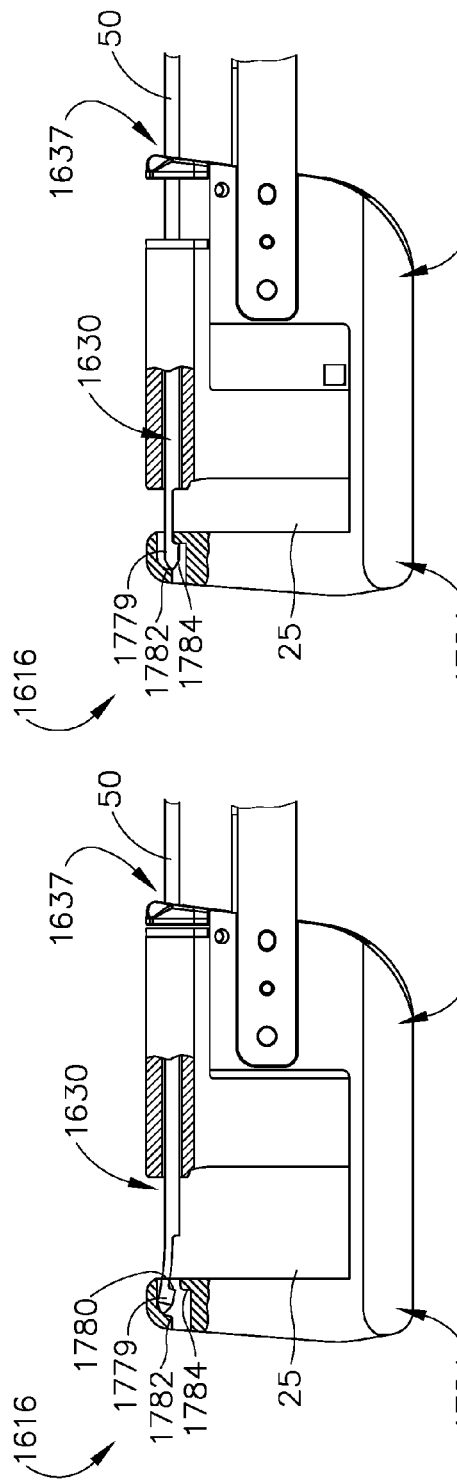

SURGICAL STAPLER WITH LOCKING TRANSLATABLE PIN

BACKGROUND

Some surgical staplers are operable to clamp down on one or more layers of patient tissue, form staples through the layers of tissue to substantially seal the layers of tissue together near the formed staples, and cut through the layers of tissue for forming severed ends of operatively sealed tissue. An exemplary stapling instrument may include a pair of cooperating elongate jaw members, where each jaw member may be adapted to be inserted into a patient and positioned relative to tissue that is to be stapled and/or incised. One of the jaw members may support a staple cartridge with at least two laterally spaced rows of staples contained therein, and the other jaw member may support an anvil with staple-forming pockets aligned with the rows of staples in the staple cartridge. Generally, the stapling instrument may further include a pusher bar and a knife blade that are slidable relative to the jaw members to sequentially or simultaneously eject the staples from the staple cartridge via camming surfaces on the pusher bar and/or camming surfaces on a wedge sled that is pushed by the pusher bar. The camming surfaces may be configured to activate one or more staple drivers carried by the cartridge and associated with the staples in order to push the staples against the anvil and form laterally spaced rows of deformed staples in the tissue gripped between the jaw members. Such rows may be arranged as linear rows and/or arcuate rows for sequentially or simultaneously stapling and cutting the tissue of the patient in the form of a predetermined pattern. The knife blade may trail the camming surfaces and cut the tissue along a linear or arcuate line between the rows of staples formed in the tissue.

Merely exemplary surgical staplers are disclosed in U.S. Pat. No. 6,988,650, entitled "Retaining Pin Lever Advancement Mechanism for a Curved Cutter Stapler," issued Jan. 24, 2006; U.S. Pat. No. 7,134,587, entitled "Knife Retraction Arm for a Curved Cutter Stapler," issued Nov. 14, 2006; U.S. Pat. No. 7,147,139, entitled "Closure Plate Lockout for a Curved Cutter Stapler," issued Dec. 12, 2006, U.S. Pat. No. 7,147,140, entitled "Cartridge Retainer for a Curved Cutter Stapler," issued Dec. 12, 2006; U.S. Pat. No. 7,204,404, entitled "Slotted Pins Guiding Knife in a Curved Cutter Stapler," issued Apr. 17, 2007; and U.S. Pat. No. 7,207,472, entitled "Cartridge with Locking Knife for a Curved Cutter Stapler," issued Apr. 24, 2007. The disclosure of each of the above-cited U.S. Patents is incorporated by reference herein. Additional merely exemplary surgical staplers are disclosed in U.S. Pat. Pub. No. 2005/0139636, entitled "Replaceable Cartridge Module for a Surgical Stapling and Cutting Instrument," published on Jun. 30, 2005, now abandoned; U.S. Pat. Pub. No. 2005/0143759, entitled "Curved Cutter Stapler Shaped for Male Pelvis," published on Jun. 30, 2005, now abandoned; and U.S. Pat. Pub. No. 2005/0145672, entitled "Curved Cutter Stapler with Aligned Tissue Retention Feature," published on Jul. 7, 2005, now abandoned. The disclosure of each of the above-cited U.S. Patent Publications is incorporated by reference herein.

A surgical stapler may be inserted into a patient to perform colorectal surgery. Such procedures may include the use of the stapler to operatively seal, sever, and remove the colon of the patient, in whole or in part. For instance, a proctocolectomy may be performed during a lower anterior resection ("LAR") for treating and inhibiting the spread of colorectal cancer cells. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 5 depicts a rear perspective view of the staple cartridge of FIG. 3;

FIG. 6 depicts an exploded rear perspective view of the staple cartridge of FIG. 3;

FIG. 10B depicts a left side view of the end effector of FIG. 1A, with various components removed for clarity, with the staple cartridge removed from the remainder of the end effector;

FIG. 34A depicts a right side sectional view of another exemplary end effector having a retaining pin in the open position, taken generally along a centerline of the retaining pin, with various components removed for clarity;

FIG. 34B depicts a right side sectional view of the end effector of FIG. 34A, with the retaining pin being moving from the open position to the unlocked closed position; and FIG. 34C depicts a right side sectional view of the end effector of FIG. 34A, with the retaining pin in a locked closed position.

Figure 1A:
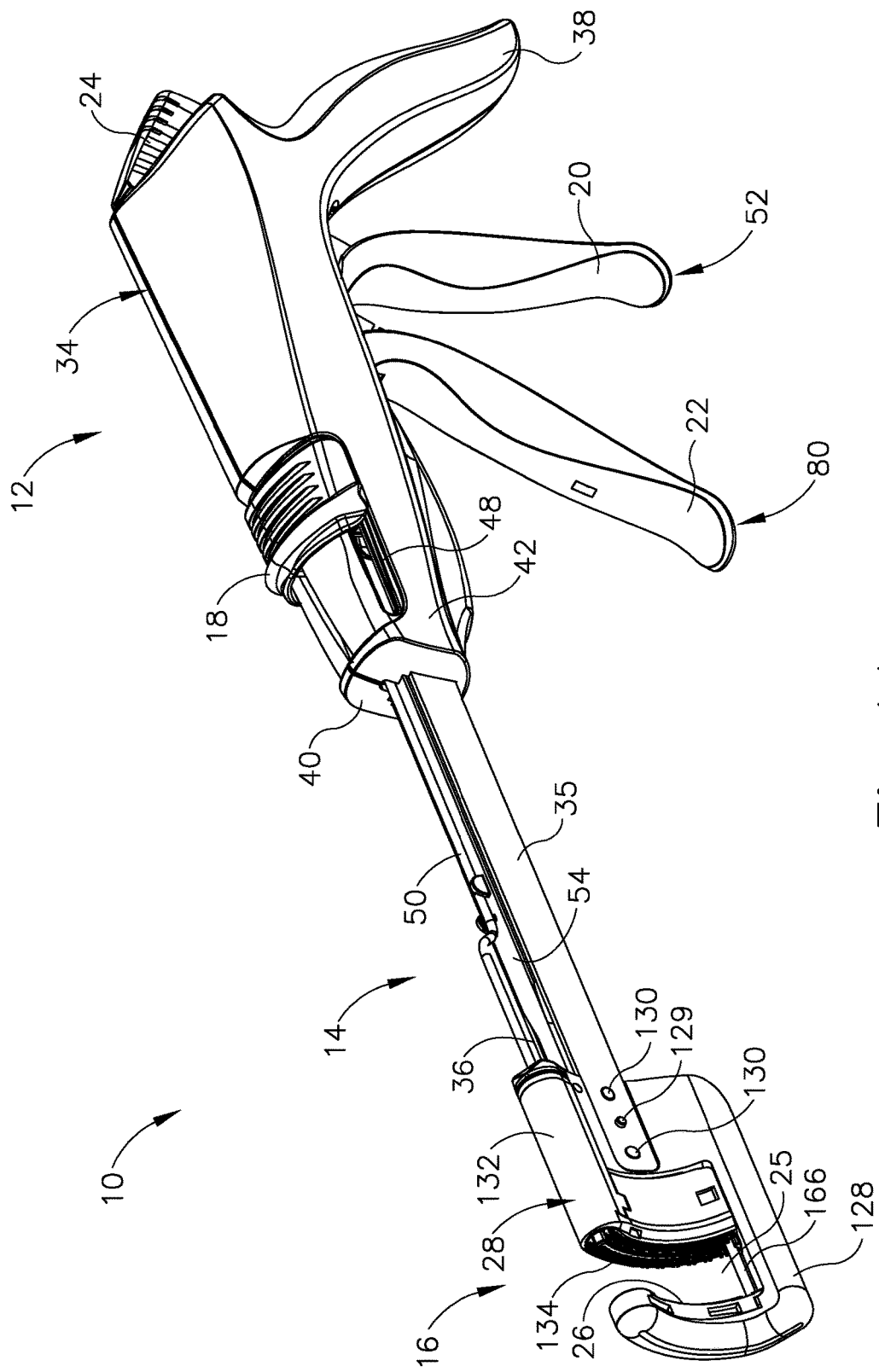
FIG. 1A depicts a right front perspective view of an exemplary surgical stapling instrument with a pin actuation mechanism in an open position and a staple cartridge in open position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that for convenience and clarity, spatial terms such as "vertical," "horizontal," "lower," "upper," "front," and "rear" are used herein with respect to the drawings. However, surgical instruments are used in many orientations and positions, and these terms are not intended to be limiting and/or absolute.

I. Exemplary Surgical Stapler

FIG. 1A depicts an exemplary surgical stapling and severing instrument (10) that includes a handle assembly (12), a shaft assembly (14), and an end effector (16) distally projecting from shaft assembly (14). It should be understood that terms such as "proximal," "distal," "right," and "left" are used herein with reference to a clinician gripping handle assembly (12) of surgical stapling instrument (10). Thus, end effector (16) is distal with respect to the relatively proximal handle assembly (14). Except as otherwise described herein, instrument (10) may be configured and operable in accordance with at least some of the teachings of U.S. Pat. Pub. No. 2005/0143759, entitled "Curved Cutter Stapler Shaped for Male Pelvis," published on Jun. 30, 2005, now abandoned, the disclosure of which is incorporated by reference herein; and/or U.S. patent application Ser. No. 14/813,242 entitled "Surgical Instrument Comprising Systems for Assuring the Proper Sequential Operation of the Surgical Instrument," filed on Jul. 30, 2015, issued as U.S. Pat. No. 10,194,913 on Feb. 5, 2019, the disclosure of which is incorporated by reference herein.

Figure 1B:
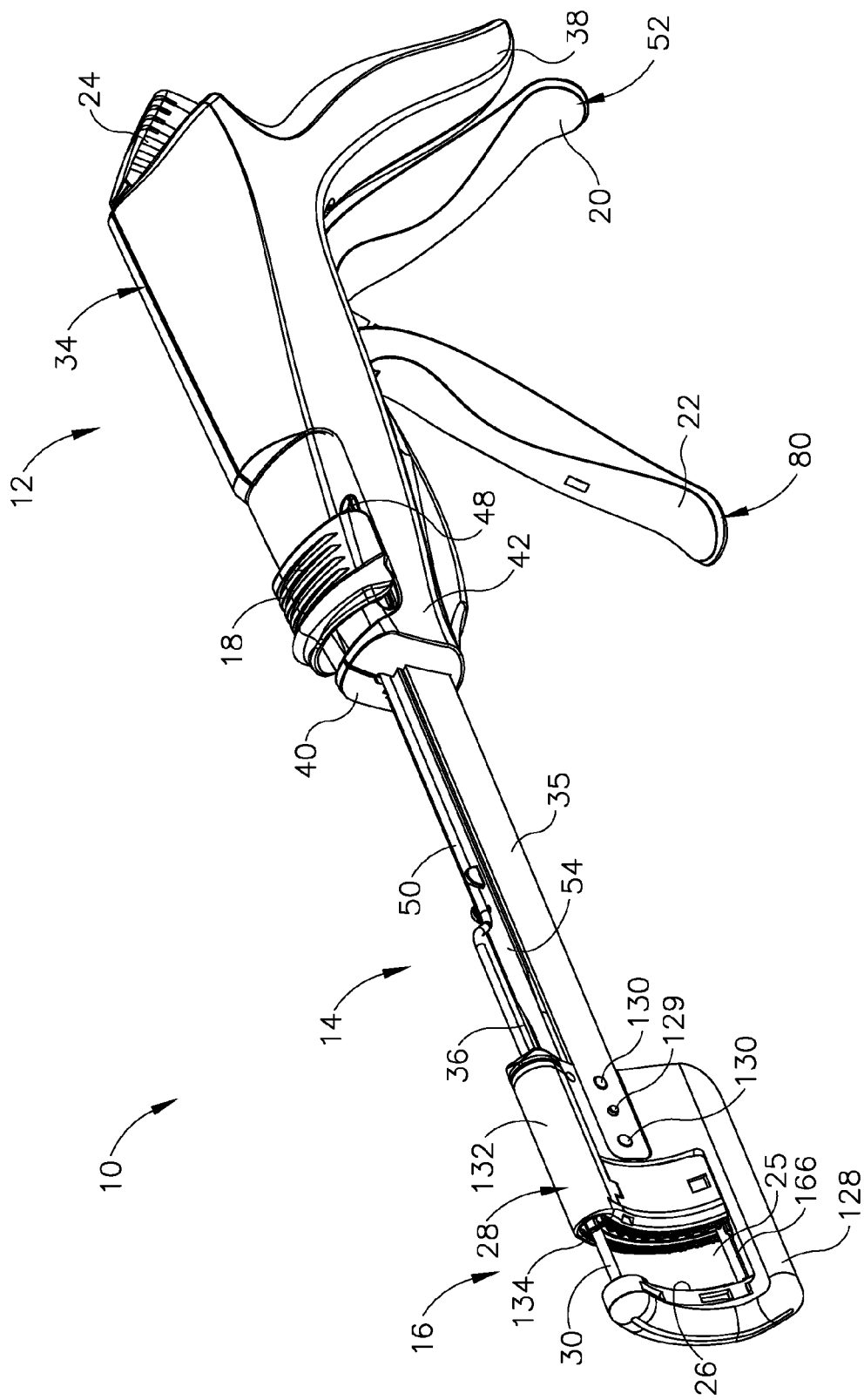
FIG. 1B depicts a right front perspective view of the surgical stapling instrument of FIG. 1A with the pin actuation mechanism in a closed position and the staple cartridge in the open position.

Handle assembly (12) includes several actuation mechanisms for operating end effector (16) during the surgical procedure. To this end, exemplary handle assembly (12) includes a saddle shaped slide (18), a closure trigger (20), and a firing trigger (22) in communication with end effector (16) via shaft assembly (14). As shown in FIG. 1A, slide (18) and closure trigger (20) are in open configurations such that end effector (16) is configured to receive tissue laterally within a gap (25) between an anvil (26) and a cartridge (28) of end effector (16). Translating slide (18) distally toward end effector (16) slides a retaining pin (30) of end effector distally as shown in FIG. 1B for capturing the tissue between anvil (26) and cartridge (28). With respect to FIGS. 1C and 1D, sequentially actuating closure trigger (20) and firing trigger (22) respectively compresses the tissue between anvil (26) and cartridge (28) in a closed configuration and then forms a plurality of staples (not shown) within the tissue and severs the tissue with a knife (32) (see FIG. 6) for treatment. Additional details regarding these exemplary actuation mechanisms will be provided below in greater detail.

A. Exemplary Handle Assembly and Shaft Assembly

Figure 2A:
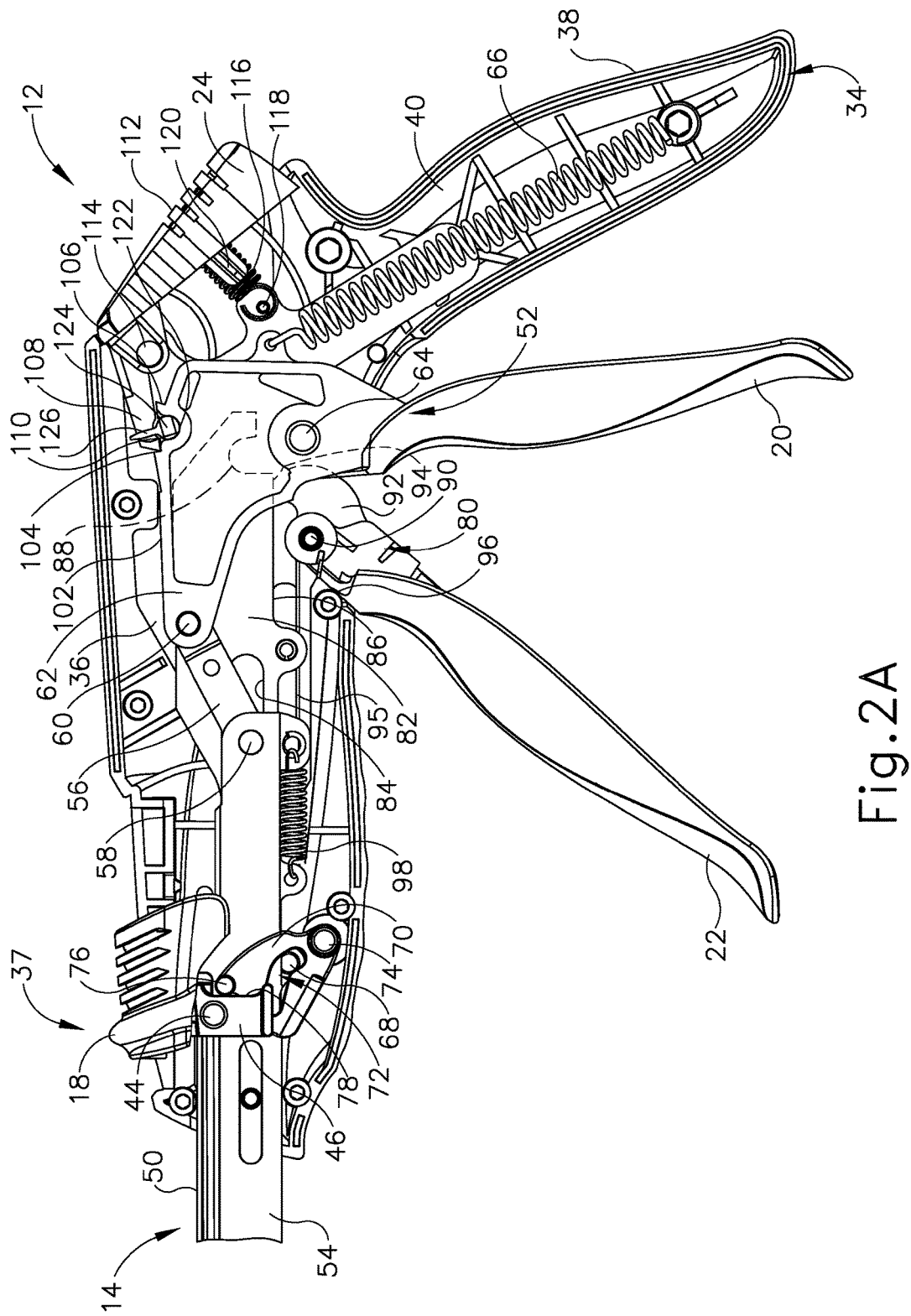
FIG. 2A depicts a right side view of a handle assembly of the surgical stapling instrument of FIG. 1A, with various components removed for clarity, and with the pin actuation mechanism in a closed position and the staple cartridge in the open position.

As shown in FIGS. 1A and 2A, handle assembly (12) has a handle housing (34), a pair of handle frame plates (35, 36) within handle housing (34) extending along shaft assembly (14), saddle shaped slide (18), closure trigger (20), and firing trigger (22) as briefly discussed above. Handle housing (34) defines a hand grip (38), which the operator, such as a surgeon, grasps with the palm of at least one hand. Handle housing (34) is formed by a right shroud handle portion (40) and a left shroud handle portion (42). Closure trigger (20) is proximally positioned relative to firing trigger (22) and each are pivotally mounted to frame plates (35, 36) to extend underneath a remainder of handle assembly (12) for manipulation by the fingers of the operator. Closure and firing triggers (20, 22) are shown in unactuated positions prior to closing end effector (16) and firing staples (not shown) and/or knife (32) (see FIG. 6). Consequently, cartridge (28) is spaced from anvil (26) for receiving tissue within gap (25) therebetween.

Surgical stapling instrument (10) captures tissue via a tissue retaining pin actuation mechanism (37) prior to actuation of the closure and firing triggers (20, 22). FIG. 1A shows retaining pin actuation mechanism (37), which includes slide (18), in the open configuration, whereas FIG. 2A shows retaining pin actuation mechanism (37) in the closed configuration in greater detail. With respect to FIG. 2A, slide (18) is mounted on an upper surface of handle housing (34) and is configured to linearly translate between proximal and distal positions. Slide (18) connects to posts (44), which extend laterally outwardly from a push rod driver (46), through slots (48) (see FIG. 1A). Push rod driver (46) is restrained within handle housing (34) along longitudinal movement by slots (48). Push rod driver (46) is connected to a proximal end of a push rod (50). A distal end of push rod (50) connects to retaining pin (30) (see FIG. 6) such that distal movement of slide (18) causes push rod (50) to similarly slide proximally along shaft assembly (14) for moving retaining pin (30) (see FIG. 6) to the closed configuration, which will be discussed below in greater detail.

A closure mechanism (52), which includes closure trigger (20), is configured to selectively move cartridge (28) toward the tissue positioned between anvil (26) and cartridge (28) in the closed configuration in anticipation of stapling and/or cutting the tissue. Closure mechanism (52) further includes an elongated closure member (54), with a generally U-shaped cross-section, extending distally from handle assembly (12), through shaft assembly (14), and into end effector (16) for receiving a cartridge (28) (see FIG. 3) at a distal end portion thereof as discussed below. A proximal end portion of closure member (54) is operatively connected to closure trigger (20) by a plurality of linkages configured to convert pivoting motion of closure trigger (20) into translation of closure member (54). More particularly, the intermediate and proximal end portions of closure member (54) extend through handle assembly (12) between left and right handle frame plates (35, 36). Right and left closure links (56) are respectively pivotally attached at the right and left proximal ends of closure member (54) by an integral closure link pin (58). At an opposite end of the closure links (56), closure links (56) are pivotally attached to another integral closure link pin (60). Closure link pin (60) connects closure links (56) to a slotted closure arm link (62), which is pivotally mounted to handle frame plates (35, 36) at a closure trigger pin (64). Closure trigger (20) descends from the slotted closure arm link (62) for pivotal rotation about closure trigger pivot pin (64) both toward and away from hand grip (38). A closure spring (66) housed within hand grip (38) is secured to the slotted closure arm link (62) to provide a desired resistance when the operator squeezes closure trigger (20) toward hand grip (38), and to bias closure trigger (20) toward the open position.

Closure member (54) is further configured for directing movement of tissue retaining pin actuation mechanism (37) to automatically direct movement of the retaining pin (30) to the closed configuration while the operator squeezes closure trigger (20). Such automation may be useful in the event that the operator did not manually move the slide (18) to the distal position before actuating trigger (20). Closure member (54) includes posts (68), which extend laterally on each opposing side of closure member (54) within handle housing (34). Posts (68) slidably connect to a yoke (70) via L-shaped slots (72). Yoke (70) is pivotally mounted within handle housing (34) by a pivot pin (74). Yoke (70) further includes cam pins (76) that are configured to push camming surfaces (78) on push rod driver (46). Thus, actuating closure trigger (20) to an intermediate position shown in FIG. 2A directs the closure member (52) distally and, in turn, causes yoke (70) to engage push rod driver (46) and force retaining pin (30) (see FIG. 1B) to the closed position. Slide (18) is thereby dragged along handle housing (34) from the proximal position to the distal position in the event that the operator did not manually manipulate slide (18) to the distal position before actuating trigger (20).

Figure 1C:
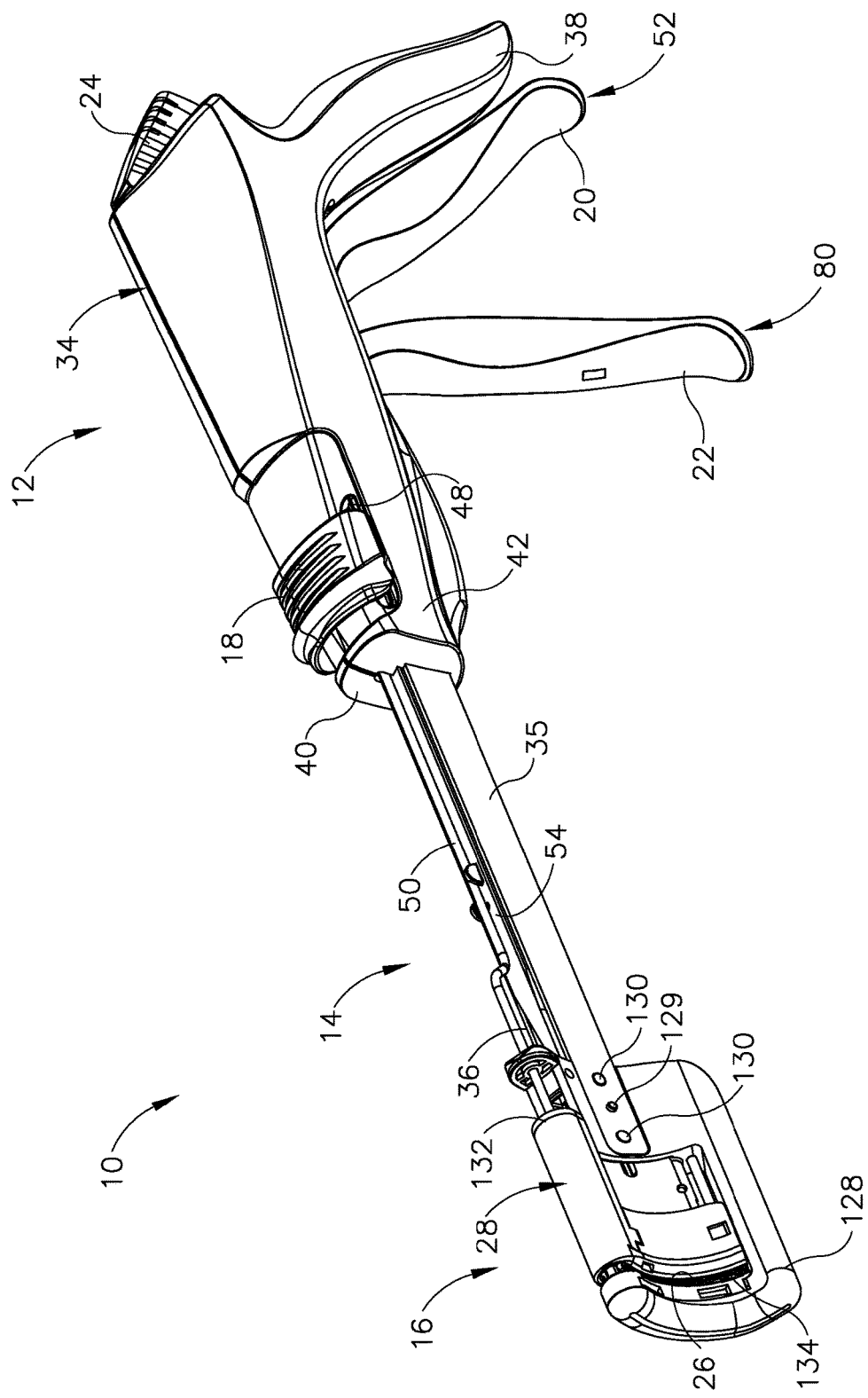
FIG. 1C depicts a right front perspective view of the surgical stapling instrument of FIG. 1A with the pin actuation mechanism in the closed position and the staple cartridge in a closed position via actuation of a closure mechanism.
Figure 1D:
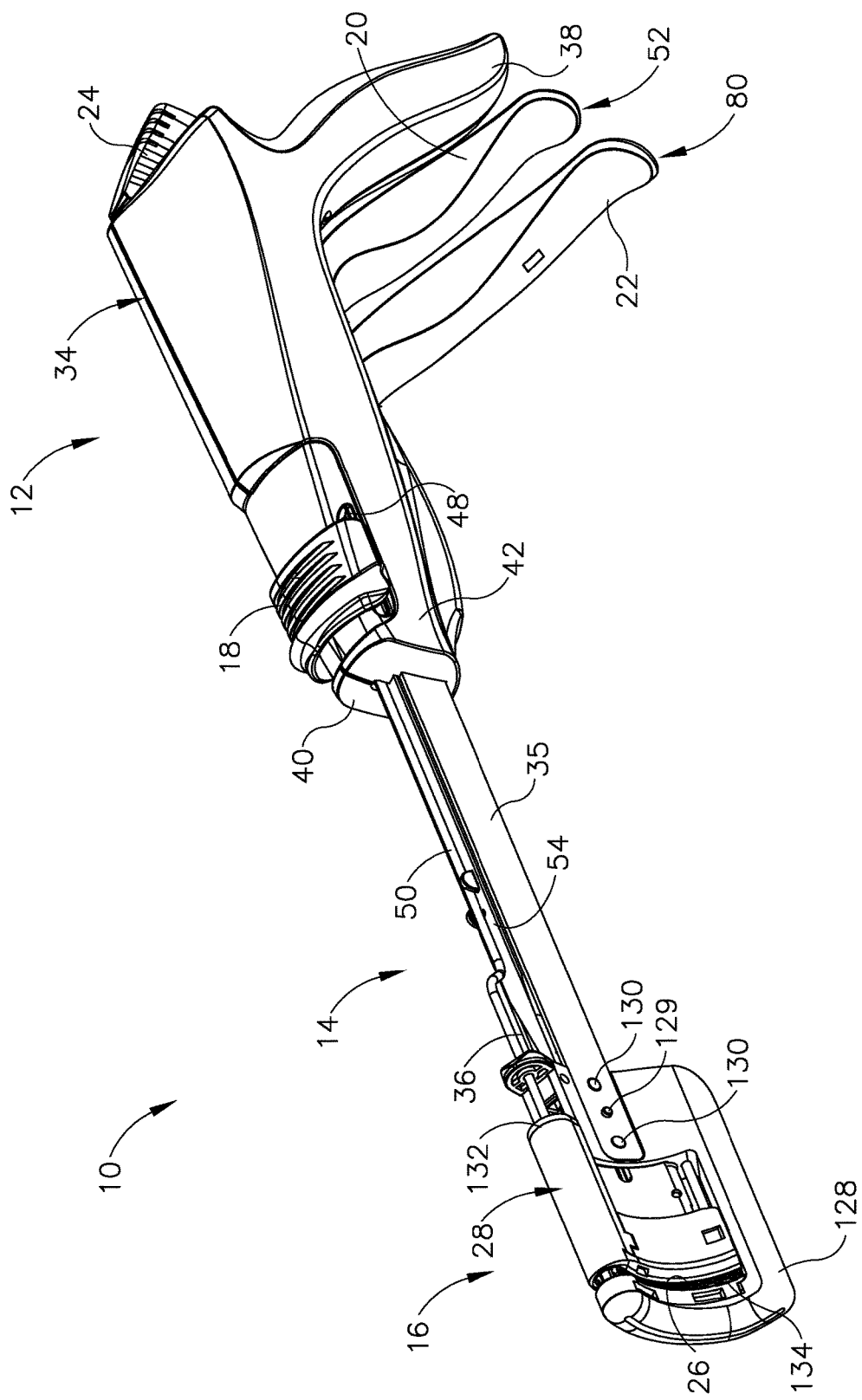
FIG. 1D depicts a right front perspective view of the surgical stapling instrument of FIG. 1A with the pin actuation mechanism and the staple cartridge in the closed positions and a firing trigger in a fired position for stapling and cutting tissue of a patient.
Figure 2B:
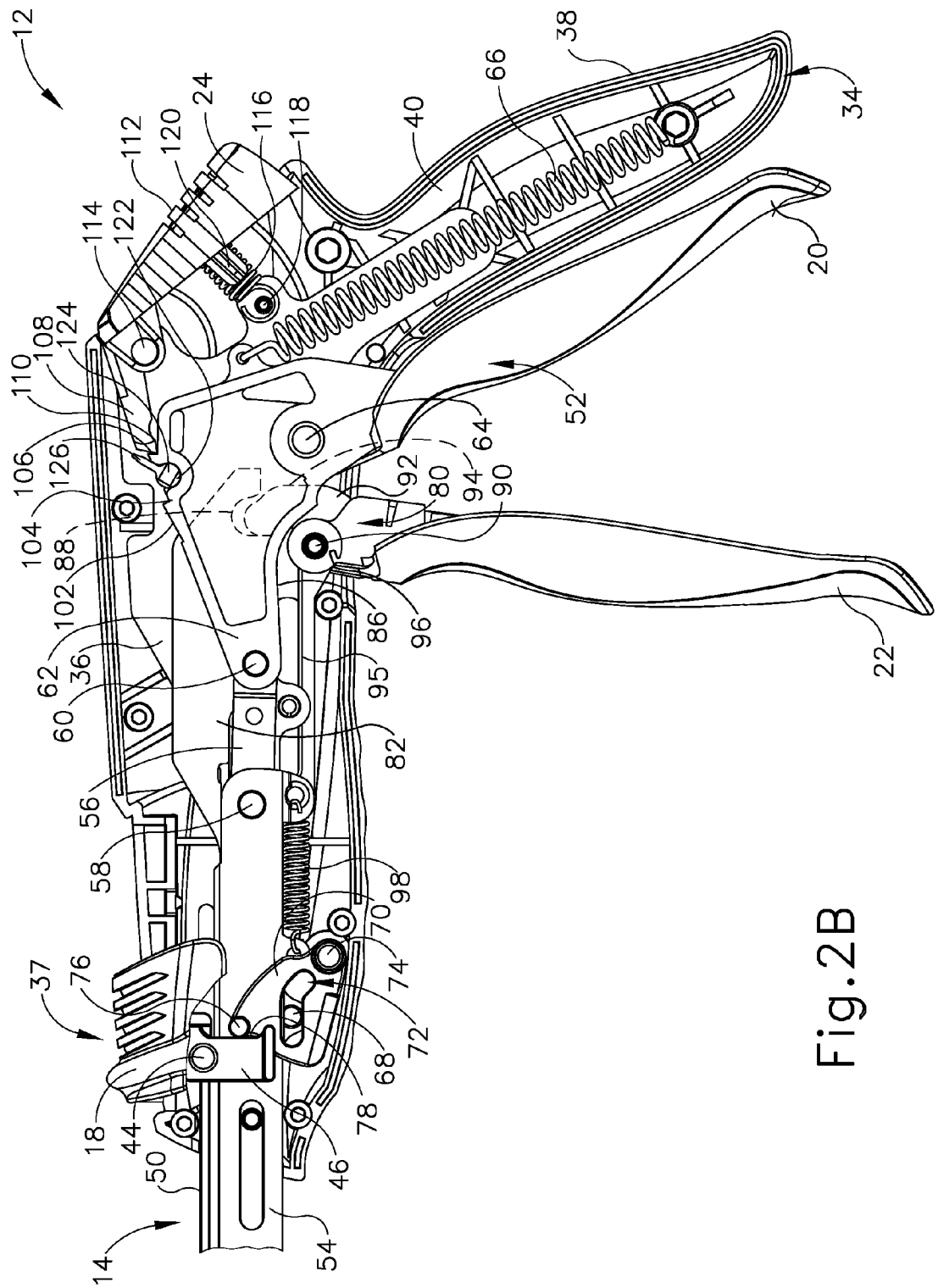
FIG. 2B depicts a right side view of the handle assembly of the surgical stapling instrument of FIG. 1A, with various components removed for clarity, and with the pin actuation mechanism in the closed position and the staple cartridge in the closed position via actuation of the closure mechanism.
Figure 2C:
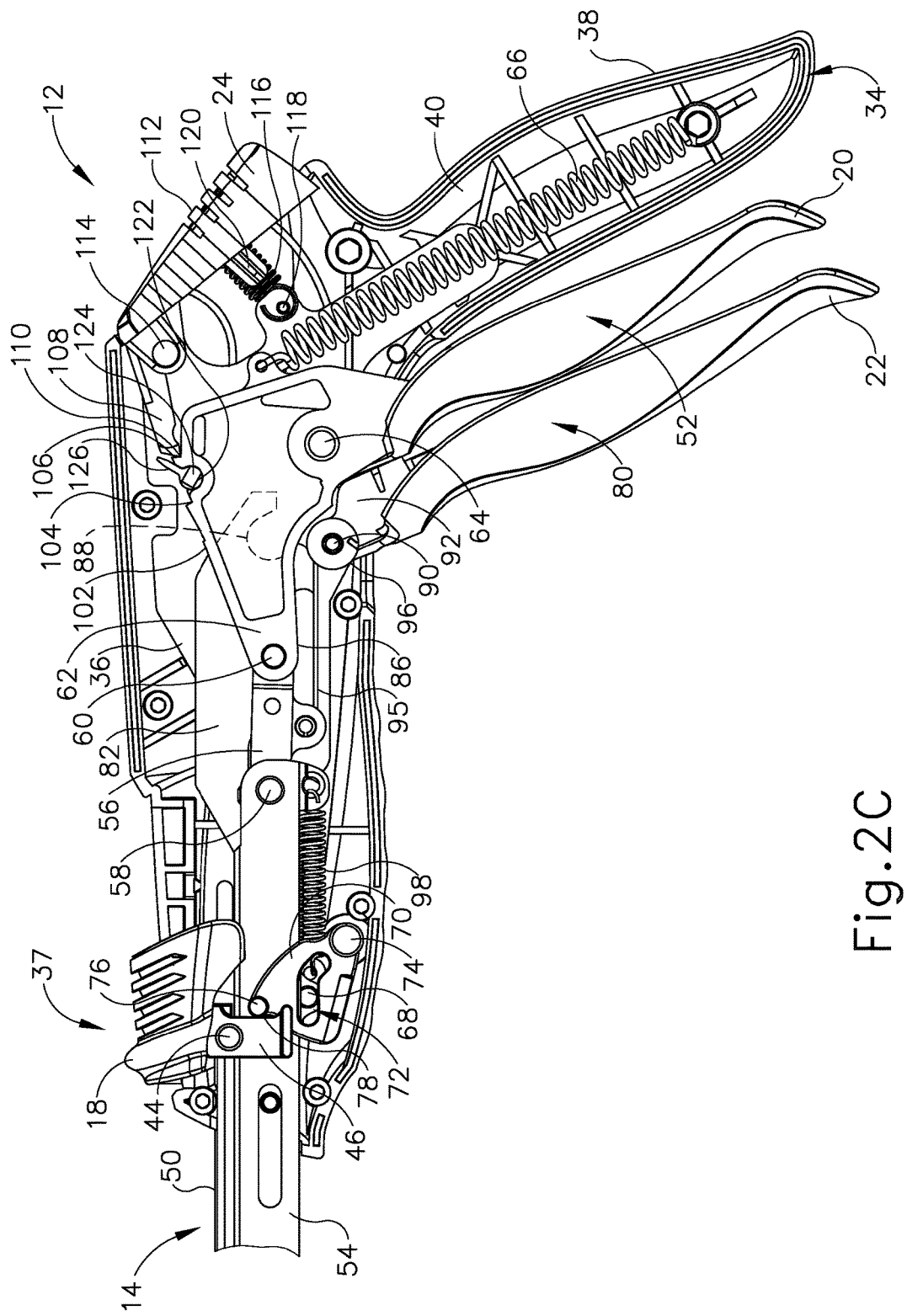
FIG. 2C depicts a right side view of the handle assembly of the surgical stapling instrument of FIG. 1A, with various components removed for clarity, and with the pin actuation mechanism and the staple cartridge in the closed positions and the firing trigger in the fired position for stapling and cutting tissue of a patient.

The operator further squeezes the closure trigger (20) to the hand grip (38) as shown in FIGS. 1C and 2B to effectively set surgical stapling instrument (10) in the closed configuration prior to forming the staples (not shown) and severing the tissue as discussed briefly above. Exemplary handle assembly (12) is configured to form the staples (not shown) and sever the tissue via a firing mechanism (80) upon operator manipulation of firing trigger (22) toward closure trigger (20) as shown in FIGS. 1D and 2C. With respect to FIGS. 1C, 1D, 2B, and 2C, firing mechanism (80), which includes firing trigger (22), has a firing bar (82) extending distally from handle assembly (12) and within end effector (16). A distal end of firing bar (82) cooperates with cartridge (28) as discussed below in greater detail, whereas a proximal end of firing bar (82) is operatively connected to firing trigger (80) for selective firing thereof.

Firing bar (82) has a rectangular receiving slot (84) (see FIG. 2A) in a portion of firing bar (82) positioned within handle housing (34). Integral closure link pin (58) extends through receiving slot (84). The underside of the proximal end portion of firing bar (82) has a sliding surface (86). The proximal end portion of firing bar (82) also has a terminal side engagement surface (82) extending from sliding surface (86). Firing trigger (22) is pivotally mounted to handle frame plates (35, 36) by a firing trigger pin (90) spaced from closure trigger pin (64) such that each of pins (90, 64) pivot about mutually independent axes. Firing trigger (22) includes an arcuate firing trigger link (92) extending from firing trigger (22) at firing trigger pin (90) to an apex (94), which rests on sliding surface (86) of the proximal end portion of firing bar (82). Within handle assembly (12), firing trigger (22) is attached to firing trigger spring arms (95, 96), respectively. Firing trigger spring arms (95, 96) support a torsion spring (not shown) on the right half of firing trigger (22). Finally, a firing bar return spring (98) is secured to the underside of firing bar (82) at the portion of firing bar (82) within handle assembly (12) to bias firing bar (82) toward its unactuated position.

As the operator squeezes closure trigger (20) toward hand grip (38), slotted closure arm link (62) and closure links (56) move distally within receiving slot (84) of firing bar (82). This distal movement causes closure member (54) to correspondingly move distally. Likewise, firing bar (82) concurrently moves distally with closure member (54), because integral closure link pin (58), to which closure links (56) are attached, extends through receiving slot (84) in firing bar (82) (see FIG. 2A). Thereby, firing bar (82) is forced distally to form the staples (not shown) in the tissue and/or sever the tissue with knife (32) (see FIG. 6). Finally, the operator may fully squeeze firing trigger (22) toward hand grip (38) to "fire" surgical stapling instrument (10) and force firing bar (82) further distally to form the staples (not shown) and sever the tissue. This distal movement of firing bar (82) may also be referred to herein as "firing" the firing bar (82) to the actuated or "fired" position.

Upon operator release of one or both of closure and firing triggers (20, 22) while one or both of triggers (20, 22) is/are in a fired position, or in an intermediate position between the unactuated and fired positions, surgical stapling instrument (10) may be further configured to releasably lock in one of a variety of configurations. The operator may then release the hand grip (38) to free one or more hands for another task during the surgical procedure and, when desired, release surgical stapling instrument (10) from its locked position by release button (24). By way of example, surgical stapling instrument (10) has an intermediate closure detent position and a closure detent position. With respect to FIGS. 2A-2C, the top side of the slotted closure arm link (62) has a clamp sliding surface (102) that displays an intermediate detent (104) and a closure detent (106). A release pawl (108) slides on clamp sliding surface (102) and may engage intermediate and closure detents (104,106). Release pawl (108) has a laterally extending pawl lug (110) at its distal end.

Release pawl (108) is located within handle assembly (12) and is integrally formed with release button (24), which is situated exterior of handle housing (34) for manipulation by the operator. Release button (24) has a thumb rest (112) pivotally attached to handle housing (34) by a release trunnion (114). Release button (24) is biased outwardly from handle housing (34) and, therefore, release pawl (108) is biased downwardly toward clamp sliding surface (102) by a release spring (116). Release spring (116) is mounted to handle housing (34) by a spring retention pin (118) and is mounted to release button (24) by a button spring post (120). Slotted closure arm link (62) has an arcuate recess (122) located between intermediate and closure detents (104, 106). Resting within arcuate recess (122) for rotational movement are integrally connected left and right hand toggles (124). Each toggle (124) has a toggle arm (126) that is engageable with pawl lug (110).

In order to releasably lock handle assembly (12), toggle arms (126) from pawl lug (110) disengage from pawl lug (110) as closure trigger (20) is squeezed toward hand grip (38). Consequently, as toggle (124) continues to rotate in a clockwise direction, release pawl lug (108) rides up toggle arms (126) and, with continued motion of closure trigger (20), falls into one of intermediate and closure detents (104, 106), depending on the position of closure trigger (20) in use. As release pawl (108) rides up toggle arm (126), release pawl (108) rotates release button (24) clockwise. Release pawl (108) thereby falls into one of intermediate and detents (104, 106) and generates an audible clicking sound alerting the surgeon that one of the intermediate and closure positions have been reached.

In order to release handle assembly (12) from the intermediate or closure positions discussed herein, the surgeon depresses release button (24). In turn, release pawl (108) pivots about release trunnion (114) in a clockwise direction to dislodge pawl lug (110) from one of the intermediate and closure detents (104, 106). As pawl lug (110) is dislodged, pawl lug (110) rides on toggle arms (126) to another position, such as the unactuated position. Therefore, the operator may release closure and firing triggers (20, 22) such that each may return to the unactuated positions FIG. 1A and FIG. 3.

Surgical stapling instrument (10) of the present example includes each of handle frame plates (35, 36), push rod (50), closure member (54), and firing bar (82) extending continuously from handle assembly (12) to end effector (16), thereby defining shaft assembly (14) extending therebetween. Handle frame plates (35, 36), push rod (50), closure member (54), and firing bar (82) of surgical stapling instrument (10) provide merely a subset of elongated components extending distally from handle assembly (12) as shaft assembly (14). Alternatively, shaft assembly (14) may include additional components, such as an articulating joint, or may include a rearrangement of various components such that shaft assembly (14) may be modular relative to handle assembly (12). In any case, it will be appreciated that the invention is not intended to be limited to shaft assembly (14) described herein, and may include various alternative arrangements for operatively connecting end effector (16) to handle assembly (12). Of course, handle assembly (12) and shaft assembly (14) may have a variety of other components, features, and operabilities, in addition to or in lieu of any of those noted above. Other suitable configurations for handle and shaft assemblies (12, 14) will be apparent to those of ordinary skill in the art in view of the teachings herein.

B. Exemplary End Effector

Figure 3:
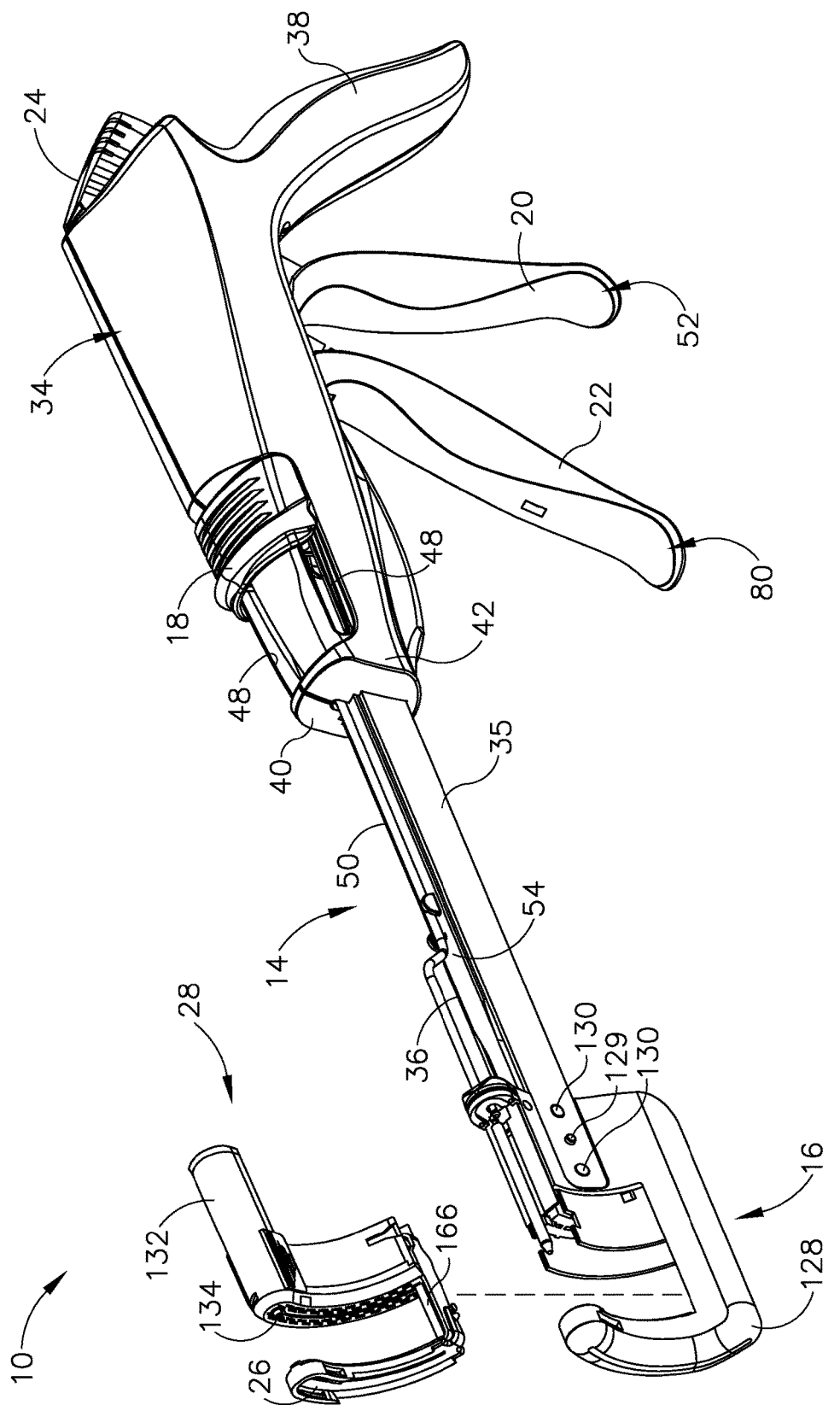
FIG. 3 depicts a partially exploded right front perspective view of the surgical stapling instrument of FIG. 1A showing the staple cartridge removed from a remainder of an end effector.
Figure 4:
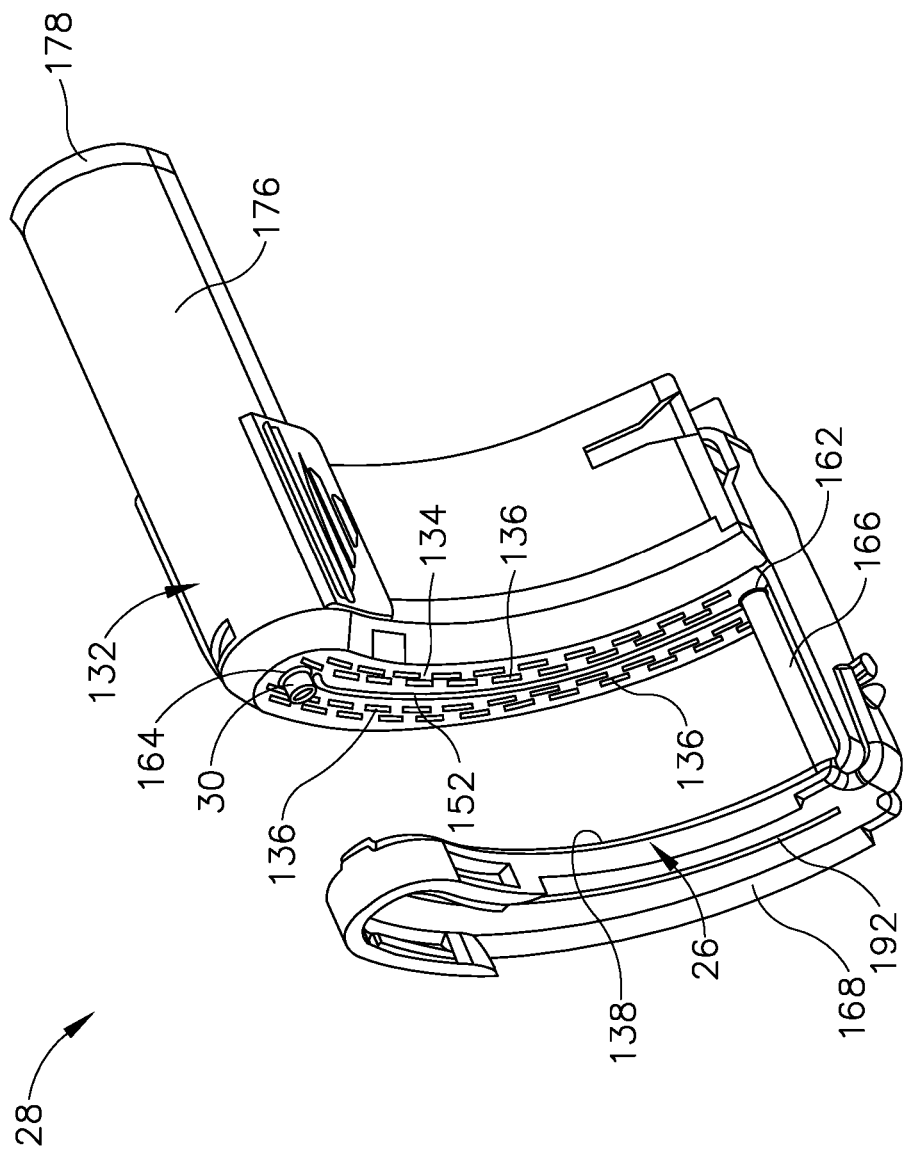
FIG. 4 depicts a right front perspective view of the staple cartridge of FIG. 3.

As also shown in FIGS. 3-5 and discussed briefly above, end effector (16) of the present example includes anvil (26), replaceable cartridge (28) including a plurality of staples (not shown) and knife (32) (see FIG. 6), and retainer pin (30). While end effector (16) of the present example is adapted for use in conjunction with replaceable cartridge (28) having various components, it will be appreciated that the concepts underlying the present invention could be applied to a variety of end effector and cartridge constructions for treating the patient.

End effector (16) provides a surgical fastening assembly that includes cartridge (28) received within a C-shaped supporting structure (128). The term C-shaped is used throughout the specification to describe the concave nature of supporting structure (128) and cartridge (28). The C-shaped construction facilitates enhanced functionality and access to tissue within the patient. The term "C-shaped" as used herein should be construed to include a variety of concave shapes that would similarly enhance the functionality of surgical stapling and cutting instruments. By way of example only, the C-shape of supporting structure (128) may be sized to promote access to the lower colon within the pelvic bowl of a patient, such as to perform a LAR in a proctocolectomy procedure.

Supporting structure (128) of end effector (16) is respectively attached to handle frame plates (35, 36) of shaft assembly (14) by a shoulder rivet (129) and posts (130) which extend from supporting structure (128) into receiving holes in handle frame plates (35, 36). The distal end of closure member (54) is disposed to receive cartridge (28) thereon for directing cartridge (28) to the closed configuration. Upon return of cartridge (28) from the closed configuration to the open configuration, cartridge (28) further includes a safety lockout mechanism (131) (see FIG. 7A) configured to inhibit inadvertently re-firing cartridge (28). Safety lockout mechanism (131) will be discussed below in additional detail Cartridge (28) includes anvil (26) coupled to a cartridge housing (132). Cartridge (28) also includes retaining pin (30) and a tissue contacting surface (34), which defines a plurality of staple-containing slots (136) in staggered formation in one or more rows on either side of knife (32) (see FIG. 6). Staples (not shown) are fired from cartridge housing (132) against a staple-forming surface (138) of anvil (26) that faces tissue-contacting surface (134) of cartridge housing (132). Cartridge (28) may also include a movable retainer (not shown) for storage between anvil (26) and tissue contacting surface (34) prior to and/or after use in order to inhibit unintended contact with various portions of cartridge (28).

As shown in FIGS. 4-6, cartridge (28) includes a staple driver assembly (140) within cartridge housing (132) and proximally positioned behind the plurality of staples (not shown) within staple-containing slots (136). Driver assembly (140) of the present example is formed as a unitary structure of a plurality of staple drivers (141). Thus, the term "assembly" is not intended to be limited to an assembly of individual components, but may also include integrally formed components with unitary structures. Driver assembly (140) is configured to push the staples (not shown) respectively out of staple containing slots (136) and toward anvil (26) for formation. A knife holder (142) is disposed immediately proximal of driver assembly (140) in cartridge housing (132) and defines a slot (144) and ledge (146) for interaction with a knife retractor hook (148) (see FIG. 10B), which is discussed below in greater detail. Knife holder (142) is attached to knife (32) such that knife (32) extends distally from knife holder (142) through a slot (150) in driver assembly (140) and through another slot (152) in cartridge housing (132). Although knife (32) is disclosed as being within cartridge housing (132) in the present example, other configurations may also be used. For example, it will be appreciated that cartridge (28) may alternatively not include knife (32) for alternative treatments.

Knife holder (142) has a detent post (154) that extends through a slot (155) in cartridge housing (132). Detent post (154) is positioned in order to contact a detent protrusion (156) of cartridge slot (155) during the longitudinal travel of knife (132) and knife holder (142). Similarly, driver assembly (140) has a detent post (158) positioned in order to contact proximal and distal detent protrusions (159, 160) of cartridge slot (155).

Knife (32) and slots (150, 152) are positioned such that there is at least one row of staples (not shown) on either side of knife (132). In some versions, two rows of staple slots (136) containing respective rows of staples (not shown) are provided on each side of slot (152) of cartridge housing (132).

Cartridge housing (132) defines two longitudinally extending, generally circular holes (162, 164) at respective ends of knife slot (152). More particularly, hole (162) at a lower portion of cartridge housing (132) is shaped and dimensioned to receive a guide pin (166) through cartridge housing (132). Hole (164) at an upper portion of cartridge housing (132) is shaped and dimensioned to slidably receive retaining pin (30) through cartridge housing (132). Staple slots (136) of the present example are arranged such that the staples (not shown) laterally extend past the generally circular holes (162, 164).

Anvil (26) of the present example includes a plastic cutting washer (168) and a metallic staple-forming surface (138). Anvil (26) is disposed to maintain staple-forming surface (138) in alignment with the staples (not shown) to receive and form the staples (not shown) thereon. Retaining pin (30) is connected to a couplet (170) by a circumferential slot (172) in retaining pin (30) and a groove (not shown) in couplet (170). Couplet (170) is disposed within an arm (176) of cartridge housing (132) and is secured to arm (176) by an end cap (178).

Guide pin (166) and retaining pin (30) include respective slots (180, 182) (see also FIGS. 8-9) into which lower and upper ends (184, 186) of knife (32) are slidably disposed. A proximal end (188) of guide pin (166) is connected to anvil (26), whereas a distal end (190) of guide pin (166) extends from cartridge housing (132) and extends through a slot (192) in anvil (26). Cutting washer (168) slips onto anvil (26) via groove (194). Thereby, cutting washer (168) is configured to trap guide pin (166) in the opening formed by slot (192) in anvil (26) and a cutting surface (157) of anvil (26) for connecting anvil (26) to cartridge housing (132).

Figure 7A:
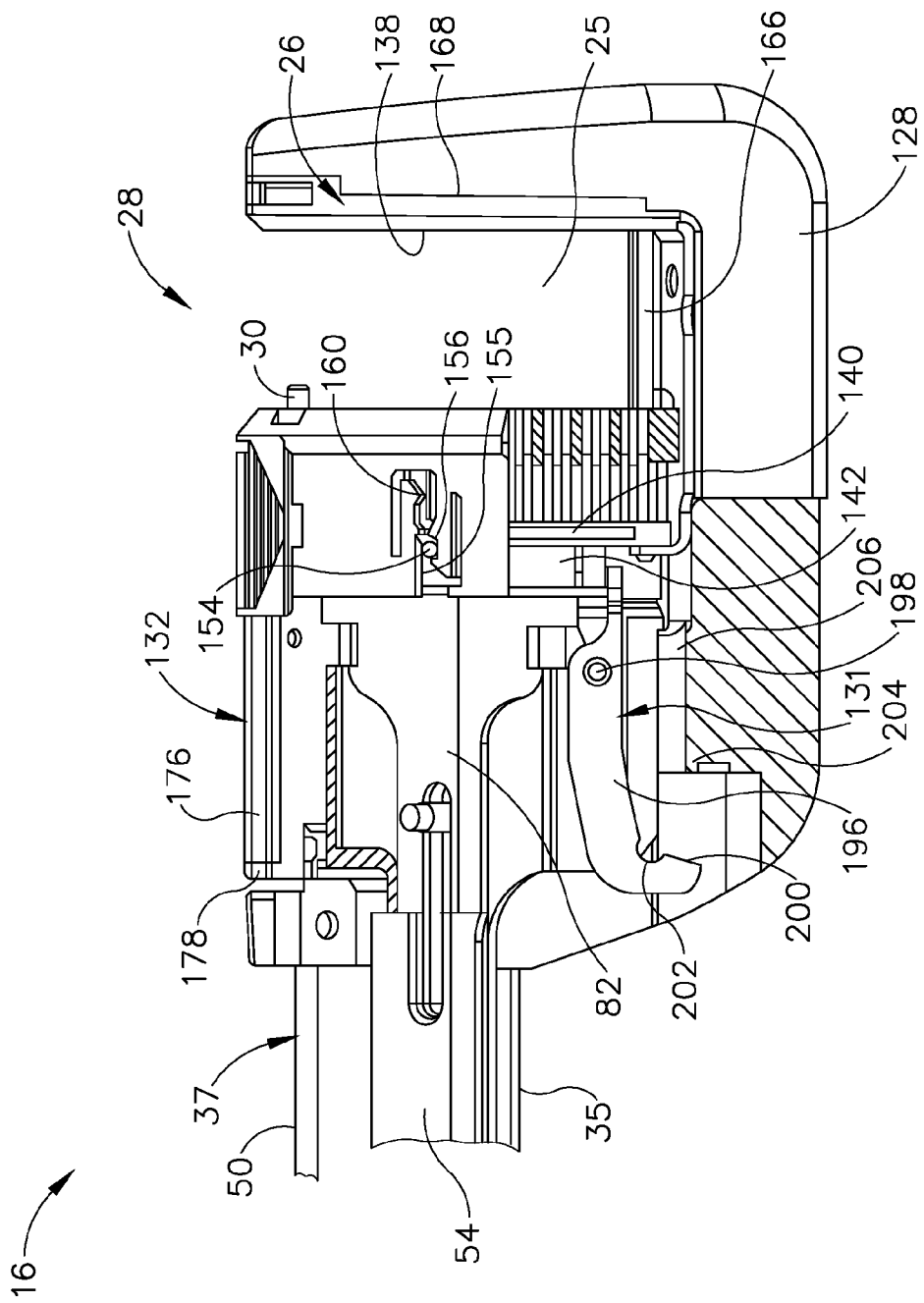
FIG. 7A depicts a left side view of the end effector of FIG. 1A with various components removed for clarity.

Lockout mechanism (131) is shown in FIG. 7A in greater detail. Lockout mechanism (131) is configured to inhibit full proximal movement of cartridge housing (132) to its unactuated position after firing. To this end, lockout mechanism (131) of the present example includes a lockout lever (196) that is pivotally mounted to the distal end of closure member (54) by a pin (198). Lockout lever (196) is spring biased toward the proximal end portion of supporting structure (128) by a spring (not shown). A proximal end portion of lockout lever (196) has a cam surface (200) and a locking groove (202). Supporting structure (128) of end effector (16) also has a ledge (204) that is configured to cooperate with locking groove (202) when lockout mechanism (131) is engaged. In contrast, supporting structure (128) has a base surface (206) configured to cooperate with cam surface (200) when lockout lever (131) is not engaged.

C. Exemplary Actuation of Cartridge

In the present example, cartridge (28) is driven toward anvil (26) via closure member (54) until reaching the closed configuration with tissue positioned between cartridge (28) and anvil (26) as discussed above with respect to handle assembly (12). From the closed configuration, knife (32) and staple driver assembly (140) are further moved toward anvil (26) via firing bar (82) to form staples (not shown) in the tissue, fluidly seal the tissue, and sever the tissue for treating the patient. While actuation of cartridge (28) includes stapling and severing tissue in this example, it will be appreciated that one or more of these steps may be omitted from treatment as desired by the operator. Moreover, it will be appreciated that surgical stapling instrument (10) may be reconfigured to perform these steps simultaneously or sequentially as desired. For example, actuation of firing bar (82) causes driver assembly (140) and knife (32) to move distally toward anvil (26) in the present example. Alternatively, surgical stapling instrument (10) may be reconfigured to selectively fire one of staples (not shown) or knife (32), or selectively fire staples (not shown) and then knife (32), or vice versa. It should therefore be understood that the invention is not intended to be limited to the particular operation of surgical stapling instrument (10) or the associated treatment.

Figure 7B:
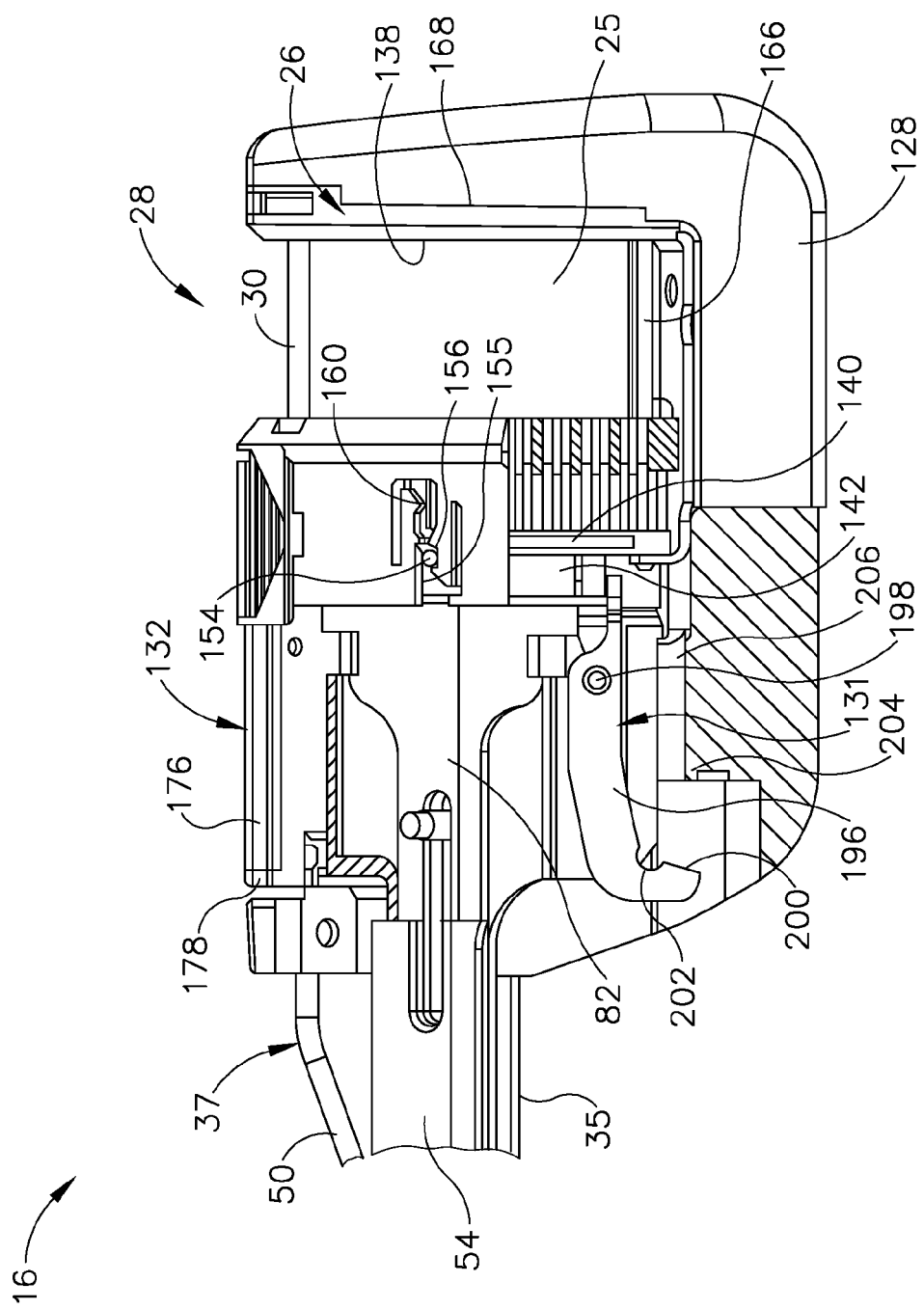
FIG. 7B depicts a left side view of the end effector of FIG. 1A with various components removed for clarity, and with the pin actuation mechanism in a closed position and the staple cartridge in the open position.

As shown in FIG. 7A, cartridge (28) is spaced proximally from anvil (26) to receive tissue within gap (25) in the open configuration. With tissue received between cartridge (28) and anvil (26), the operator manually directs push rod (50) distally via slide (18) as discussed above and shown in FIG. 7B. Push rod (50) is operatively connected to couplet (70) (see FIG. 6), which is connected to retaining pin (30). Thus, distally translating push rod (50) similarly translates retaining pin (30) to extend from cartridge (28) to anvil (26) and capture tissue between retaining pin (30) and guide pin (166).

Figure 7C:
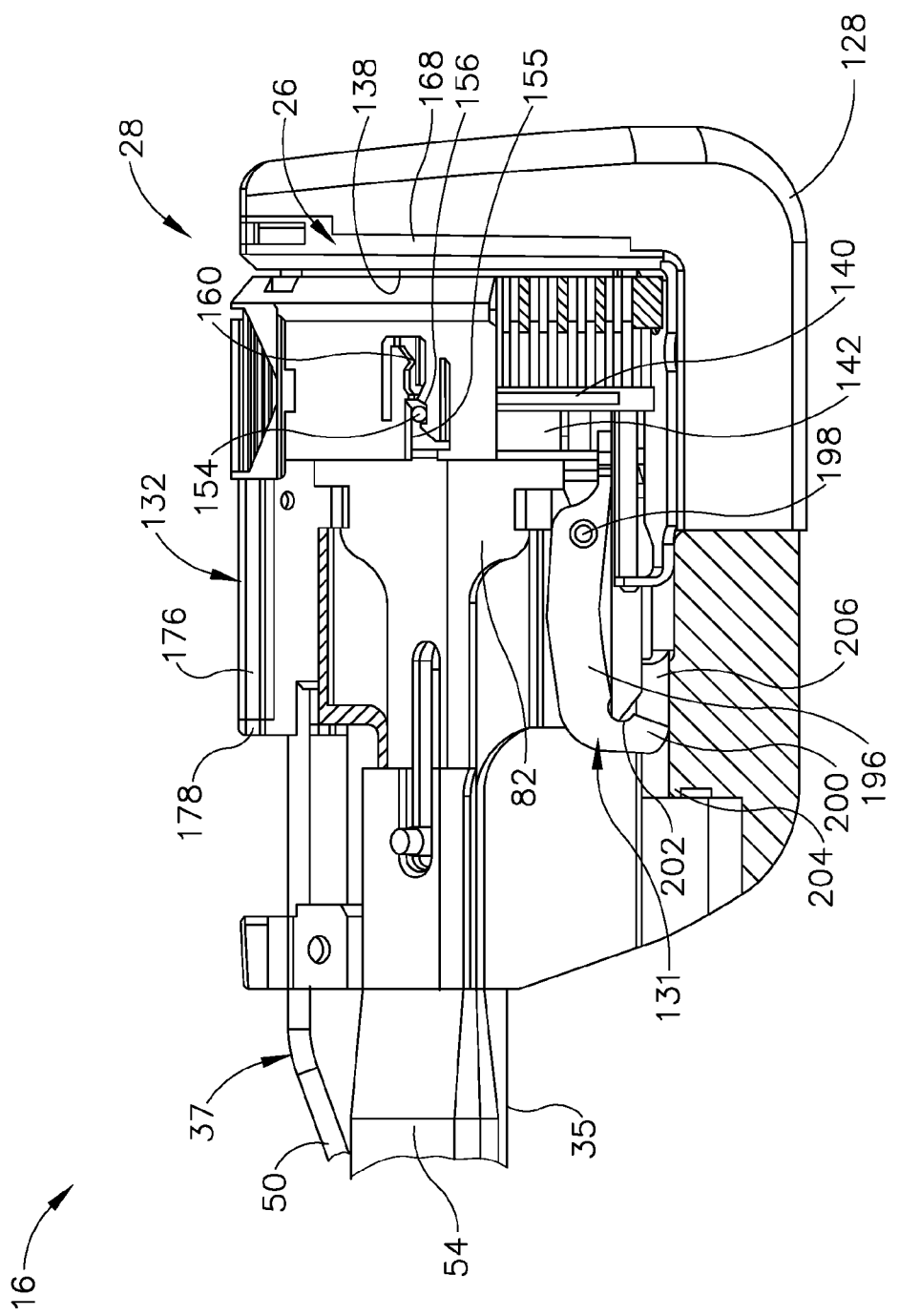
FIG. 7C depicts a left side view of the end effector of FIG. 1A with various components removed for clarity, and with the pin actuation mechanism in the closed position and the staple cartridge in the closed position via actuation of the closure mechanism.
Figure 7D:
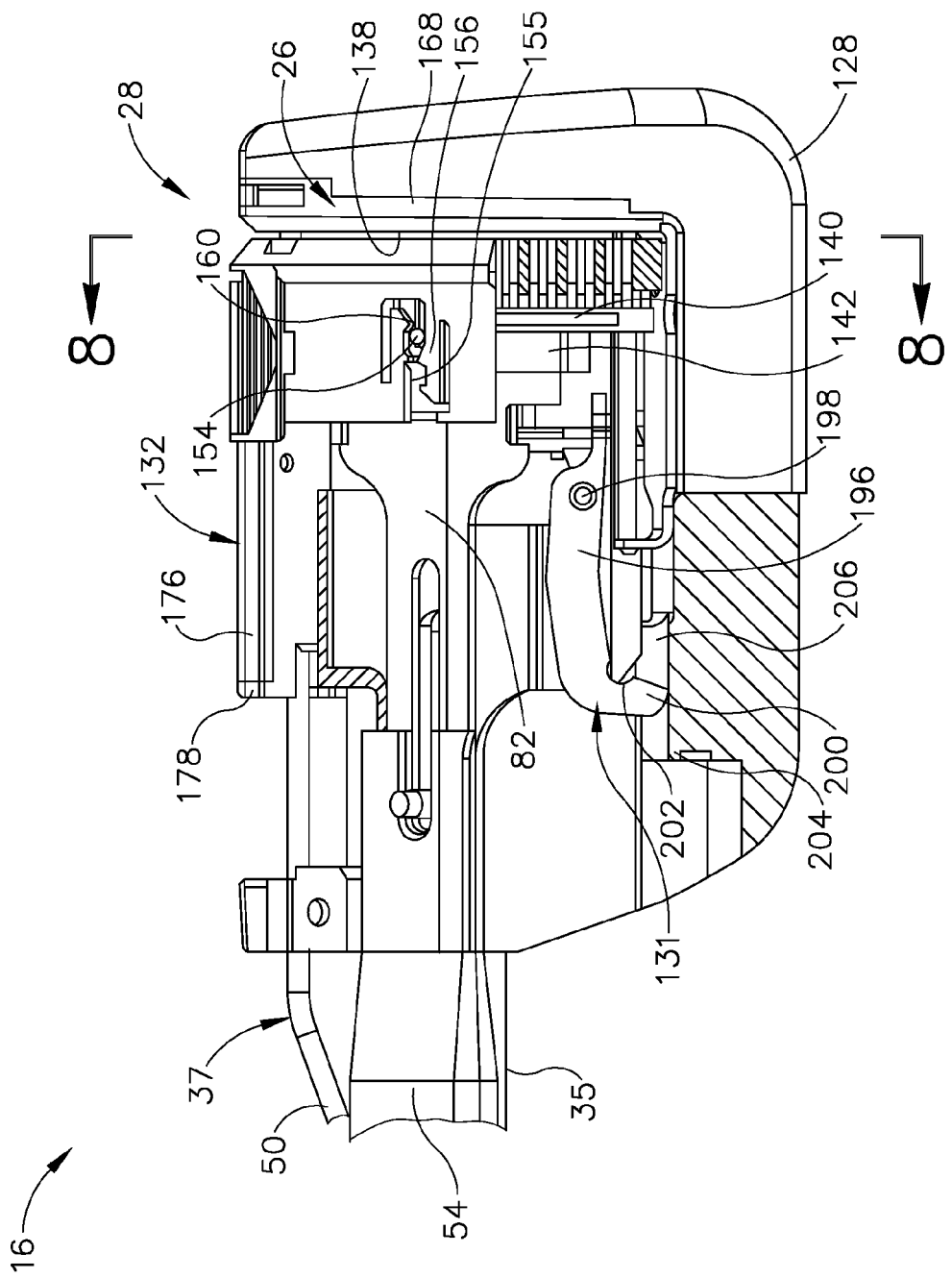
FIG. 7D depicts a left side view of the end effector of FIG. 1A with various components removed for clarity, and with the pin actuation mechanism and the staple cartridge in the closed positions and the firing trigger in the fired position for stapling and cutting tissue of a patient.
Figure 8:
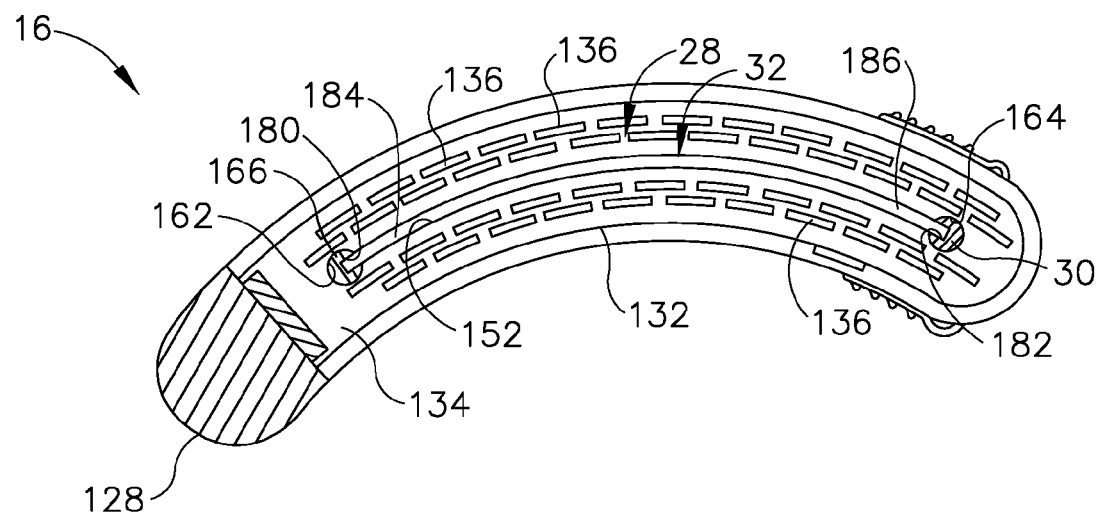
FIG. 8 depicts a cross-sectional view of the end effector of FIG. 7D, taken along section line 8-8 of FIG. 7D.
Figure 9:
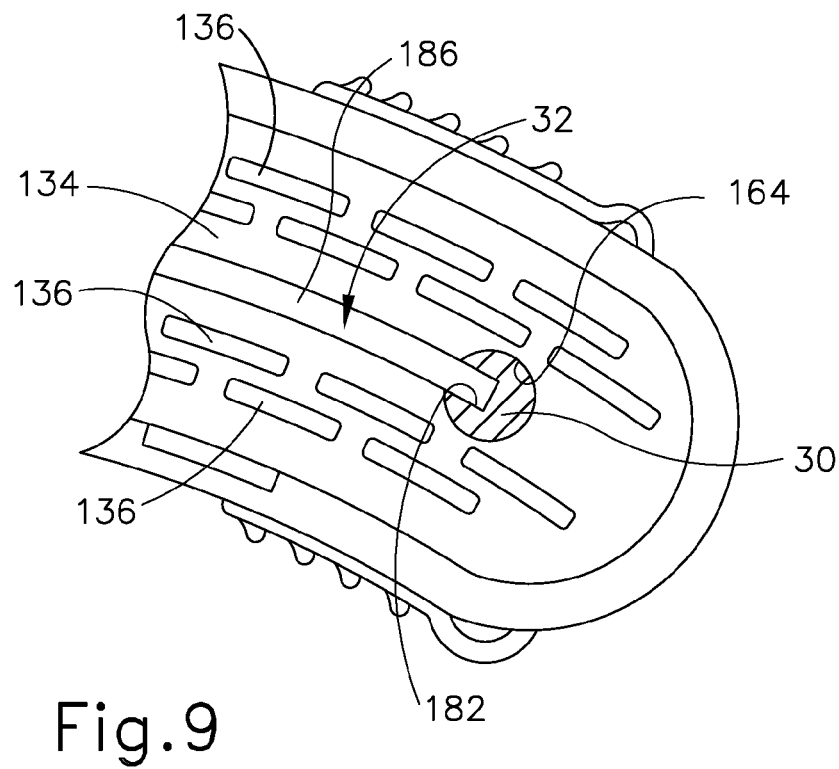
FIG. 9 depicts an enlarged cross-sectional view of a portion of the end effector of FIG. 8.

As shown in FIG. 7C, manipulation of closure trigger (20) (see FIG. 1C) forces closure member (54) to translate distally relative to supporting structure (128) of end effector (16). Closure member (54) supports cartridge (28) thereon such that distal translation of closure member (54) similarly moves firing bar (82) and cartridge (28) toward anvil (26). With cartridge (28) in the closed configuration and the tissue effectively captured in the end effector (16), the operator manipulates firing trigger (22) (see FIG. 1D) toward anvil (26) to the fired position. Distal translation of firing bar (82) causes firing bar (82) to engage knife holder (142), which supports both driver assembly (140) and knife (32) extending through driver assembly (140) as shown in FIG. 7D. In turn, driver assembly (140) directs staples (not shown) from staple slots (136) and against staple-forming surface (138) to form the staples (not shown) within the tissue for fluidly sealing the tissue. As the staples (not shown) are formed, knife (32) continues to translate distally through tissue and into anvil (26) to sever the fluidly sealed tissue. FIGS. 8-9 illustrate the fired cartridge (28) in greater detail, with knife (32) guided along cartridge housing slot (152), guide pin slot (180); and with retaining pin slot (182) between rows of staple slots (136) toward anvil (26).

Figure 10A:
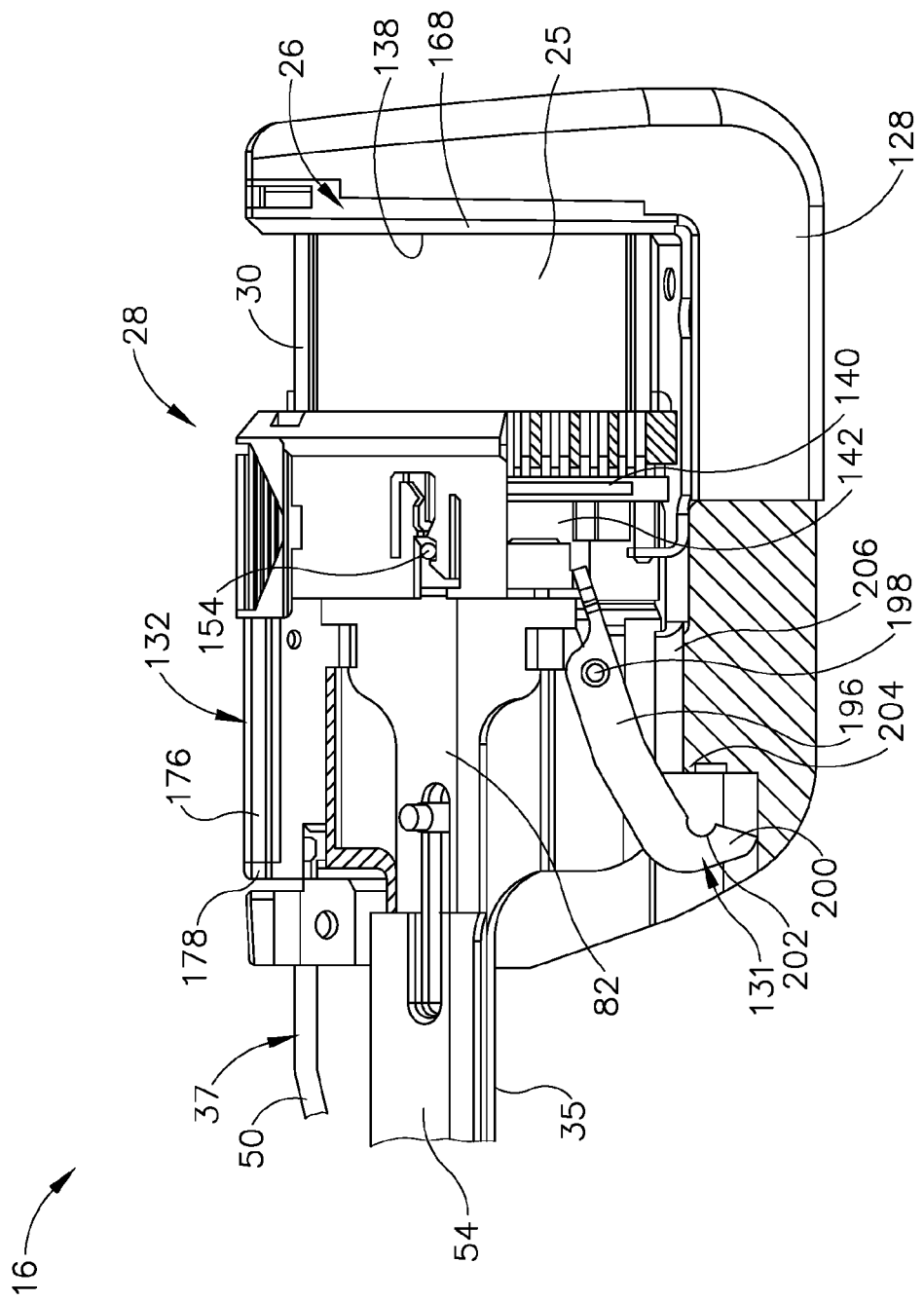
FIG. 10A depicts a left side view of the end effector of FIG. 1A, with various components removed for clarity, with the staple cartridge returned to the open position after actuating the firing trigger.

Once fired, the operator may depress release button (24) (see FIG. 2C) and withdraw closure member (54) and firing bar (82) proximally from the actuated, fired position to the unactuated position shown in FIGS. 10A-10B. More particularly, retractor hook (148) engages knife holder (142) to pull knife (32) proximally. At approximately the same time, as cartridge (28) translates proximally with closure member (54), lockout lever (196) of lockout mechanism (131) engages cartridge housing (132) to hold cartridge housing (132) in position. Thereby, the continued pull of knife (32) retracts knife (32) within cartridge housing (132) to inhibit unintended contact by operator with knife (32). Cartridge (28) may then be removed from supporting structure (128) of end effector (16), discarded, and replaced for further treatment if so desired. Of course, various suitable settings and procedures in which surgical stapling instrument (10) may be used will be apparent to those of ordinary skill in the art in view of the teachings herein.

It should also be understood that any other components or features of surgical stapling instrument (10) may be configured and operable in accordance with any of the various references cited herein. Additional exemplary modifications that may be provided for surgical stapling instrument (10) will be described in greater detail below. Various suitable ways in which the below teachings may be incorporated into surgical stapling instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to surgical stapling instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

Figure 14:
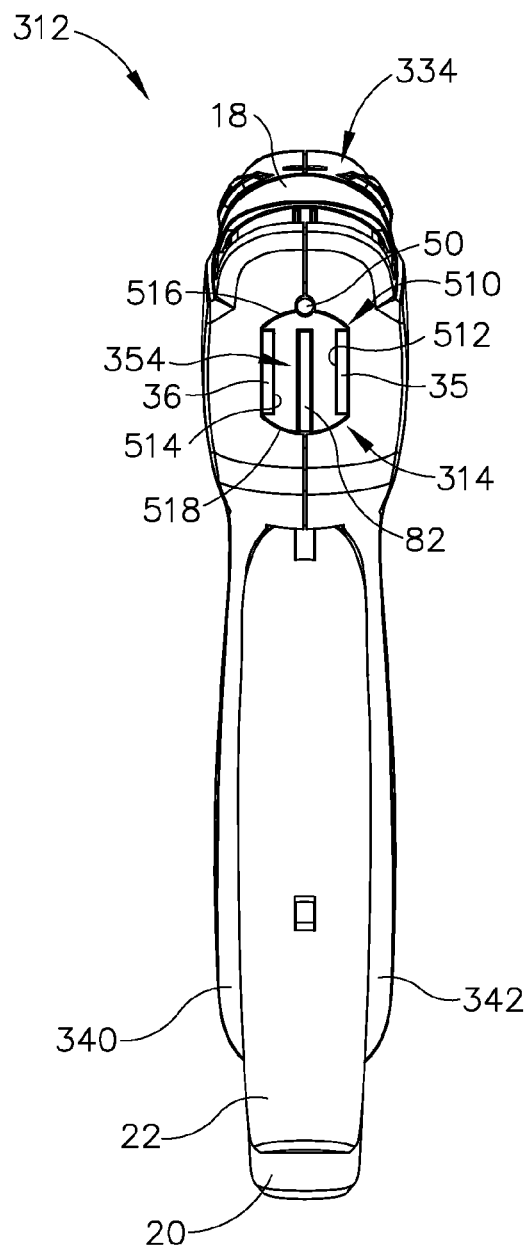
FIG. 14 depicts a cross-sectional end view of another exemplary surgical stapling instrument.
Figure 15:
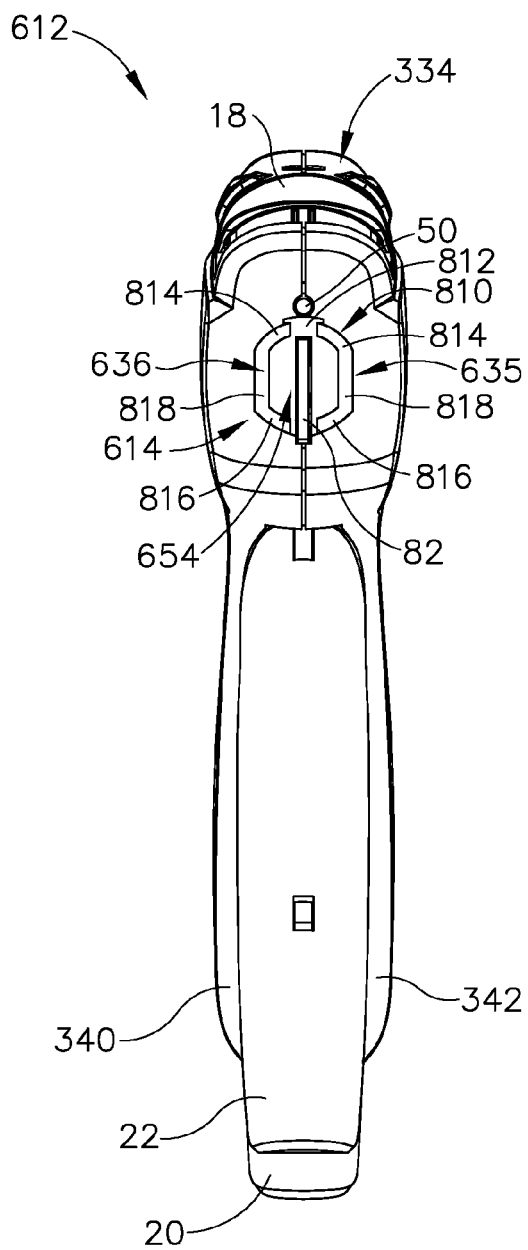
FIG. 15 depicts a cross-sectional end view of another exemplary surgical stapling instrument.

II. Exemplary Surgical Stapling Instruments with Alternative Handle and Shaft Assemblies While the above surgical stapling instrument (10) provides one example of handle assembly (12) having shaft assembly (14) projecting distally therefrom, it will be appreciated that the operator may desire an alternative handle assembly and/or shaft that may be used with end effector (16) or another, alternative end effector depending on one of a variety particular treatments. For example, as the operator manipulates handle assembly (12) such that end effector (16) accesses the tissue within the patient, shaft assembly (14) may also contact the surrounding tissue within the patient. While some tissues may be capable of sustaining contact with shaft assembly (14) without injury, other, more sensitive tissues, may be damaged by contact with shaft assembly (14), particularly in the event that shaft assembly (14) is relatively sharp and rigid in one or more regions. It may therefore be desirable to provide a surgical stapling instrument (310) with a shaft assembly (314, 614) having a relatively rounded outer profile to reduce the likelihood that tissue contact with shaft assembly (314, 614) may inadvertently damage surrounding tissue. The outer profiles of shaft assemblies (314, 614) are best seen in FIGS. 14-15.

Shaft assemblies (314, 614) and handle assemblies (312, 612, 912) are described below in the context of a proctocolectomy surgical procedure. While the following description of shaft and handle assemblies (314, 614, 312, 612, 912) and method of treatment is provided in the context of stapling and/or cutting colon tissue, it will be appreciated that surgical stapling instrument (310) and any of shaft and handle assemblies (314, 614, 312, 612, 912) may be alternatively configured to treat any tissue in the human body with similar features. It should also be understood that the features discussed below may be readily incorporated into surgical stapling instrument (10) discussed above. To this end, like numbers indicate like features described above in greater detail.

Figure 11:
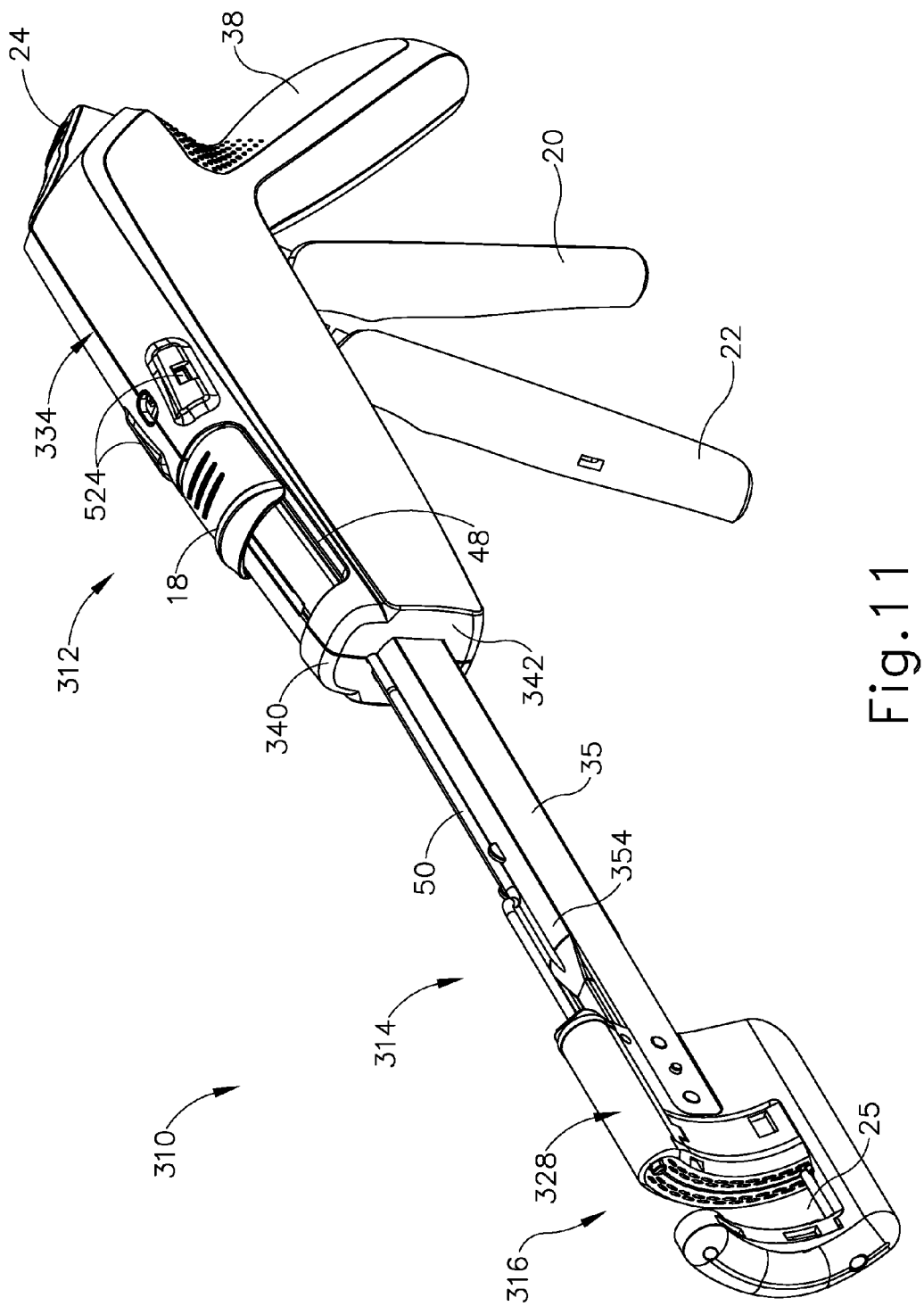
FIG. 11 depicts a right perspective view of another exemplary surgical stapling instrument.
Figure 12:
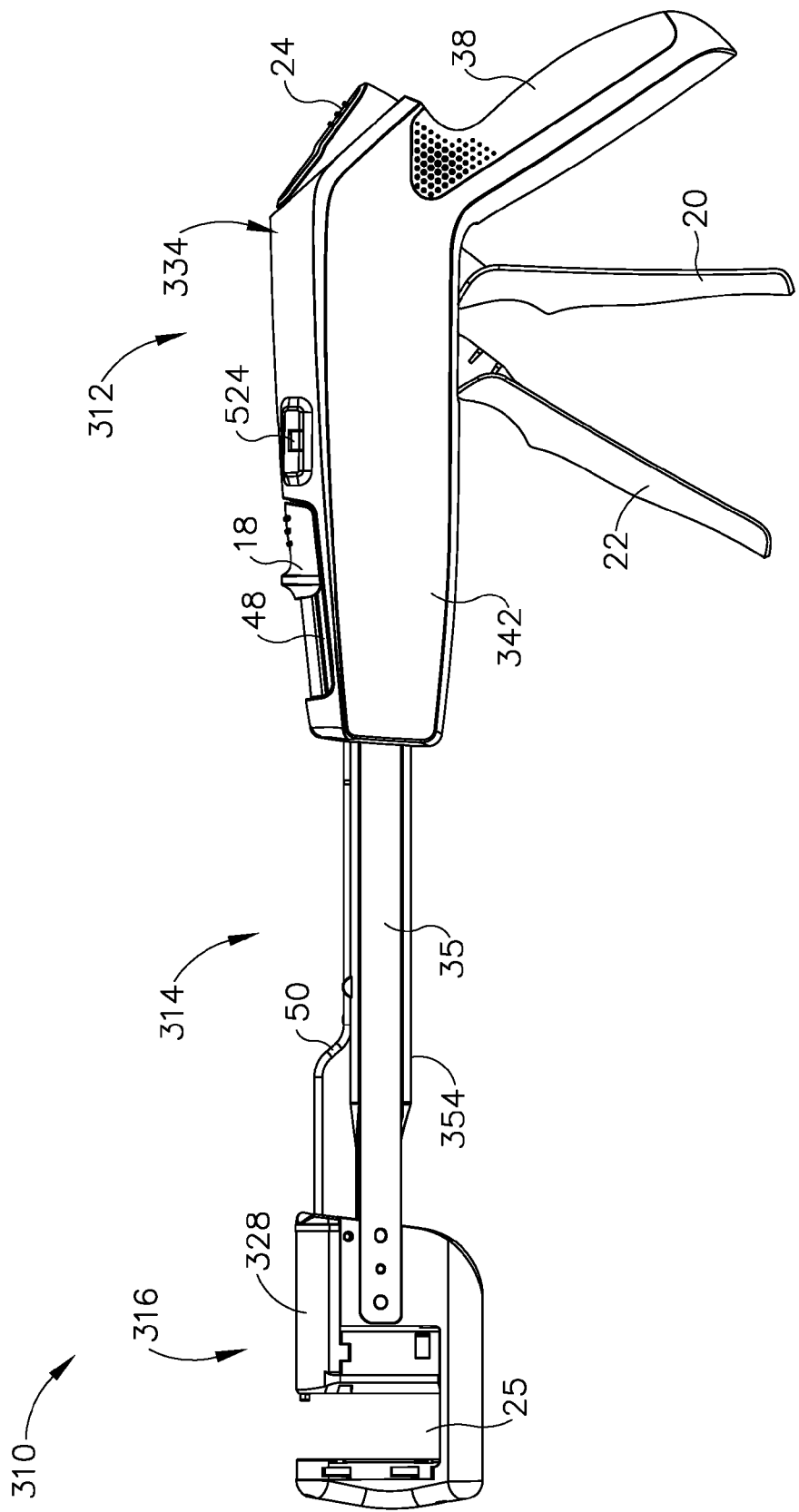
FIG. 12 depicts a right side view of the surgical stapling instrument of FIG. 11.
Figure 13:
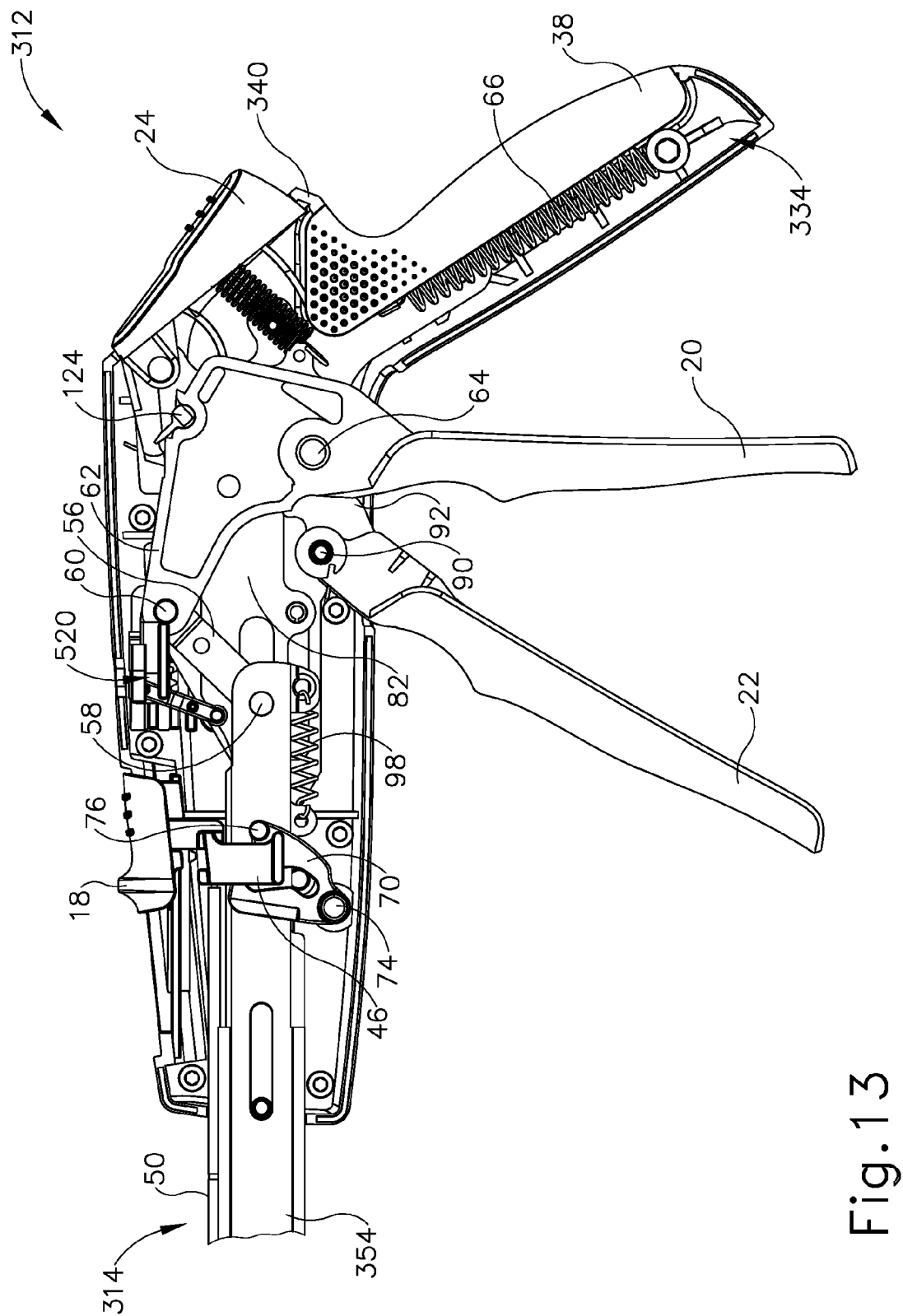
FIG. 13 depicts a right side view of a handle assembly of the surgical stapling instrument of FIG. 12, with various components removed for clarity.

A. Exemplary Surgical Stapling Instrument Having Shaft Assembly with a Rounded Outer Profile FIGS. 11-13 show surgical stapling instrument (310) with handle assembly (312) and shaft assembly (314) extending distally from handle assembly (312). An end effector (316) extends distally from shaft assembly (314) and is configured to fluidly seal and sever tissue with staples (not shown) and knife (32) (see FIG. 6) similar to end effector (16) discussed above in greater detail. To this end, the operator squeezes closure trigger (20) to selectively translate a closure member (354) distally to the closed configuration with tissue captured therein. The operator further squeezes firing trigger (22) to selectively translate firing staples (not shown) and knife (32) (see FIG. 6) from a cartridge (328).

1. Exemplary Shaft Assembly with Rounded Closure Member

FIGS. 12-14 and 17 show shaft assembly (314) in greater detail. Shaft assembly (314) defines a rounded outer profile (510) that is generally continuous about shaft assembly (314) and is thereby configured to avoid damaging tissue upon contact with tissue during use of instrument (310) in a surgical procedure. Rounded outer profile (510) is more particularly defined collectively by left and right handle frame plates (35, 36), closure member (354), firing bar (82), and push rod (50) extending along an upper portion of closure member (354). Closure member (354) has a pair of lateral slots (512, 514) extending longitudinally therealong that are configured to receive handle frame plates (35, 36), respectively. In addition, closure member (354) has an upper rounded surface (516) and an opposing lower rounded surface (518), whereas handle frame plates (35, 36) are generally planar so as to be received within respectively lateral slots (512, 514). Frame plates (35, 36) are thereby flush with the surrounding upper and lower rounded surfaces (516, 518) so as to be free of sharp or abrasive edges that may damage tissue. Rounded outer profile (510) thus has rounded upper and lower portions that may pass along tissue atraumatically. However, it will be appreciated that alternative shaft assemblies with alternative rounded outer profiles may be constructed for inhibiting such tissue damage.

2. Exemplary Shaft Assembly with Rounded Handle Frame Plates

Figure 16:
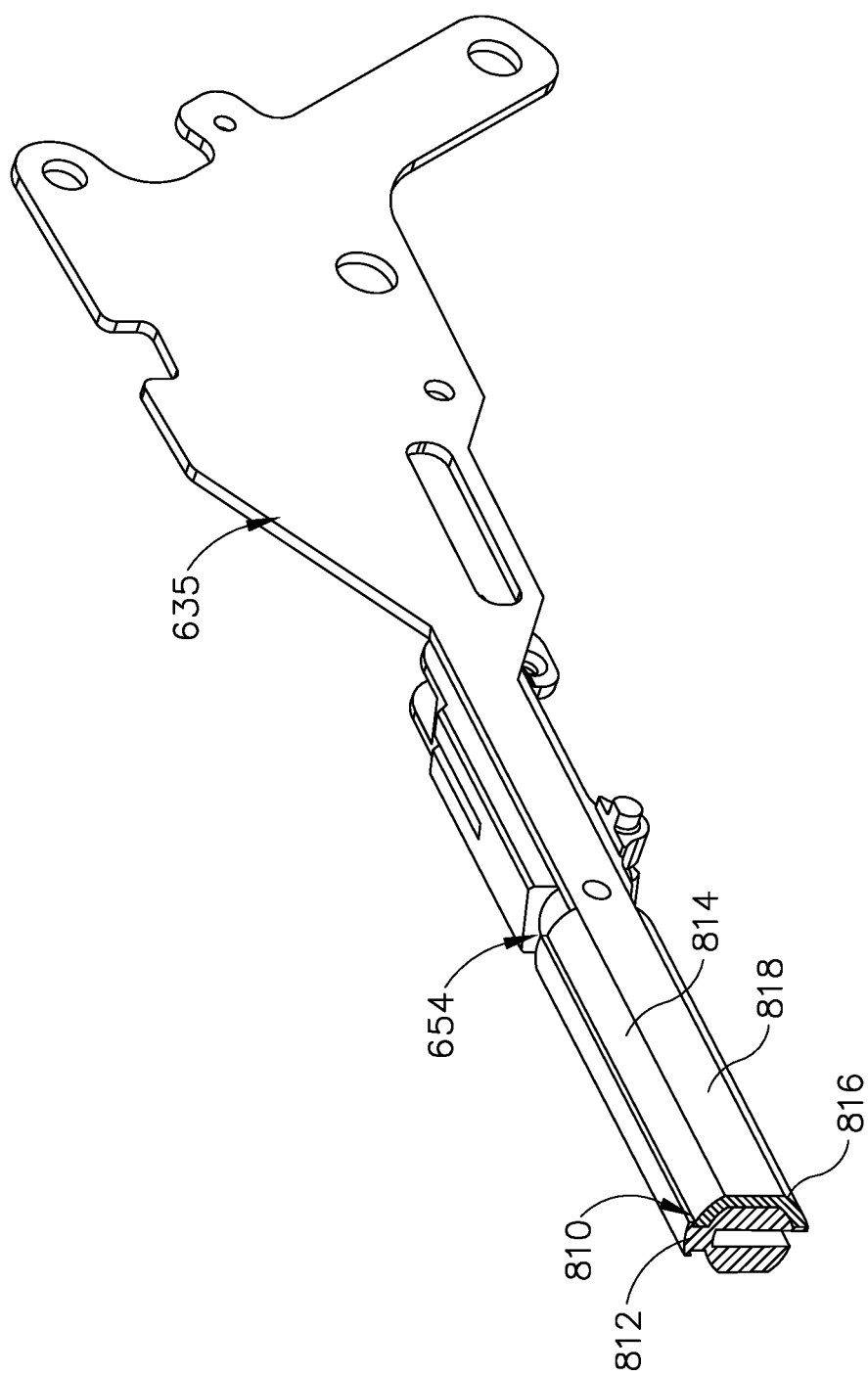
FIG. 16 depicts a right front sectional perspective view of a portion of the shaft assembly of the surgical stapling instrument of FIG. 15.
Figure 17:
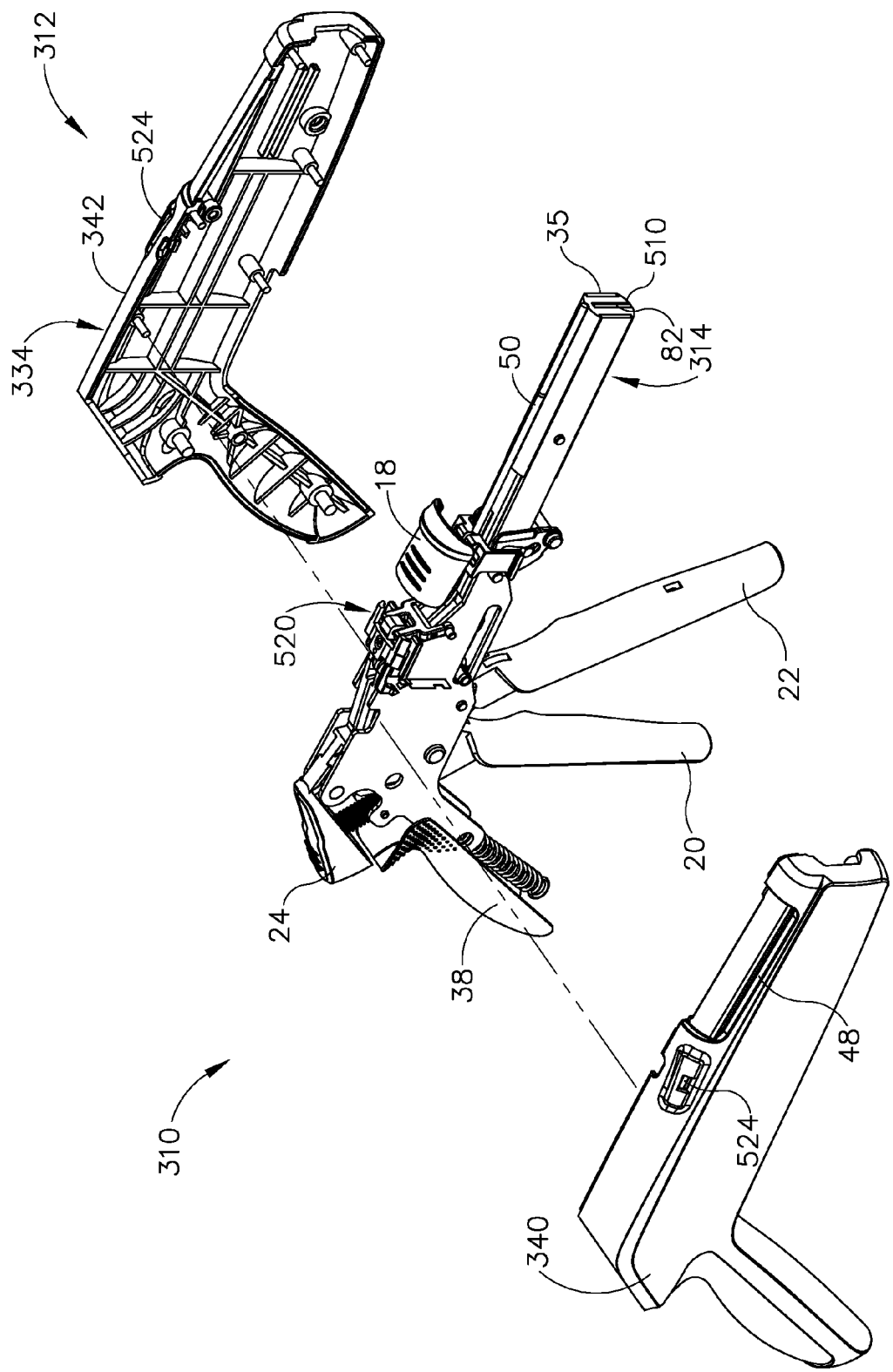
FIG. 17 depicts a partially exploded left front perspective view of a handle assembly of the surgical stapling instrument of FIG. 11, with a left shroud portion and a right shroud portion separated from other components of the handle assembly.

Another exemplary shaft assembly (614) is also configured to avoid damaging tissue via an alternative rounded outer profile (810) shown in FIGS. 15-16. Rounded outer profile (810) is collectively defined by left and right rounded frame plates (635, 636), a closure member (654), firing bar (82), and push rod (50) extending along an upper portion of closure member (654). Closure member (654) includes an upper cap (812) extending upwardly therefrom. In addition, rounded frame plates (635, 636) each have rounded upper and lower portions (814, 816) with a planar intermediate portion (818) extending therebetween to define a generally C-shape. Rounded upper portions (814) of each rounded frame plate (635, 636) are positioned partially under upper cap (812) to be generally flush with upper cap (812). The planar intermediate portions (818) and lower rounded portions (816) of each rounded frame plate (635, 636) cradle opposing lateral sides of closure member (654) such that closure member (654) is generally surrounded by rounded frame plates (635, 636) on each lateral side. Rounded outer profile (810) thus has rounded upper and lower portions that may pass along tissue during use with reduced abrasiveness that may otherwise damage the tissue.

III. Exemplary Surgical Stapling Instruments with Alternative End Effectors

While the above surgical stapling instrument (10) provides one example of end effector (16) projecting distally from handle assembly (12), it will be appreciated that the operator may desire an alternative end effector depending on one of a variety particular treatments. Various tissues may be more or less difficult to treat depending on size and/or density within the patient. Despite the operator properly positioning end effector (16) relative to tissue for accurately and precisely stapling and severing the tissue, thicker and/or denser tissues often require added force to be transmitted along surgical stapling instrument (10) and, in turn, may cause one or more components of instrument (10) to deform during use. For example, compressing a portion of the colon between anvil (26) and cartridge (28) in the closed configuration may deform supporting structure (128) of end effector (16), particularly as the tissue is stapled and severed. Thus, the particular location in which the staples form and the knife (32) cuts may vary or deviate a small, but relatively meaningful, amount that may negatively impact the effectiveness of the treatment. It may therefore be desirable to provide surgical stapling instrument (310) with end effector (316) having a supporting structure (328) that is configured to reduce deformation within end effector (316) during treatment. By way of example, end effector (316) may have supporting structure (448) configured to cooperate with retaining pin (330) for providing greater structural rigidity during use for reducing deformation within end effector (316); and further increasing the accuracy and precision of the treatment. It may be further desirable to provide an end effector (316, 616, 916, 1216, 1416, 1616) with one of a variety of retaining pins (330, 630, 930, 1230, 1430, 1630) shown and described herein.

End effectors (316, 616, 916, 1216, 1416, 1616) are described below in the context of a proctocolectomy surgical procedure. While the following description of end effectors (316, 616, 916, 1216, 1416, 1616) and methods of treatment is provided in the context of stapling and/or cutting colon tissue, it will be appreciated that surgical stapling instrument (310) and any of end effectors (316, 616, 916, 1216, 1416, 1616) may be alternatively configured to treat any tissue in the human body with similar features. It should also be understood that the features discussed below may be readily incorporated into surgical stapling instrument (10) discussed above. To this end, like numbers indicate like features described above in greater detail.

A. Exemplary Surgical Stapling Instrument with Lockable Retaining Pin Mechanism

Figure 18:
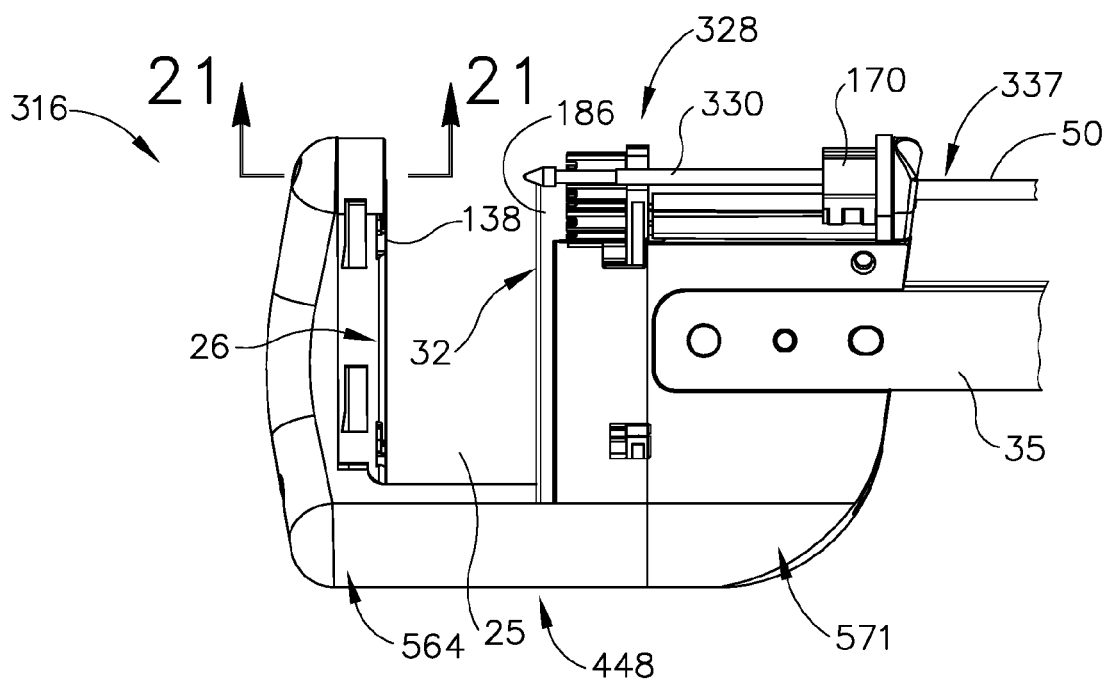
FIG. 18 depicts a right side view of an end effector of the surgical instrument FIG. 11 having various components removed for clarity.
Figure 19:
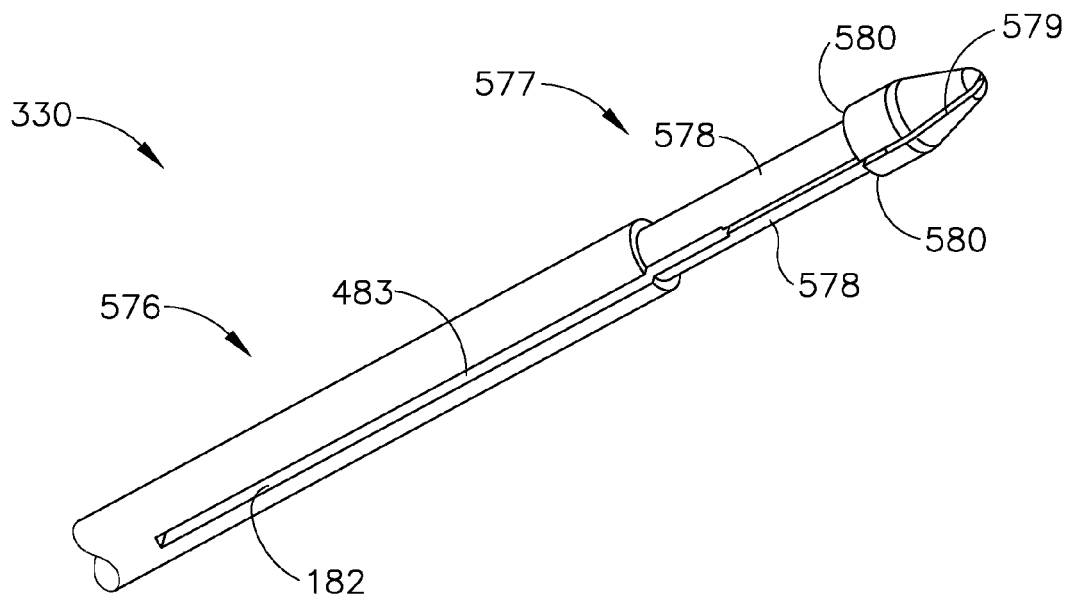
FIG. 19 depicts a lower perspective view of a retaining pin of the end effector of FIG. 18.
Figure 20:
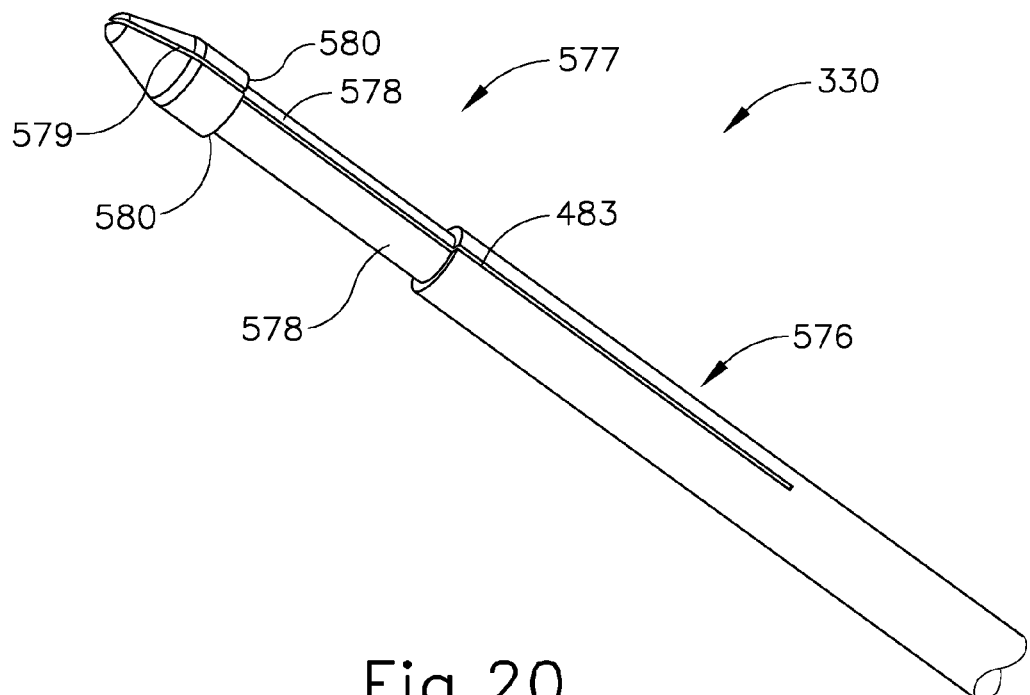
FIG. 20 depicts an upper perspective view of the retaining pin of FIG. 19.
Figure 21:
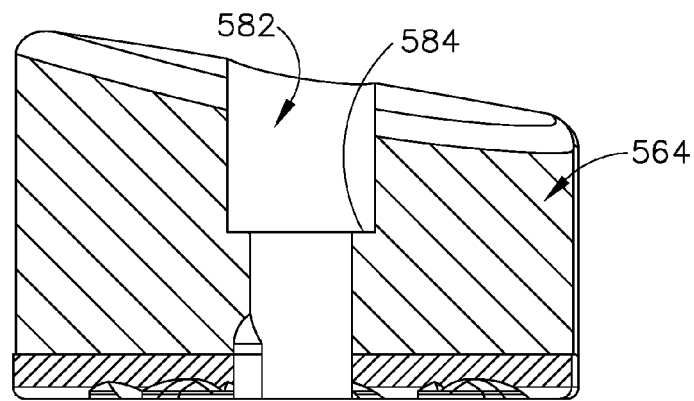
FIG. 21 depicts a cross-sectional view of the end effector of FIG. 18, taken along section line 21-21 of FIG. 18.
Figure 22:
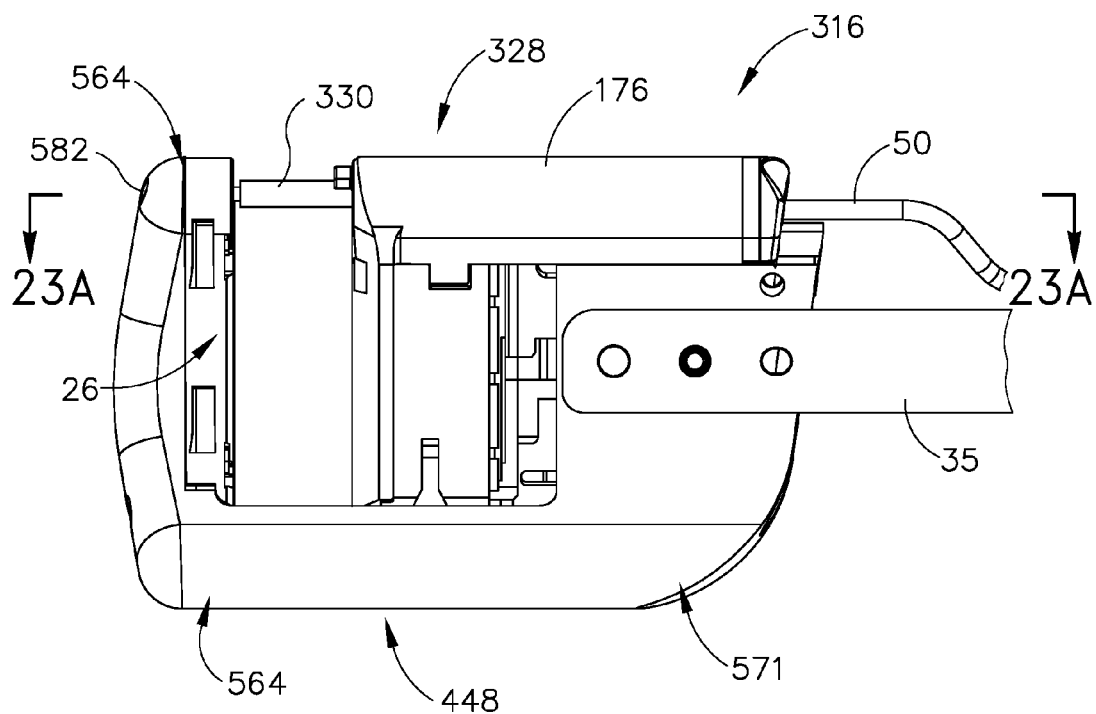
FIG. 22 depicts a right side view of the end effector of FIG. 18, with the retaining pin in an unlocked closed position.

A lock retaining pin (330) is configured to translate from an open position to a locked closed position as shown in FIGS. 18-23C. FIG. 18 shows end effector (316) with cartridge (328) loaded therein in the open configuration for receiving tissue within gap (25) as discussed above in greater detail. Cartridge (328) has a retaining pin mechanism (337), which includes lock retaining pin (330) connected to push rod (50) via couplet (170). Slide (18) (see FIG. 1A and FIG. 2A) selectively directs movement of push rod (50) distally from the open configuration to the closed configuration for capturing tissue, such as colon tissue for performing a lower anterior resection (LAR). To this end, lock retaining pin (330) is generally driven distally from within arm (176) of cartridge (328) to distal end portion (564) similar to retaining pin (30) discussed above in greater detail with respect to FIGS. 1A-1B and FIGS. 7A-7B. However, it will be appreciated that alternative mechanisms for moving lock retaining pin (330), such as by rotation and/or translation, may be used in accordance with principles discussed herein.

1. Exemplary Knife Lock Retaining Pin and Ledge Lock

Figure 23A:
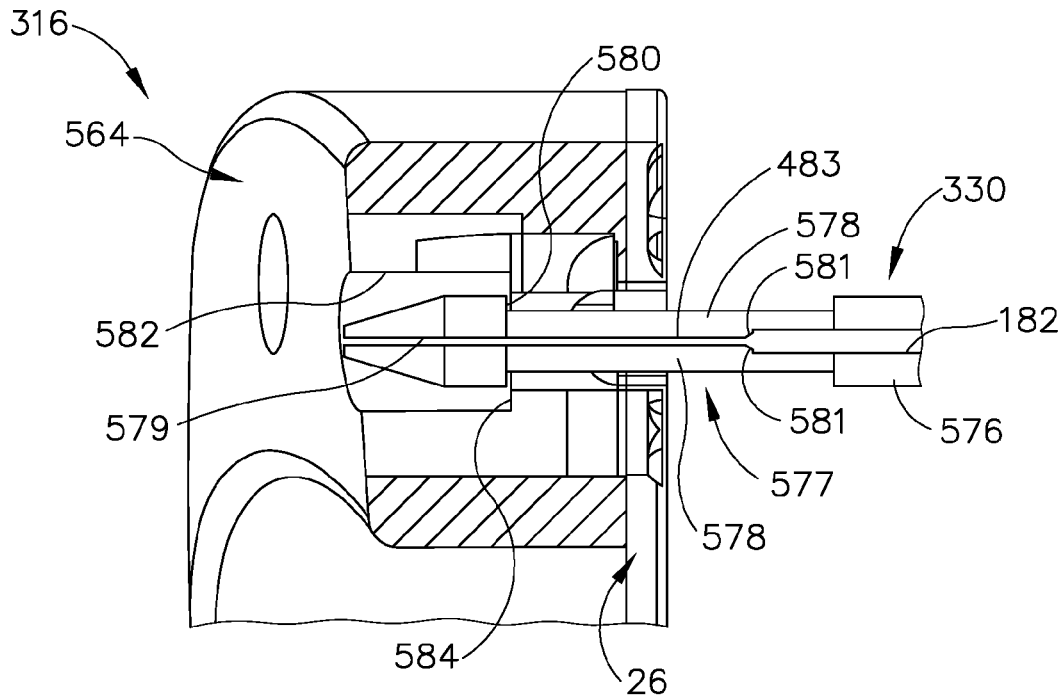
FIG. 23A depicts a cross-sectional view of a portion of the end effector of FIG. 18, with the retaining pin in the unlocked closed position of FIG. 22, taken along section line 23A-23A of FIG. 22.

Knife lock retaining pin (330) extends through arm (176) (see FIG. 6) of cartridge (328) in the open configuration shown in FIG. 18. Cartridge housing (132) (see FIG. 6) has been removed for clarity and improved visibility of knife lock retaining pin (330). With respect to FIGS. 18-20, knife lock retaining pin (330) includes longitudinally extending slot (182) through which knife lock retaining pin (330) receives and guides upper lateral end (186) of knife (32) between closed and open configurations. Slot (182) extends transversely through a portion of knife lock retaining pin (330) such that slot (182) does not extend entirely transversely therethrough. Knife lock retaining pin (330) further includes an expansion slot (483), generally thinner than slot (182), that extends longitudinally from an intermediate pin portion (576) of knife lock retaining pin (330) through a distal end portion (577) of knife lock retaining pin (330). Expansion slot (483) extends entirely transversely through knife retaining pin (330) in one example from intermediate pin portion (576) through distal end portion (577) in order to bisect distal end portion (577) into two resilient extensions (578). Each resilient extension (578) of distal end portion (577) is annularly recessed to define a distal head (579) having a proximal annular ledge (580). As shown in FIG. 23A, extension slot (483) longitudinally intersects slot (182) to define offset shoulders (581) within distal end portion (577) on each respective resilient extension (578). Knife (32) has a transverse depth (see FIG. 23B) greater than expansion slot (483) such that knife (32) moving distally through slot (182) is configured to engage shoulders (581) and wedge between resilient extensions (578) away from knife (32). Thereby distal head (483) resiliently expands from a contracted state to an expanded state With further respect to FIG. 23A, distal end portion (564) of end effector (316) includes a longitudinally extending retaining pin bore (582) that is configured to receive distal head (579) of knife lock retaining pin (330) in the contracted state. Retaining pin bore (582) has a distal portion with a larger diameter to define a distal annular ledge (584). Distal annular ledge (584) is sized such that the lower portion of retaining pin bore (582) is smaller in diameter than distal head (579) in the expanded state. Thus, in the expanded state, proximal annular ledge (580) of distal head (579) overlaps with distal annular ledge (584) within retaining pin bore (582) to inhibit deflection of distal end portion (564) of end effector (316) relative to knife lock retaining pin (330). In other words, expansion of distal head (579) within retaining pin bore (582) positions knife lock retaining pin (330) in the locked closed position.

Figure 23B:
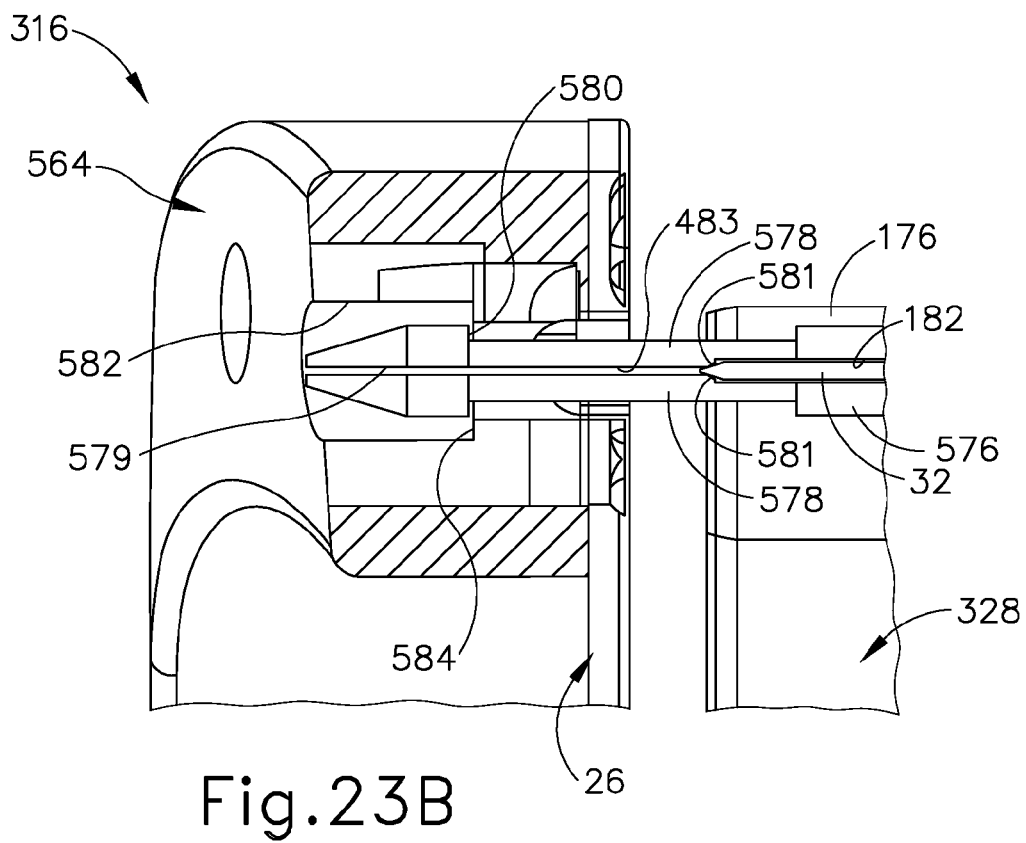
FIG. 23B depicts a cross-sectional view of a portion of the end effector of FIG. 18, with the staple cartridge moving toward the closed position.
Figure 23C:
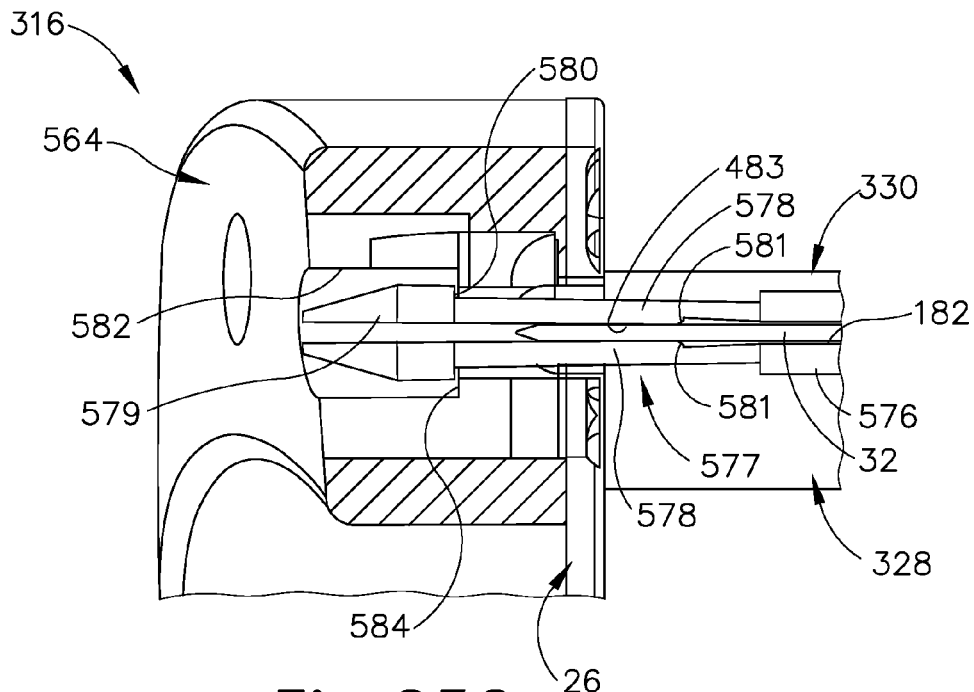
FIG. 23C depicts a cross-sectional view of a portion of the end effector of FIG. 18, with the retaining pin in a locked closed position.

FIGS. 23A-23C illustrate knife lock guide pin (330) locking from an unlocked closed position to the locked closed position. FIG. 23A shows knife lock guide pin (330) in the unlocked closed position following distal movement directed by slide (18) (see FIG. 1A and FIG. 2A) of retaining pin actuation mechanism (337). With tissue (not shown) captured between cartridge (328) and anvil (26), cartridge (328) and knife (32) contained therein are directed toward distal end portion (564) of end effector (316). Knife (32) continues distally such that knife (32) engages shoulders (581) to wedge between resilient extensions (578) and expand distal head (579) outwardly from the contracted state to the expanded state. Thereby, distal head (579) is effectively captured in distal portion of retaining pin bore (582) as shown in FIG. 23C. Distal annular ledge (584) of retaining pin bore (582) may then engage proximal annular ledge (580) of knife lock retaining pin (330) to inhibit deflection of distal end portion (564) of end effector (316) as cartridge (328) and tissue are compressed against anvil (26). While knife lock guide pin (330) is expanded via knife (32) in the present example and effectively braces distal end portion (564) in tension, it will be appreciated that alternative structures may expand alternative guide pins; or may otherwise lock with distal end portion (564) such that alternative guide pins may brace distal end portion (564) in compression, as well. To this end, the invention described herein is not intended to be unnecessarily limited to exemplary knife lock guide pin (330).

2. Exemplary Rod lock Retaining Pin and Ledge Lock

Figure 24:
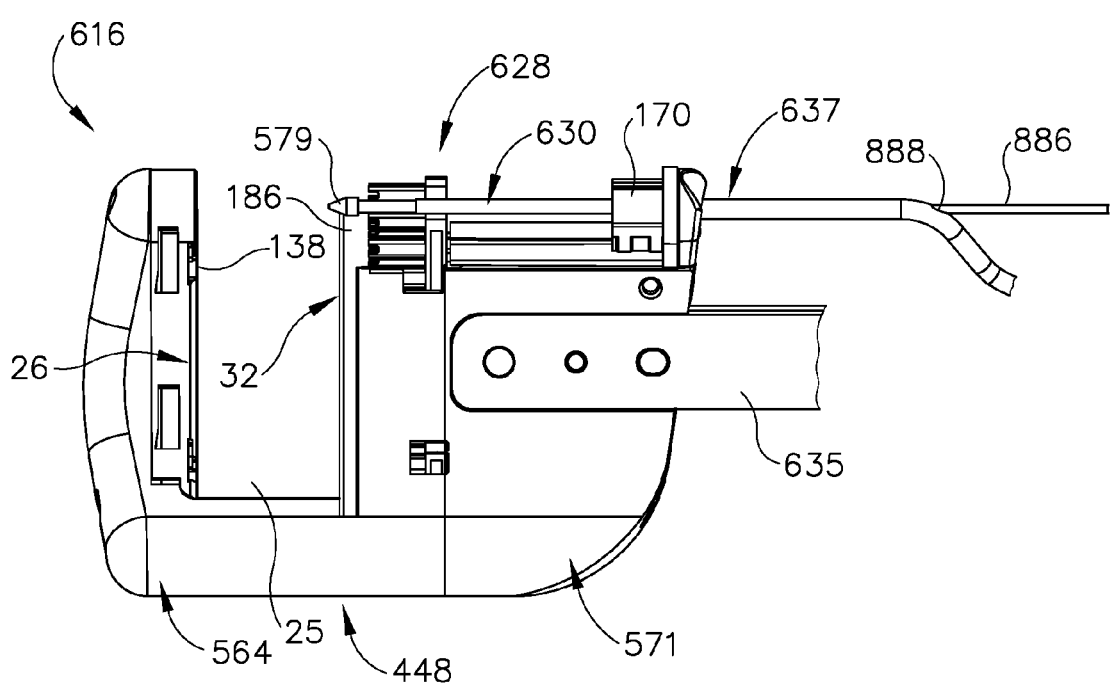
FIG. 24 depicts a right side view of another exemplary end effector having various components removed for clarity.
Figure 25:
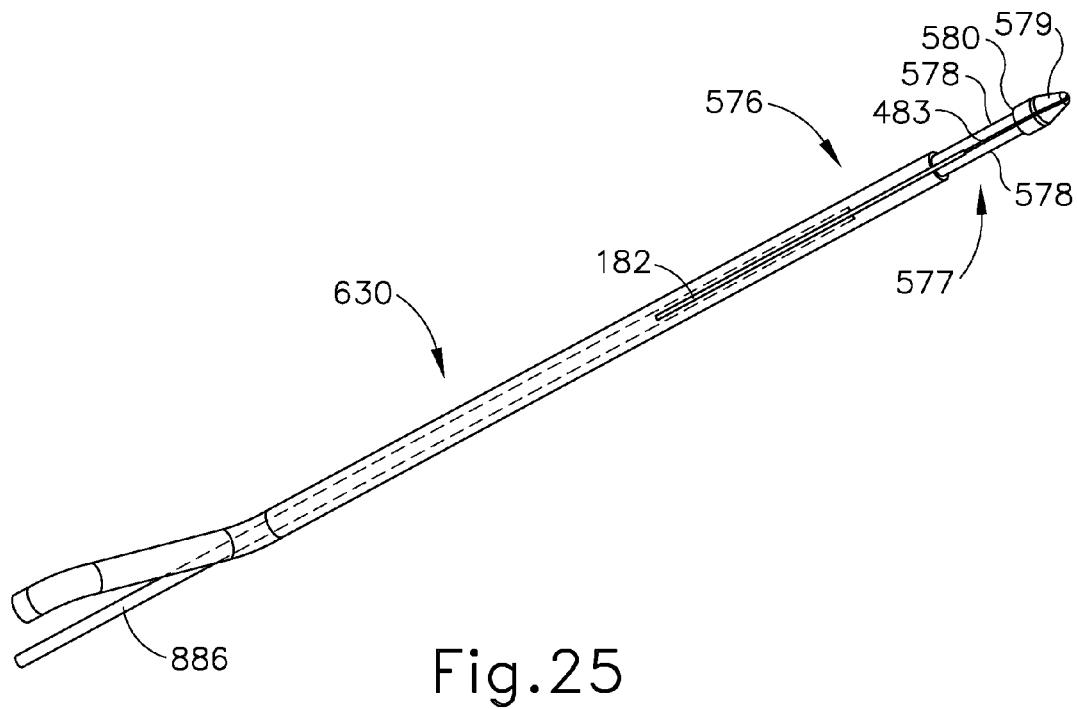
FIG. 25 depicts a lower perspective view of a retaining pin of the end effector of FIG. 24.
Figure 26:
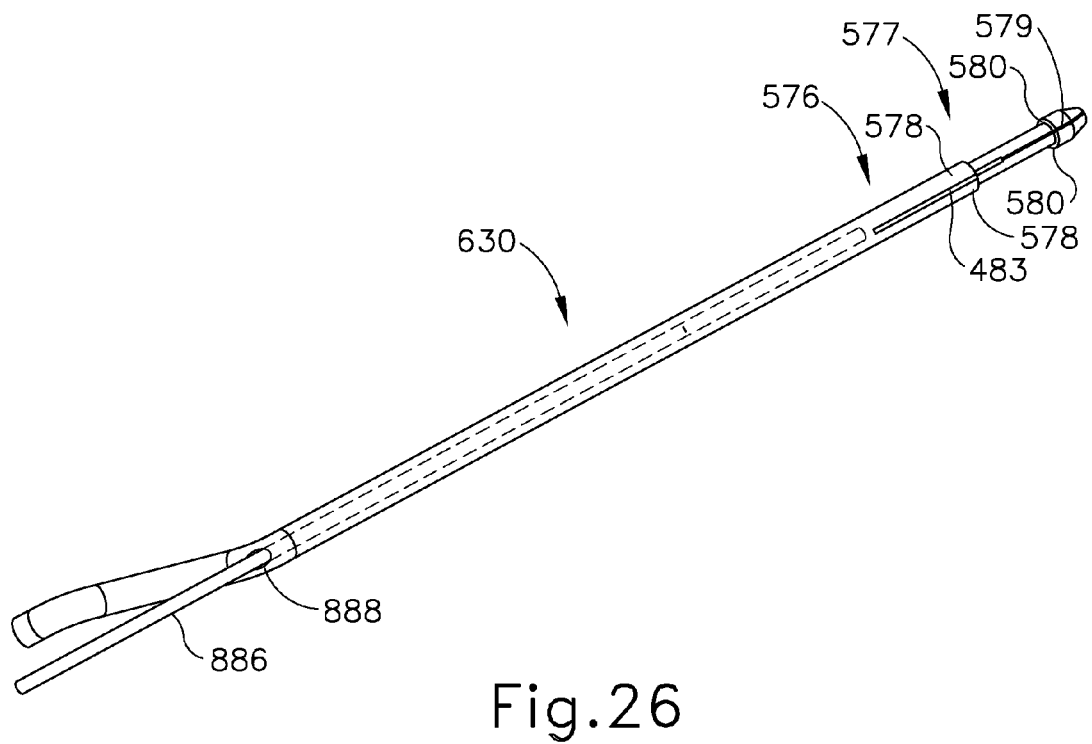
FIG. 26 depicts an upper perspective view of the retaining pin of FIG. 25.

FIG. 24 shows an exemplary alternative end effector (616), where a rod lock retaining pin (630) extends through arm (176) (see FIG. 6) of a cartridge (628) in the open configuration. Cartridge housing (132) (see FIG. 6) has been removed for clarity and improved visibility of rod lock retaining pin (630). As shown in FIGS. 24-26, rod lock retaining pin (630) includes longitudinally extending slot (182) through which rod lock retaining pin (630) receives and guides upper lateral end (186) of knife (32) between closed and open configurations. Slot (182) extends transversely through a portion of rod lock retaining pin (630) such that slot (182) does not extend entirely transversely therethrough. Rod lock retaining pin (630) further includes expansion slot (483), which is generally thinner than slot (182), that extends longitudinally from an intermediate pin portion (576) of rod lock retaining pin (630) through distal end portion (577) of rod lock retaining pin (630) as discussed above with two resilient extensions (578) and distal head (579).

A retaining pin actuation mechanism (637) further includes a closure rod (886) that is configured to translatably extend through rod lock retaining pin (630) to selectively direct distal head (579) between contracted and expanded states independent of the position of knife (32). Rod lock retaining pin (630) includes an elongate aperture (888) that extends coaxially through rod lock retaining pin (630), which is configured to receive closure rod (886) such that closure rod (886) may slide longitudinally back and forth within rod lock retaining pin (630). For example, sliding closure rod (886) distally through rod lock retaining pin (630) causes closure rod (886) to engage shoulders (581) (see FIG. 29A) for expanding distal head (579) to the expanded position for locking with distal end portion (564) of end effector (616).

Figure 27:
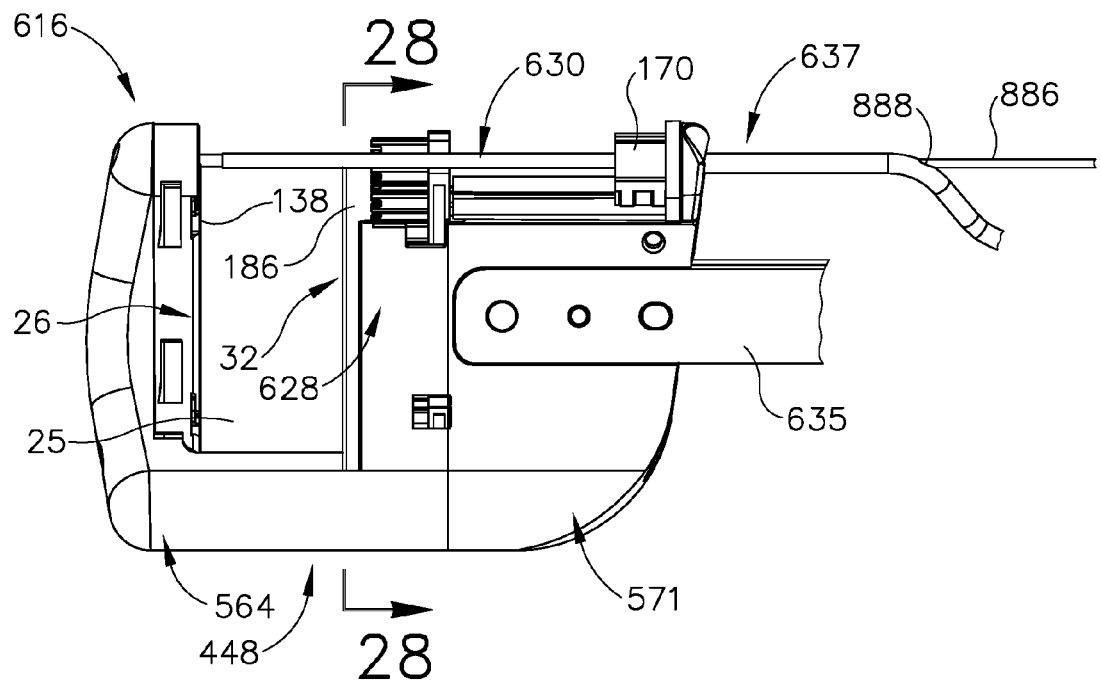
FIG. 27 depicts a right side view of the end effector of FIG. 24, with the retaining pin in an unlocked closed position.
Figure 28:
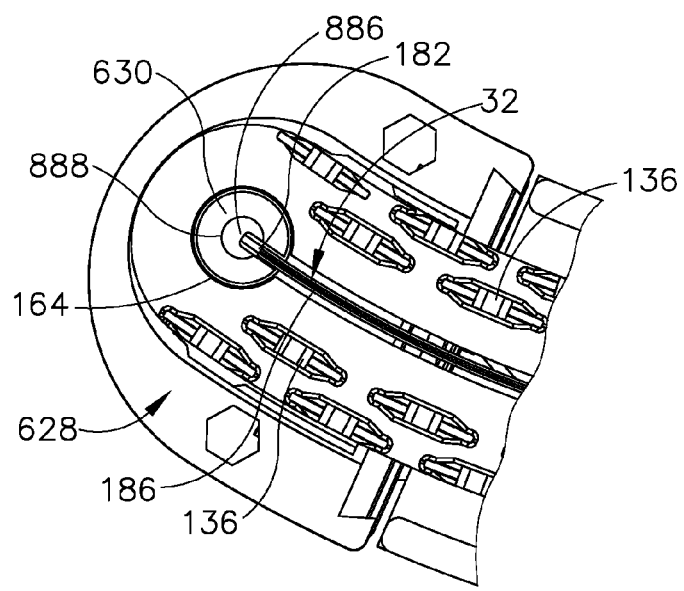
FIG. 28 depicts a cross-sectional view of a portion of the end effector of FIG. 27, taken along section line 28-28 of FIG. 27.

FIGS. 27 and 28 show retaining pin actuation mechanism (637) in the closed configuration. With respect to FIG. 28, slot (182) in rod lock retaining pin (630) slidably receives upper lateral end (186) of knife (32) proximate to closure rod (886) slidably received within elongate aperture (888). Closure rod (886) may thus be selectively translated independently of knife (32) such that closure rod (886) may be locked or unlocked from distal end portion (564) of end effector (616) (see FIG. 27) regardless of the position of knife (32). It will be appreciated that closure rod (886) may be operatively connected to handle and shaft assemblies (612, 614) so that the operator may selectively direct movement of closure rod (886), such as by mechanisms similar to slide (18) (see FIG. 1A). Alternatively, closure rod (886) may have a free end that is configured to be gripped by the operator and manipulated for moving closure rod (886). It will be further appreciated that closure rod (886) may be rigid or flexible so long as closure rod (886) is configured to expand distal head (579) (see FIG. 26) for use. Various suitable alternative mechanisms that may be used to drive movement of closure rod (886) will be apparent to those of ordinary skill in the art in view of the teachings herein.

Figure 29A:
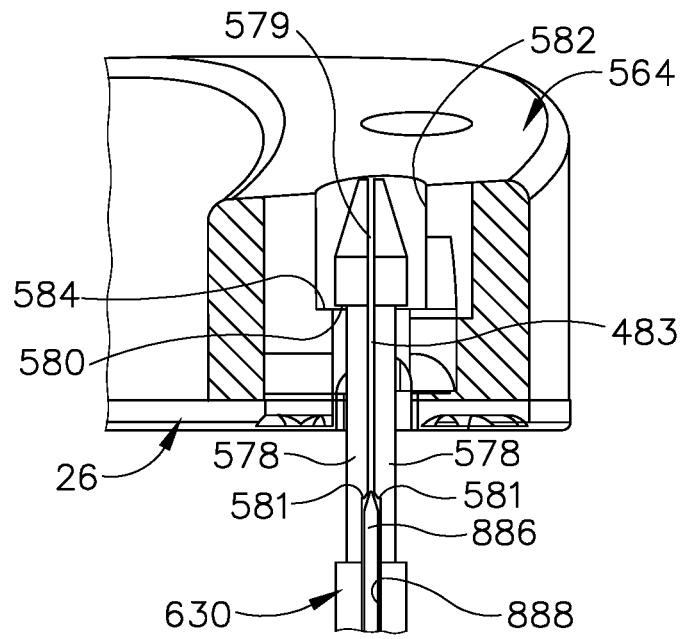
FIG. 29A depicts a cross-sectional view of a portion of the end effector of FIG. 27, with the retaining pin in the unlocked closed position, taken along a centerline of the retaining pin.
Figure 29B:
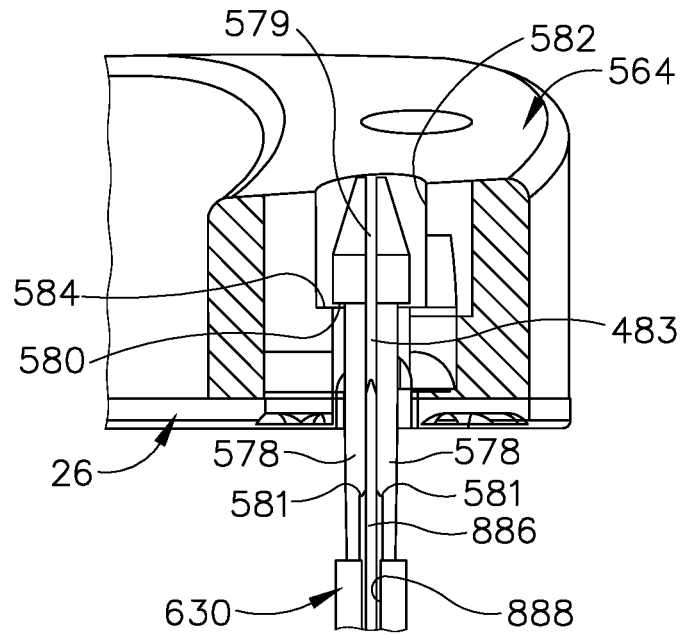
FIG. 29B depicts a cross-sectional view of a portion of the end effector of FIG. 27, with the retaining pin in a locked closed position.

FIGS. 29A-29B illustrate rod lock guide pin (630) locking from an unlocked closed position to the locked closed position. FIG. 29A shows knife lock guide pin (630) in the unlocked closed position following distal movement directed by slide (18) (see FIG. 1A and FIG. 2A) of retaining pin actuation mechanism (637). Regardless of whether or not cartridge (628) and knife (32) have already been moved distally toward anvil (26), the operator selectively translates closure rod (886) distally through elongate aperture (888). Closure rod (886) continues distally such that closure rod (886) engages shoulders (581) to wedge between resilient extensions (578) and expand distal head (579) outwardly from the contracted state to the expanded state. Thereby, distal head (579) is effectively captured in distal portion of retaining pin bore (582) as shown in FIG. 29B. Distal annular ledge (584) of retaining pin bore (582) may then engage proximal annular ledge (580) of rod lock retaining pin (630) to inhibit deflection of distal end portion (564) of end effector (616) as cartridge (628) (see FIG. 27) and tissue are compressed against anvil (26). While exemplary rod lock guide pin (630) is expanded via closure rod (886) in the present example and effectively braces distal end portion (564) in tension, it will be appreciated that alternative structures may expand alternative guide pins; or may otherwise lock with distal end portion (564) such that alternative guide pins may brace distal end portion (564) in compression, as well. To this end, the invention described herein is not intended to be unnecessarily limited to exemplary rod lock guide pin (630).

3. Exemplary Cam Lock Retaining Pin with Cartridge Cam Mechanism and Ledge Lock

Figure 30A:
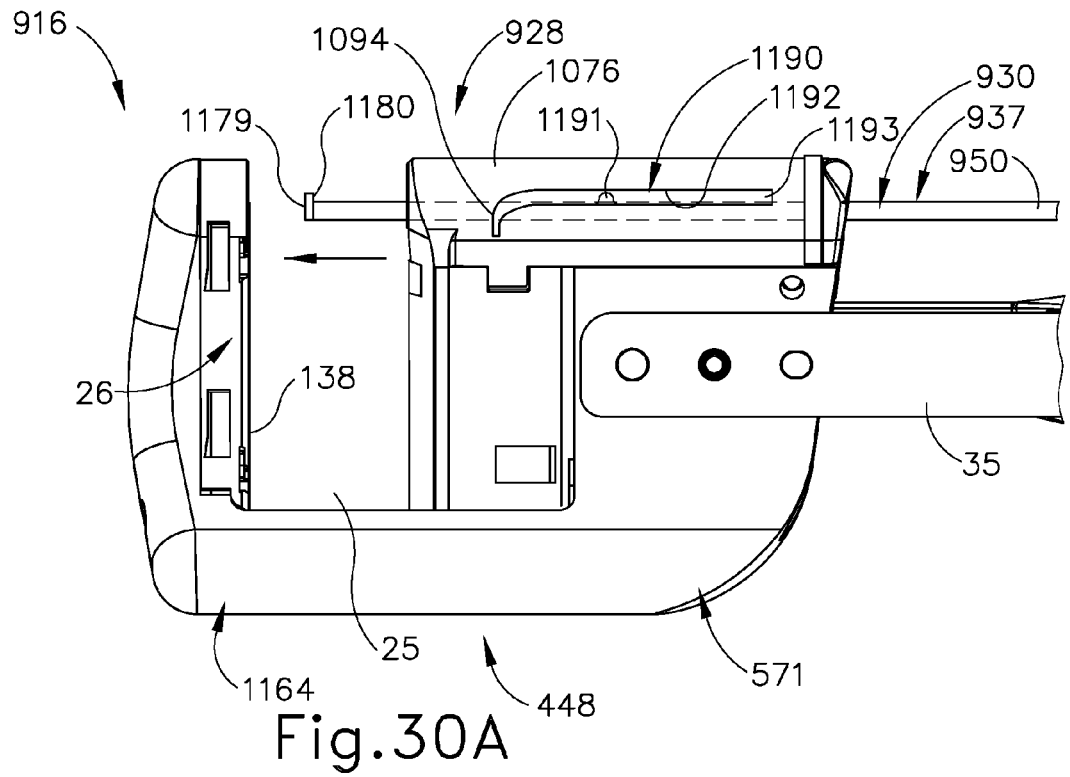
FIG. 30A depicts a right side view of another exemplary end effector having a retaining pin.
Figure 30B:
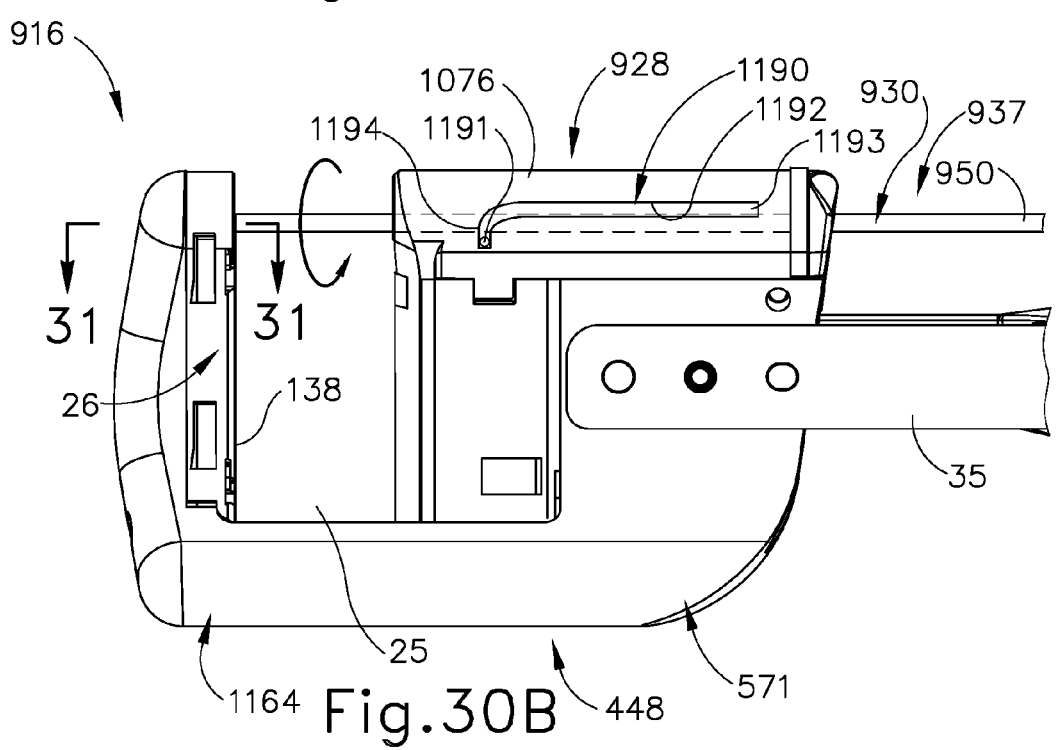
FIG. 30B depicts a right side view of the end effector of FIG. 30A, with the retaining pin moving to a closed position.

FIG. 30A shows another exemplary alternative end effector (916), where a cam lock retaining pin (930) extends through arm (1076) of a cartridge (928) translating from the open configuration toward the closed configuration. As shown in FIGS. 30A-30B, a retaining pin actuation mechanism (937) includes cam lock retaining pin (930) extending directly from a push rod (950) without coupling via couplet (170) (see FIG. 18). Alternatively, cam lock retaining pin (930) may be connected to couplet (170) and push rod (50) for actuation via slide (18) (see FIGS. 1A and 2A) as discussed above in greater detail.

Retaining pin actuation mechanism (937) further includes a cam mechanism (1190) that is configured to guide rotation of cam lock retaining pin (930) as cam lock retaining pin (930) translates into the locked closed position to simultaneously lock and close cam lock retaining pin (930) with distal end portion (1164) of end effector (916). More particularly, cam mechanism (1190) includes a cam tab (1191) extending transversely from cam lock retaining pin (930) and a cam slot (1192) in cartridge housing (132) of cartridge (928). Cam tab (1191) is slidably received within cam slot (1192), which has a proximal linear portion (1193) extending to a distal arcuate portion (1194). Cam slot (1192) is configured to guide rotational movement of cam tab (1191) and, in turn, rotational movement of cam lock retaining pin (930) as push rod (950) distally pushes cam lock retaining pin (930) to distal end portion (1164) of end effector (916) for locking cam lock retaining pin (930) to distal end portion (1164) of end effector (916).

Figure 31:
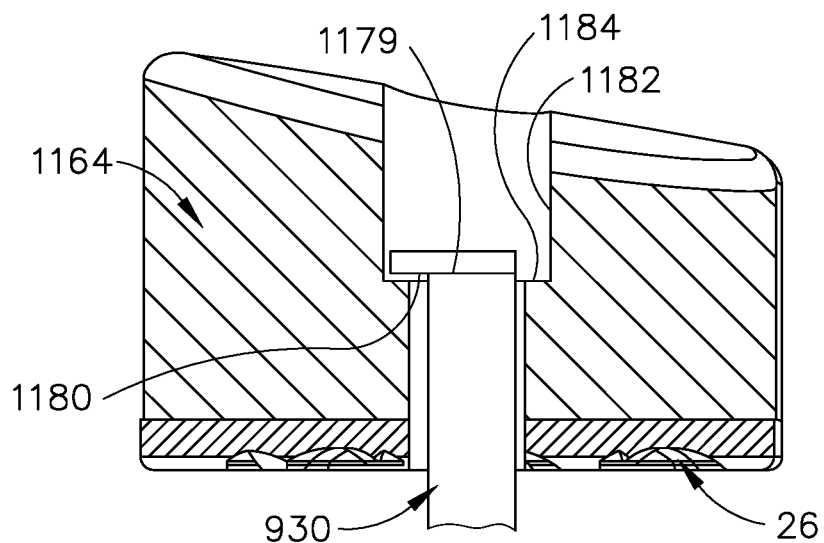
FIG. 31 depicts a cross-sectional view of a portion of the end effector of FIG. 30A, taken along section line 31-31 of FIG. 30B.

A distal head (1179) of cam lock retaining pin (930) is configured to be translatably and rotatably received within a retaining pin bore (1182) of distal end portion (1164) and secured thereto as shown in FIG. 31. Distal head (1179) of cam lock retaining pin (930) defines a proximal oblong ledge (1180), whereas retaining pin bore (1182) is generally oblong in shape to define a distal oblong ledge (1184) (see FIG. 32A). Proximal oblong ledge (1180) is effectively keyed to retaining pin bore (1182) such that as distal head (1179) is configured to translate through retaining pin bore (1182) and then rotate. Proximal oblong ledge (1180) then engages distal oblong ledge (1184). Distal head (1179) is thereby configured to rotatably lock within retaining pin bore (1182) to the closed locked position. While retaining pin bore (1182) and ledge (1180) are oblong in shape so as to overlap when rotated in the present example, it will be appreciated that alternative non-circular shapes may be similarly rotated relative to each other to achieve similarly overlapping and engaging surfaces. For example, such shapes may include, but are not limited to rounded shapes, polygonal shapes, or any combination thereof.

In use, the operator selectively directs push rod (950) distally such that cam slot (1192) guides cam tab (1191) linearly through proximal linear portion (1193) of cam slot (1192) as shown in FIG. 30A and FIG. 31. Cam lock retaining pin (930) thus slides distally toward retaining pin bore (1180) for capturing tissue (not shown) between cartridge (928) and anvil (26) in the unlocked closed configuration. As distal head (1179) is introduced into the proximal portion of retaining pin bore (1182) as shown in FIG. 30B, cam tab (1191) slides into distal arcuate portion (1194), which, in turn, causes cam lock retaining pin to rotate in the distal portion of retaining pin bore (1182). Proximal oblong edge (1180) follows by rotating to overlap with distal oblong edge (1184). Thereby, distal head (1179) is effectively captured in distal portion of retaining pin bore (1182) as shown in FIGS. 30B-31. Distal oblong ledge (1184) of retaining pin bore (1182) may then engage proximal oblong ledge (1180) of cam lock retaining pin (930) to inhibit deflection of distal end portion (1164) of end effector (916) as cartridge (928) and tissue are compressed against anvil (26). While cam lock guide pin (930) effectively braces distal end portion (1164) in tension in the present example, it will be appreciated that alternative structures may expand alternative guide pins; or may otherwise lock with distal end portion (1164) such that alternative guide pins may brace distal end portion (1164) in compression, as well. To this end, the invention described herein is not intended to be unnecessarily limited to exemplary cam lock guide pin (930).

4. Exemplary Cam Lock Retaining Pin with Pin Cam Mechanism and Ledge Lock

Figure 32A:
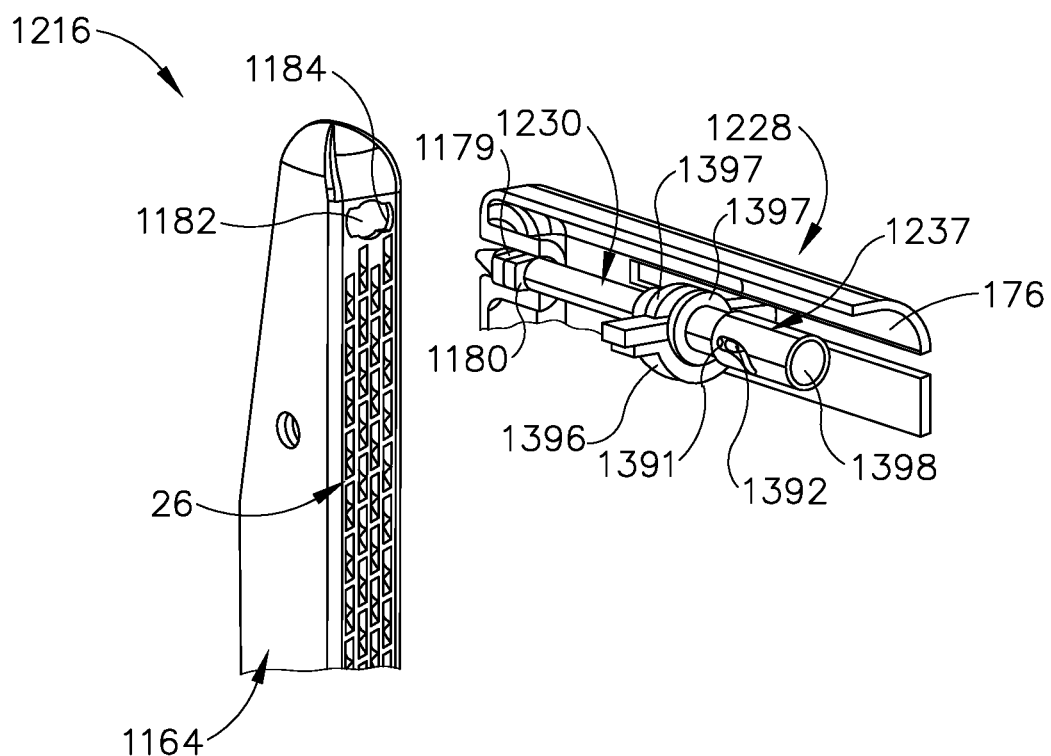
FIG. 32A depicts a rear perspective view of another exemplary end effector having a retaining pin in an open position.
Figure 32B:
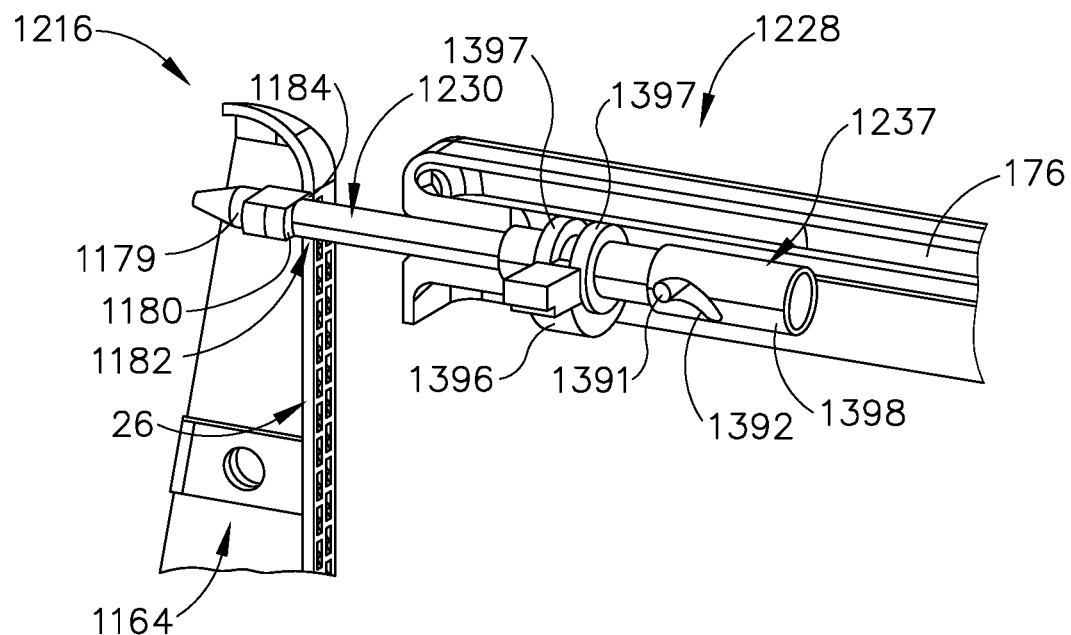
FIG. 32B depicts the rear perspective view of the end effector of FIG. 32A, with the retaining pin in an unlocked closed position.
Figure 32C:
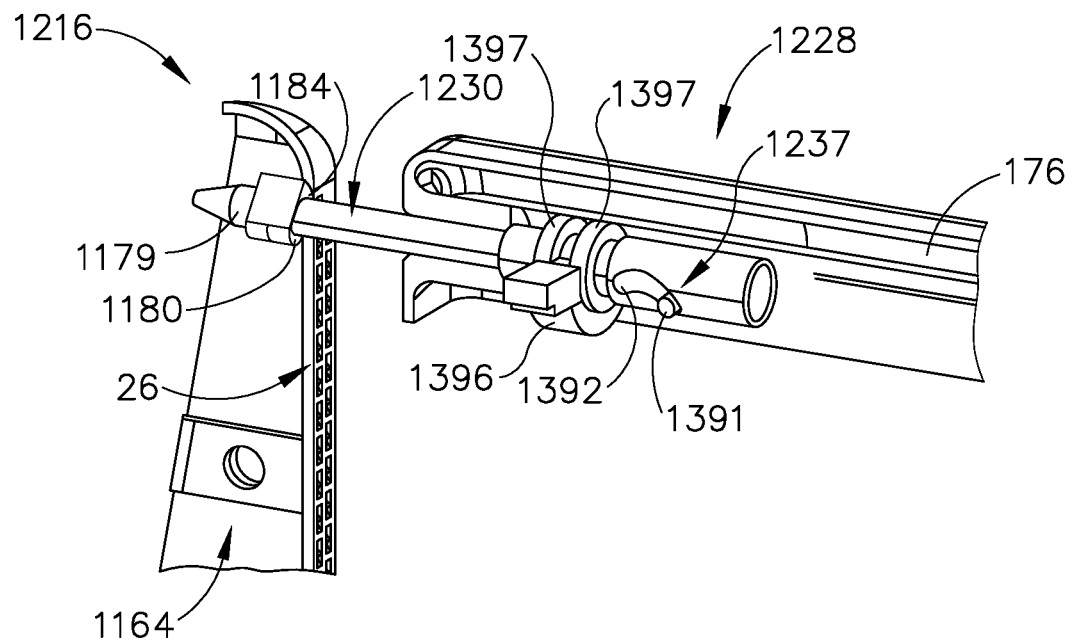
FIG. 32C depicts the rear perspective view of the end effector of FIG. 32A, with the retaining pin in a locked closed position.

FIGS. 32A-32C show another exemplary alternative end effector (1216), where a cam lock retaining pin (1230) extends through arm (176) of a cartridge (1228) translating from the open configuration toward the closed configuration. A retaining pin actuation mechanism (1237) includes cam lock retaining pin (1230) rotatably resting on a support cradle (1396) between opposing flanges (1397). In addition, a distal end portion of cam lock retaining pin (1230) is rotatably driven by retaining pin actuation mechanism (1237), which includes a cam tab (1391) extending from the distal end portion of cam lock retaining pin (1230) received within an arcuate cam slot (1392) of a cam tube (1398).

In use, cam lock retaining pin (1230) may be rotated independently of its translation such that the operator may choose to move cam lock retaining pin (1230) to either open or closed configurations with or without the use of locking the cam lock retaining pin (1230) to the distal end portion (1164) of end effector (1216). More particularly, the operator slides cam lock retaining pin (1230) to the unlocked closed position on support cradle (1396) as shown in FIG. 32B such that distal head (1179) is received within retaining pin bore (1182) as discussed above in greater detail. To lock cam lock retaining pin (1230), push rod (50) (see FIG. 1A), or some alternative pushing mechanism, urges cam tube (1398) distally. Because arcuate cam slot (1392) is configured to direct cam tab (1391) to rotate, the entirety of cam lock retaining pin (1230) also rotates as cam tube (1398) moves distally. In turn, proximal oblong edge (1180) follows by rotating to overlap with distal oblong edge (1184). Thereby, distal head (1179) is effectively captured in distal portion of retaining pin bore (1182) as shown in FIG. 32C. Distal oblong ledge (1184) of retaining pin bore (1182) may then engage proximal oblong ledge (1180) of cam lock retaining pin (1230) to inhibit deflection of distal end portion (1164) of end effector (1216) as cartridge (1228) and tissue are compressed against anvil (26). While cam lock guide pin (1230) effectively braces distal end portion (1164) in tension in the present example, it will be appreciated that alternative structures may expand alternative guide pins; or may otherwise lock with distal end portion (1164) such that alternative guide pins may brace distal end portion (1164) in compression, as well. To this end, the invention described herein is not intended to be unnecessarily limited to exemplary cam lock guide pin (1230).

5. Exemplary Cam Lock Retaining Pin and Threaded Lock

Figure 33A:
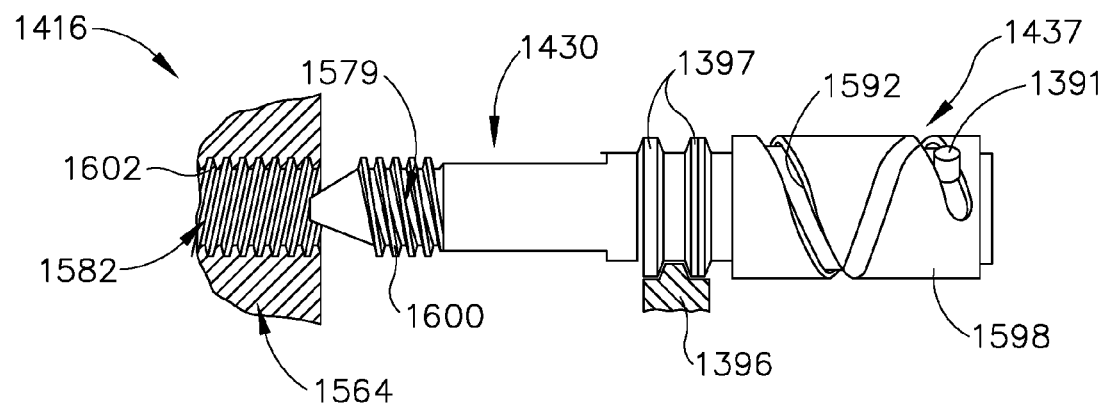
FIG. 33A depicts a right side sectional view of another exemplary end effector having a retaining pin with various components removed for clarity.
Figure 33B:
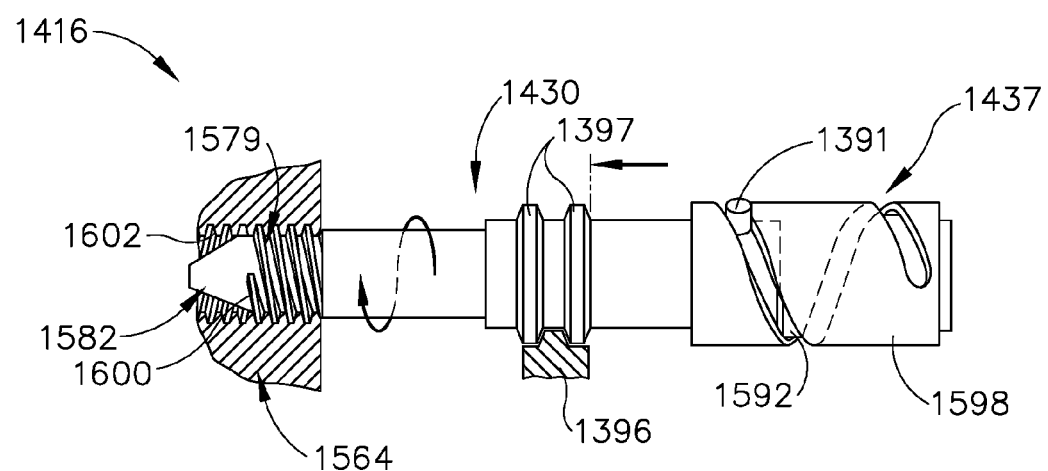
FIG. 33B depicts a right side sectional view of the end effector of FIG. 33A, with the retaining pin moving to the locked closed position.

FIGS. 33A-33B show another alternative end effector (1416) having a cam lock retaining pin (1430) received on a support cradle (1396) between flanges (1397). Cam lock retaining pin (1430) includes a distal head (1579) having a plurality of outer threads (1600) configured to threadably engage with a plurality of inner threads (1602) within a retaining pin bore (1582). Cam lock retaining pin (1430) is rotatably driven distally from the open position to the locked closed position via retaining pin actuation mechanism (1437). Retaining pin actuation mechanism (1437) includes a cam tab (1391) extending from the distal end portion of cam lock retaining pin (1430), which is received within a spiral cam slot (1592) of a cam tube (1598). Cam tube (1598) maintains a fixed position relative to pin (1430). Thus, as support cradle (1396) pushes cam lock retaining pin (1430) distally, spiral cam slot (1592) directs cam tab (1391) to spiral through spiral cam slot (1592), causing cam lock retaining pin (1430) to simultaneously translate and rotate. The simultaneous translation and rotation continues until distal head (1579) fully threads into retaining pin bore (1582) and seats in the closed locked position. Thus, cam lock retaining pin (1430) may brace a distal end portion (1564) of end effector (1416) in both tension and compression due to the threaded engagement. It will be appreciated that support cradle (1396) may be distally and proximally driven by an operative connection with push rod (50) (see FIG. 1A) or some other alternative mechanism. In any case, the invention described herein is not intended to be unnecessarily limited to exemplary cam lock retaining pin (1430).

6. Exemplary Snap Lock Retaining Pin and Ledge Lock

FIGS. 34A-34C show another exemplary alternative end effector (1616) that includes a snap lock retaining pin (1630), which is configured to move from the open position to the locked closed position with distal end portion (1764). A distal end portion (1777) of lock retaining pin (1630) has a distal head in the form of a resilient snap (1779) defining a proximal ledge (1780). In addition, a retaining pin bore (1782) defines a distal ledge (1784). Resilient snap (1779) is configured to resiliently bend about distal ledge (1784) and snap about distal ledge (1784) such that proximal ledge (1784) of resilient snap (1779) engages distal ledge (1784) within retaining pin bore (1782).

In use, a retaining pin actuation mechanism (1637) may include push rod (50) to direct snap lock retaining pin (1630) distally from the open position toward retaining pin bore (1782) as shown in FIG. 34A. As shown in FIG. 34B, resilient snap (1779) is forced distally over distal ledge (1784) within retaining pin bore (1782) until proximal ledge (1784) slides over distal ledge (1784) for engagement thereagainst in the locked closed position shown in FIG. 34C. While snap lock guide pin (1630) effectively braces distal end portion (1764) in tension in the present example, it will be appreciated that alternative structures may expand alternative guide pins; or may otherwise lock with distal end portion (1764) such that alternative guide pins may brace distal end portion (1764) in compression, as well. To this end, the invention described herein is not intended to be unnecessarily limited to exemplary snap lock guide pin (1630).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body; (b) a shaft assembly extending distally from the body; and (c) an end effector extending distally from the shaft assembly and configured to receive a cartridge for manipulating tissue of a patient, the end effector including: (i) a distal end portion, (ii) a proximal end portion, (iii) a gap between the distal end portion and the proximal end portion, and (iv) a retaining pin having a distal head, wherein the retaining pin is selectively movable from an open position to a locked closed position, wherein the retaining pin in the open position is proximally positioned relative to the gap such that the gap is configured to receive the tissue, wherein the retaining pin in the locked closed position extends across the gap such that retaining pin is configured to capture the tissue within the gap, wherein the distal head of the retaining pin is configured engage the distal end portion of the end effector and secure the distal end portion of the end effector relative to the proximal end portion of the end effector via the retaining pin projecting therebetween.

Example 2

The surgical instrument of Example 1, further comprising a cartridge having a cartridge housing, wherein the retaining pin is at least partially contained within the cartridge housing in the open position.

Example 3

The surgical instrument of Example 2, wherein the cartridge includes at least one of a knife or a plurality of staples, wherein the knife is configured to cut the tissue, and wherein the plurality of staples are configured to fasten the tissue.

Example 4

The surgical instrument of any one or more of Examples 1 through 3, wherein the distal end portion of the end effector includes a bore configured to receive the distal head of the retaining pin in the locked closed position.

Example 5

The surgical instrument of Example 4, wherein the distal end portion of the end effector has a first ledge within the bore, wherein the distal head of the retaining pin has a second ledge, wherein the second ledge is configured to overlap within the first ledge to lock distal head of the retaining pin to the distal end portion of the end effector.

Example 6

The surgical instrument of Example 5, wherein the distal head of the retaining pin is configured to expand from a contracted state to an expanded state for overlapping the first and second ledges.

Example 7

The surgical instrument of Example 6, wherein the end effector further includes a knife configured to move from a proximal knife position toward a distal knife position, wherein at least a portion of the knife is slidably received within the retaining pin, wherein the knife is configured to expand the distal head from the contracted state to the expanded state when the knife is moved from the proximal knife position toward the distal knife position.

Example 8

The surgical instrument of Example 7, wherein the knife is configured to move from the distal knife position toward the proximal knife position, and wherein the knife is configured to contract the distal head from the expanded state to the contracted state and unlock the distal head of the retaining pin from the distal end portion of the end effector when the knife is moved from the distal knife position toward the proximal knife position.

Example 9

The surgical instrument of Example 6, wherein the end effector further includes a closure member configured to move from a proximal member position toward a distal member position, wherein the closure member is slidably received within the retaining pin, wherein the closure member is configured to expand the distal head from the contracted state to the expanded state when the closure member is moved from the proximal member position toward the distal member position.

Example 10

The surgical instrument of Example 9, wherein the closure member is configured to move from the distal member position toward the proximal member position, and wherein the closure member is configured to contract the distal head from the expanded state to the contracted state and unlock the distal head of the retaining pin from the distal end portion of the end effector when the closure member is moved from the distal member position toward the proximal member position.

Example 11

The surgical instrument of Example 5, wherein the end effector includes a cam mechanism having a cam tab and a cam slot, wherein the cam tab extends from the retaining pin within the cam slot, and wherein the cam slot is configured to guide movement of the retaining pin such that the second ledge rotatably overlaps with the first ledge into the locked closed position.

Example 12

The surgical instrument of Example 11, further comprising a cartridge having a cartridge housing, wherein the cam slot is defined by the cartridge housing.

Example 13

The surgical instrument of Example 11, wherein the cam slot is defined by a cam tube, and wherein the retaining pin is received within the cam tube.

Example 14

The surgical instrument of Example 4, wherein the distal end portion of the end effector has a first plurality of threads within the bore, the distal head of the retaining pin has a second plurality of threads, and the second plurality of threads is configure to threadably engage the first plurality of threads to lock the distal head of the retaining pin to the distal end portion of the end effector.

Example 15

The surgical instrument of Example 14, wherein the end effector includes a cam mechanism having a cam tab and a spiral cam slot, wherein the cam tab extends from the retaining pin within the spiral cam slot, and wherein the spiral cam slot is configured to guide movement of the retaining pin such that the second plurality of threads is rotatably driven into engagement with the first plurality of threads into the locked closed position.

Example 16

The surgical instrument of Example 4, wherein the distal head of the retaining pin includes a resilient snap, wherein the distal end portion of the end effector has a first ledge within the bore, wherein the resilient snap of the retaining pin has a second ledge, wherein the second ledge is configured to overlap within the first ledge to lock distal head of the retaining pin to the distal end portion of the end effector.

Example 17

A cartridge for an end effector of a surgical instrument, wherein the end effector has a distal end portion, a proximal end portion, and a gap therebetween for receiving the tissue, the cartridge comprising: (a) a cartridge housing configured to be received by the end effector, wherein the cartridge housing contains at least one of a knife or a plurality of staples, wherein the knife is configured to cut tissue, and wherein the plurality of staples are configured to fasten tissue; and (b) a retaining pin having a distal head, wherein the retaining pin is selectively movable from an open position to a locked closed position, wherein the retaining pin in the open position is configured to be proximally positioned relative to the gap for receiving tissue, wherein the retaining pin in the locked closed position is configured to extend across the gap such that retaining pin is configured to capture tissue within the gap, wherein the retaining pin is configured engage the distal end portion of the end effector and secure the distal end portion of the end effector relative to the proximal end portion of the end effector.

Example 18

The cartridge of Example 17, wherein the retaining pin is at least partially contained within the cartridge housing in the open position.

Example 19

A method of manipulating tissue of a patient with a surgical instrument, wherein the surgical instrument includes a body, a shaft assembly extending distally from the body, and an end effector extending distally from the shaft assembly, wherein the end effector includes a cartridge configured to manipulate the tissue, a distal end portion, a proximal end portion, a gap between the distal and proximal end portions configured to receive the tissue, and a retaining pin, the method comprising: (a) positioning the tissue within the gap; (b) moving the retaining pin from an open position toward a locked closed position to capture the tissue within the gap; (c) engaging a distal head of the retaining pin with the distal end portion of the end effector in the locked closed position to secure the distal end portion of the end effector relative to the proximal end portion of the end effector; and (d) manipulating the tissue of the patient with the cartridge.

Example 20

The method of Example 19, further comprising inhibiting deflection of the distal end portion of the end effector with the retaining pin in the locked closed position.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

The entire disclosures of: U.S. Pat. No. 5,403,312, entitled "Electrosurgical Hemostatic Device," which issued on Apr. 4, 1995; U.S. Pat. No. 7,000,818, entitled "Surgical Stapling Instrument having Separate Distinct Closing and Firing Systems," which issued on Feb. 21, 2006; U.S. Pat. No. 7,422,139, entitled "Motor-Driven Surgical Cutting and Fastening Instrument with Tactile Position Feedback," which issued on Sep. 9, 2008; U.S. Pat. No. 7,464,849, entitled "Electro-Mechanical Surgical Instrument with Closure System and Anvil Alignment Components," which issued on Dec. 16, 2008; U.S. Pat. No. 7,670,334, entitled "Surgical Instrument Having An Articulating End Effector," which issued on Mar. 2, 2010; U.S. Pat. No. 7,753,245, entitled "Surgical Stapling Instruments," which issued on Jul. 13, 2010 U.S. Pat. No. 8,393,514, entitled "Selectively Orientable Implantable Fastener Cartridge," which issued on Mar. 12, 2013 U.S. patent application Ser. No. 11/343,803, entitled "Surgical Instrument Having Recording Capabilities;" now U.S. Pat. No. 7,845,537; U.S. patent application Ser. No. 12/031,573, entitled "Surgical Cutting And Fastening Instrument Having RF Electrodes," filed Feb. 14, 2008, now abandoned; U.S. patent application Ser. No. 12/031,873, entitled "End Effectors For A Surgical Cutting And Stapling Instrument," filed Feb. 15, 2008, now U.S. Pat. No. 7,980,443; U.S. patent application Ser. No. 12/235,782, entitled "Motor-Driven Surgical Cutting Instrument," now U.S. Pat. No. 8,210,411; U.S. patent application Ser. No. 12/249,117, entitled "Powered Surgical Cutting And Stapling Apparatus With Manually Retractable Firing System," now U.S. Pat. No. 8,608,045; U.S. patent application Ser. No. 12/647,100, entitled "Motor-Driven Surgical Cutting Instrument with Electric Actuator Directional Control Assembly," filed Dec. 24, 2009; now U.S. Pat. No. 8,220,688; U.S. patent application Ser. No. 12/893,461, entitled "Staple Cartridge," filed Sep. 29, 2012, now U.S. Pat. No. 8,733,613; U.S. patent application Ser. No. 13/036,647, entitled "Surgical Stapling Instrument," filed Feb. 28, 2011, now U.S. Pat. No. 8,561,870; U.S. patent application Ser. No. 13/118,241, entitled "Surgical Stapling Instruments With Rotatable Staple Deployment Arrangements," now U.S. Patent Application Publication No. 2012/0298719, issued as U.S. Pat. No. 9,072,535 on Jul. 7, 2015; U.S. patent application Ser. No. 13/524,049, entitled "Articulatable Surgical Instrument Comprising A Firing Drive," filed on Jun. 15, 2012; now U.S. Patent Application Publication No. 2013/0334278, issued as U.S. Pat. No. 9,101,358 on Aug. 11, 2015; U.S. patent application Ser. No. 13/800,025, entitled "Staple Cartridge Tissue Thickness Sensor System," filed on Mar. 13, 2013, now U.S. Patent Application Publication No. 2014/0263551, issued as U.S. Pat. No. 9,345,481 on May 24, 2016; U.S. patent application Ser. No. 13/800,067, entitled "Staple Cartridge Tissue Thickness Sensor System," filed on Mar. 13, 2013, now U.S. Patent Application Publication No. 2014/0263552, now abandoned; U.S. Patent Application Publication No. 2007/0175955, entitled "Surgical Cutting And Fastening Instrument With Closure Trigger Locking Mechanism," filed Jan. 31, 2006, now abandoned; and U.S. Patent Application Publication No. 2010/0264194, entitled "Surgical Stapling Instrument With An Articulatable End Effector," filed Apr. 22, 2010, now U.S. Pat. No. 8,308,040, are hereby incorporated by reference herein.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
(a) a body;
(b) a shaft assembly extending distally from the body; and
(c) an end effector extending distally from the shaft assembly and configured to receive a cartridge for manipulating tissue of a patient, the end effector including:
  (i) a distal end portion,
  (ii) a proximal end portion,
  (iii) a gap between the distal end portion and the proximal end portion, and
  (iv) a retaining pin having a distal head configured to expand from a contracted state to an expanded state, wherein the retaining pin is selectively movable from an open position to a locked or unlocked closed position, wherein the retaining pin in the open position is proximally positioned relative to the gap such that the gap is configured to receive the tissue, wherein the retaining pin in the closed position extends across the gap such that retaining pin is configured to capture the tissue within the gap,
  (v) a lock member having at least a portion thereof configured to engage the retaining pin to selectively expand the retaining pin from the contracted state to the expanded state and further selectively contract the retaining pin from the expanded state to the contracted state, wherein the distal head in the contracted state is disengaged from the distal end portion of the end effector in the unlocked closed position for insertion or removal therefrom, wherein the distal head of the retaining pin is configured engage the distal end portion of the end effector in the locked closed position and secure the distal end portion of the end effector relative to the proximal end portion of the end effector via the retaining pin projecting therebetween.

2. The surgical instrument of claim 1, further comprising a cartridge having a cartridge housing, wherein the retaining pin is at least partially contained within the cartridge housing in the open position.

3. The surgical instrument of claim 2, wherein the cartridge includes at least one of a knife or a plurality of staples, wherein the knife is configured to cut the tissue, and wherein the plurality of staples are configured to fasten the tissue.

4. The surgical instrument of claim 1, wherein the distal end portion of the end effector includes a bore configured to receive the distal head of the retaining pin in the locked closed position.

5. The surgical instrument of claim 4, wherein the distal end portion of the end effector has a first ledge within the bore, wherein the distal head of the retaining pin has a second ledge, wherein the second ledge is configured to overlap with the first ledge to lock the distal head of the retaining pin to the distal end portion of the end effector.

6. The surgical instrument of claim 5, wherein the lock member further includes a knife configured to move from a proximal knife position toward a distal knife position, wherein at least a portion of the knife is slidably received within the retaining pin, wherein the knife is configured to expand the distal head from the contracted state to the expanded state when the knife is moved from the proximal knife position toward the distal knife position.

7. The surgical instrument of claim 6, wherein the knife is configured to move from the distal knife position toward the proximal knife position, and wherein the at least the portion of the knife is configured to contract the distal head from the expanded state to the contracted state and unlock the distal head of the retaining pin from the distal end portion of the end effector when the knife is moved from the distal knife position toward the proximal knife position.

8. The surgical instrument of claim 4, wherein the lock member further includes a closure body configured to move from a proximal member position toward a distal member position, wherein the closure body is slidably received within the retaining pin, wherein the closure body is configured to expand the distal head from the contracted state to the expanded state when the closure body is moved from the proximal member position toward the distal member position.

9. The surgical instrument of claim 8, wherein the closure body is configured to move from the distal member position toward the proximal member position, and wherein the closure body is configured to contract the distal head from the expanded state to the contracted state and unlock the distal head of the retaining pin from the distal end portion of the end effector when the closure body is moved from the distal member position toward the proximal member position.

10. The surgical instrument of claim 1, wherein the distal head of the retaining pin in the contracted state defines a first diameter, wherein the distal head of the retaining pin in the expanded state defines a second diameter, and wherein the first diameter is smaller than the second diameter.

11. The surgical instrument of claim 1, wherein the lock member is movably positioned within at least a portion of the retaining pin.

12. The surgical instrument of claim 1, wherein the distal head of the retaining pin is resiliently biased toward the contracted state.

13. A surgical instrument, comprising:
(a) a body;
(b) a shaft assembly extending distally from the body; and
(c) an end effector extending distally from the shaft assembly and configured to receive a cartridge for manipulating tissue of a patient, the end effector including:
(i) a distal end portion,
(ii) a proximal end portion,
(iii) a gap between the distal end portion and the proximal end portion, and
(iv) a retaining pin selectively movable from an open position to a locked or unlocked closed position, wherein the retaining pin in the open position is proximally positioned relative to the gap such that the gap is configured to receive the tissue, wherein the retaining pin in the locked closed position extends across the gap such that retaining pin is configured to capture the tissue within the gap,
(v) a knife having at least a portion thereof received against the retaining pin and configured to move from a proximal knife position toward a distal knife position and thereby direct the retaining pin to the locked closed position, wherein the retaining pin is configured engage the distal end portion of the end effector in the locked closed position and secure the distal end portion of the end effector relative to the proximal end portion of the end effector via the retaining pin projecting therebetween.

14. The surgical instrument of claim 13, wherein the retaining pin in the unlocked closed position is disengaged from the distal end portion of the end effector for insertion or removal therefrom.

15. The surgical instrument of claim 14, wherein the knife is configured to move from the distal knife position to the proximal knife position to thereby direct the retaining pin to the unlocked closed position.

16. The surgical instrument of claim 13, wherein the retaining pin has a distal head selectively movable from a contracted state to an expanded state to engage the distal end portion in the locked closed position, wherein the distal head of the retaining pin in the contracted state defines a first diameter, wherein the distal head of the retaining pin in the expanded state defines a second diameter, and wherein the first diameter is smaller than the second diameter.

17. The surgical instrument of claim 13, wherein at least a portion of the knife is movably positioned within at least a portion of the retaining pin.

18. The surgical instrument of claim 13, wherein the retaining pin has a distal head selectively movable from a contracted state to an expanded state to engage the distal end portion in the locked closed position, and wherein the distal head of the retaining pin is resiliently biased toward the contracted state.

19. A surgical instrument, comprising:
(a) a body;
(b) a shaft assembly extending distally from the body; and
(c) an end effector extending distally from the shaft assembly and configured to receive a cartridge for manipulating tissue of a patient, the end effector including:
(i) a distal end portion,
(ii) a proximal end portion,
(iii) a gap between the distal end portion and the proximal end portion, and
(iv) a retaining pin having a distal head, wherein the retaining pin is selectively movable from an open position to a locked closed position, wherein the retaining pin in the open position is proximally positioned relative to the gap such that the gap is configured to receive the tissue, wherein the retaining pin in the locked closed position extends across the gap such that retaining pin is configured to capture the tissue within the gap, wherein the distal head of the retaining pin is configured engage the distal end portion of the end effector and secure the distal end portion of the end effector relative to the proximal end portion of the end effector via the retaining pin projecting therebetween, wherein the distal end portion of the end effector includes a bore configured to receive the distal head of the retaining pin in the locked closed position, wherein the distal end portion of the end effector has a first ledge within the bore, wherein the distal head of the retaining pin has a second ledge, wherein the second ledge is configured to overlap with the first ledge to lock the distal head of the retaining pin to the distal end portion of the end effector, wherein the distal head of the retaining pin is configured to expand from a contracted state to an expanded state for overlapping the first and second ledges, and wherein the end effector further includes a knife configured to move from a proximal knife position toward a distal knife position, wherein at least a portion of the knife is slidably received within the retaining pin, wherein the knife is configured to expand the distal head from the contracted state to the expanded state when the knife is moved from the proximal knife position toward the distal knife position.

20. The surgical instrument of claim 19, wherein the knife is configured to move from the distal knife position toward the proximal knife position, and wherein the knife is configured to contract the distal head from the expanded state to the contracted state and unlock the distal head of the retaining pin from the distal end portion of the end effector when the knife is moved from the distal knife position toward the proximal knife position.

* * * * *